United States Patent
Guan et al.

(10) Patent No.: US 10,179,837 B2
(45) Date of Patent: *Jan. 15, 2019

(54) DENDRONIZED POLYMERS FOR NUCLEIC ACID DELIVERY

(71) Applicant: The Regents of the University of California, Oakland, CA (US)

(72) Inventors: Zhibin Guan, Irvine, CA (US); Hanxiang Zeng, Irvine, CA (US)

(73) Assignee: The Regents of the University of California, Oakland, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/688,718

(22) Filed: Aug. 28, 2017

(65) Prior Publication Data

US 2018/0072849 A1 Mar. 15, 2018

Related U.S. Application Data

(63) Continuation of application No. 14/221,249, filed on Mar. 20, 2014, now Pat. No. 9,745,421.

(60) Provisional application No. 61/803,784, filed on Mar. 20, 2013.

(51) Int. Cl.

| | | |
|---|---|---|
| C08G 83/00 | (2006.01) | |
| C12N 15/113 | (2010.01) | |
| C08G 75/14 | (2006.01) | |
| C12N 15/11 | (2006.01) | |
| C12N 15/87 | (2006.01) | |

(52) U.S. Cl.
CPC ............ *C08G 75/14* (2013.01); *C12N 15/111* (2013.01); *C12N 15/87* (2013.01); *C12N 2310/14* (2013.01); *C12N 2320/32* (2013.01)

(58) Field of Classification Search
None
See application file for complete search history.

(56) References Cited

U.S. PATENT DOCUMENTS

| | | | | |
|---|---|---|---|---|
| 2007/0129305 A1* | 6/2007 | Divita | ............... | C07K 14/00 514/130 |
| 2013/0302257 A1* | 11/2013 | Minko | ............... | C12N 15/87 424/9.361 |
| 2015/0297742 A1* | 10/2015 | Strieker | ............... | A61K 47/48253 424/1.49 |

OTHER PUBLICATIONS

Gössl et al (J. Am. Chem. Soc. 2002, 124, 6860-6865). (Year: 2002).*
Tan et al., Thermosensitive injectable hyaluronic acid hydrogel for adipose tissue engineering. Biomaterials 30(36):6844:6853 (2009).
Tang et al., "In Vitro Gene Delivery by Degraded Polyamidoamine Dendrimers," Bioconjugate Chem 7:703-714 (1996).
Tibbet et al., Hydrogels as Extracellular Matrix Mimics for 3D Cell Culture. Biotechnol Bioeng. 103(4):655-663 (2009).
Toyofuku et al., Natural killer T-cells participate in rejection of islet allografts in the liver of mice. Diabetes 55:34e9 (2006).
Urakami et al.,Living Ring-Opening Polymerization of a Carbohydrate-Derived Lactone for the Synthesis of Protein-Resistant Biomaterials. Biomacromolecules, Jan. 26, 2008, 9, 592-597.

(Continued)

*Primary Examiner* — Richard A Schnizer
(74) *Attorney, Agent, or Firm* — Gavrilovich, Dodd & Lindsey LLP

(57) ABSTRACT

The disclosure provides for dendronized polymers, and the use of the polymers as carriers for the intracellular delivery of nucleic acids.

12 Claims, 17 Drawing Sheets

(56) References Cited

OTHER PUBLICATIONS

Vercruysse et al. Synthesis and in vitro degradation of new polyvalent hydrazide cross-linked hydrogels of hyaluronic acid. Bioconjugate Chem. 8:686-694 (1997).

Wagner, E., "Polymers for siRNA Delivery: Inspired by Viruses to be Targeted, Dynamic, and Precise," Acc Chem Res 45:1005-1013 (2011).

Wakefield et al., "Membrane Activity and Transfection Ability of Amphipathic Polycations as a Function of Alkyl Group Size," Bioconjug Chem 16:1204-1208 (2005).

Wang et al. Substrate flexibility regulates growth and apoptosis of normal but not transformed cells. Am. J. Physiol. Cell Physiol. 279:C1345-1350 (2000).

Weber et al., Cell-matrix interactions improve Beta-cell survival and insulin secretion in three-dimensional culture. Tissue Eng Part A 14:1959e68 (2008).

Yamaguchi et al., Growth Factor Mediated Assembly of Cell Receptor-Responsive Hydrogels J. Am. Chem. Soc. 129:3040-3041 (2007).

Zeng et al. "Multifunctional Dendronized Peptide Polymer Platform for Safe and Effective siRNA Delivery", JACS 135:4962-4965 (Mar. 15, 2013).

Kuklarni et al., "Pendant Polymer:Amino-β-Cyclodextrin:siRNA Guest:Host Nanoparticles as Efficient Vectors for Gene Silencing," J Am Chem Soc 134:7596-7599 (Apr. 30, 2012).

Lee et al., Controlling Mechanical and Swelling Properties of Alginate Hydrogels Independently by Cross-Linker Type and Cross-Linking Density Macromolecules 33, 4291-4294 (2000).

Lee et al., Hydrogels for tissue engineering. J. Chem ReV 101:1869-1879 (2001).

Lee et al. Three-dimensional micropatterning of bioactive hydrogels via two-photon laser scanning photolithography for guided 3D cell migration. Biomaterials 29:2962-2968 (2008).

Lee et al., Growth factor delivery-based tissue engineering: general approaches and a review of recent developments. J R Soc Interface 8:153e70 (2011).

Liao et al., De novo design of saccharide-peptide hydrogels as synthetic scaffolds for tailored cell responses. J Am Chem Soc 131:17638e46 (2009).

Liao et al., Maintaining functional islets through encapsulation in an injectable saccharide-peptide hydrogel. Biomaterials 34(16):3984-91 (Mar. 7, 2013).

Liao et al., The effect of cell-matrix interaction on encapsulated human islets. presented at the Congress of the International Pancreas and Islet Transplantation, (Jun. 2013).

Lin et al., PEG Hydrogels for the Controlled Release of Biomolecules in Regenerative Medicine Pharmacol. Res. 26:631-643 (2009).

Lin et al., Glucagon-like peptide-1 functionalized PEG hydrogels promote survival and function of encapsulated pancreatic beta-cells. Biomacromolecules 10:2460e7 (2009).

Liu et al., "SiRNA Delivery Systems Based on Neutral Cross-Linked Dendrimers," Bioconjug Chem 23:174-183 (Jan. 2012).

Liu et al., "Efficient Delivery of Sticky siRNA and Potent Gene Silencing in aProstate Cancer Model Using a Generation 5 Triethanolamine-Core PAMAM Dendrimer," Mol Pharmaceutics 9:470-481 (Mar. 2012).

Lutolf et al., Synthesis and physicochemical characterization of end-linked poly(ethylene glycol)-co-peptide hydrogels formed by Michael-type addition. Biomacromolecules 4:713-722 (2003).

Martens et al., Tailoring the degradation of hydrogels formed from multivinyl poly(ethylene glycol) and poly(vinyl alcohol) macromers for cartilage tissue engineering. Biomacromolecules 4:283-292 (2003).

Martin et al., Human embryonic stem cells express an immunogenic nonhuman sialic acid. Nat Med 11:228e32 (2005).

McCall et al., Update on islet transplantation. Cold Spring Harb Perspect Med 2:a007823 (2012).

Merkel et al., "Molecular modeling and in vivo imaging can identify successful flexible triazine dendrimer-based siRNA delivery systems," J Control Release 153(1):23-33 (2011).

Metters et al., Network formation and degradation behavior of hydrogels formed by Michael-type addition reactions Biomacromolecules 6:290-301 (2005).

Metzke et al. A novel carbohydrate-derived side-chain polyether with excellent protein resistance. J. Am. Chem. Soc. 125:7760-7761 (2003).

Metzke et al., Structure-property studies on carbohydrate-derived polymers for use as protein-resistant biomaterials. Biomacromolecules 9:208-215 (2008).

Negishi et al., Luminescence technology in preservation and transplantation for rat islet. Islets 2011;3:111e7 (2011).

Nguyen et al., "Polymeric Materials for Gene Delivery and DNA Vaccination," Adv Mater 21:847-867 (2009).

Nguyen et al., "Nucleic acid delivery: the missing pieces of the puzzle?," Acc Chem Res 45:1153-1162 (Jul. 2012).

Nie et al., Production of heparin-containing hydrogels for modulating cell responses. Acta Biomater. 5:865-875 (2009).

Nikolova et al., The vascular basement membrane: a niche for insulin gene expression and beta cell proliferation. Dev Cell 10:397e405 (2006).

Nuttelman et al., Macromolecular monomers for the synthesis of hydrogel niches and their application in cell encapsulation and tissue engineering Prog. Polym. Sci. 33: 167-179 (2008).

Omori et al., Microassay for glucose-induced preproinsulin mRNA expression to assess islet functional potency for islet transplantation. Transplantation 89:146e54 (2010).

Paszek et al., Tensional homeostasis and the malignant phenotype. Cancer Cell 8:241-254 (2005).

Pavan et al., "Computational Insights into the Interactions between DNA and siRNA with "Rigid" and "Flexible" Triazine Dendrimers," Biomacromolecules 11: 721-730 (2010).

Pavan et al., "Dendrimers and dendrons for siRNA binding: computational insights," J Drug Deliv Sci Tec 22:83-89 (2012).

Peppas et al., Hydrogels in biology and medicine: from molecular principles to bionanotechnology AdV. Mater. 18:1345-1360 (2006).

Rackham et al., Co-transplantation of mesenchymal stem cells maintains islet organisation and morphology in mice. Diabetologia 54:1127-1135 (2011).

Rajeswari et al., "Does Tryptophan Intercalate in DNA? A Comparative Study of Peptide Binding to Alternating and Nonalternating A*T Sequences," Biochemistry 26:6825-6831 (1987).

Reed et al., In situ mechanical interferometry of matrigel films. Langmuir 25:36-39 (2009).

Rehfeldt et al., Cell responses to the mechanochemical microenvironment—implications for regenerative medicine and drug delivery. AdV. Drug DeliVery ReV. 59:1329-1339 (2007).

Rettig et al., "Progress Toward In Vivo Use of siRNAs-II," Mol Ther 20:483-512 (Mar. 2012).

Rizzi et al., Recombinant protein-co-PEG networks as cell-adhesive and proteolytically degradable hydrogel matrixes. Part I: Development and physicochemical characteristics. Biomacromolecules 6:1226-1238 (2005).

Salvay et al., Extracellular matrix protein-coated scaffolds promote the reversal of diabetes after extrahepatic islet transplantation. Transplantation 85:1456e64 (2008).

Schafer et al., "Redox environment of the cell as viewed through the redox state of the glutathione disulfide/glutathione couple," Free Rad. Biol. Med. 30:1191-1212 (2001).

Schaffer et al., "Molecular Engineering of Viral Gene Delivery Vehicles,"Annu Rev Biomed Eng 10:169-194 (2008).

Schense et al., Cross-linking exogenous bifunctional peptides into fibrin gels with factor XIIIa. Bioconjugate Chem. 10:75-81 (1999).

Seliktar D. Designing cell-compatible hydrogels for biomedical applications. Science 336:1124e8 (Jun. 15, 2012).

Silva et al., Selective differentiation of neural progenitor cells by high-epitope density nanofibers. Science 303:1352-1355 (2004).

Smith et al., "Diblock Glycopolymers Promote Colloidal Stability of Polyplexes and Effective pDNA and siRNA Delivery under Physiological Salt and Serum Conditions," Biomacromolecules 12:3015-3022 (2011).

(56) References Cited

OTHER PUBLICATIONS

Solon et al. Fibroblast adaptation and stiffness matching to soft elastic substrates. Biophys. J. 93:4453-4461 (2007).
Son et al., "Bioreducible Polymers for Gene Silencing and Delivery," J. Acc Chem Res 45:1100-1112 (2011).
Sonawane et al., "Chloride Accumulation and Swelling in Endosomes Enhances DNA Transfer by Polyamine-DNA Polyplexes," J Biol Chem 278:44826-44831 (2003).
Soofi et al., The elastic modulus of Matrigel as determined by atomic force microscopy. J. Struct. Biol. 167:216-219 (2009).
Stendahl et al., Extracellular matrix in pancreatic islets: relevance to scaffold design and transplantation. Cell Transplant 18:1e12 (2009).
Su et al., Anti-inflammatory peptide-functionalized hydrogels for insulin-secreting cell encapsulation. Biomaterials 31:308e14 (2010).
Akinc et al., "A combinatorial library of lipid-like materials for delivery of RNAi therapeutics," Nat Biotechnol 26:561-569 (2008).
Ashcroft et al., Glucose metabolism in mouse pancreatic islets. Biochem J 118:143e54 (1970).
Banerjee et al. The influence of hydrogel modulus on the proliferation and differentiation of encapsulated neural stem cells. Biomaterials 30:4695-4699 (2009).
Banwell et al., Rational design and application of responsive alpha-helical peptide hydrogels. Nat. Mater. 8:596-600 (2009).
Barnard et al., Degradable Self-Assembling Dendrons for Gene Delivery: Experimental and Theoretical Insights into the Barriers to Cellular Uptake J Am Chem Soc 133:20288-20300 (2011).
Behr, J. P., "Synthetic Gene Transfer Vectors II: Back to the Future," Acc Chem Res 45:980-984 (Feb. 2012).
Bennet et al., Incompatibility between human blood and isolated islets of Langerhans: a finding with implications for clinical intraportal islet transplantation? Diabetes 48:1907e14 (1999).
Blomeier et al. Polymer scaffolds as synthetic microenvironments for extrahepatic islet transplantation. Transplantation 82:452e9 (2006).
Borg et al., The use of biomaterials in islet transplantation. Curr Diab Rep 11:434e44 (2011).
Brown et al. Importance of hepatic portal circulation for insulin action in streptozotocin-diabetic rats transplanted with fetal pancreases. J Clin Invest 64:1688e94 (1979).
Bryant et al., Hydrogel properties influence ECM production by chondrocytes photoencapsulated in poly(ethylene glycol) hydrogels. J. Biomed. Mater. Res. 59:63-72 (2002).
Bryant et al., Incorporation of tissue-specific molecules alters chondrocyte metabolism and gene expression in photocrosslinked hydrogels. Acta Biomater. 1:243-252 (2005).
Burdick et al. Photoencapsulation of osteoblasts in injectable RGD-modified PEG hydrogels for bone tissue engineering Biomaterials 23:4315-4323 (2002).
Burdick et al. Controlled degradation and mechanical behavior of photopolymerized hyaluronic acid networks. Biomacromolecules 6:386-391 (2005).
Burnett et al., "RNA-based Therapeutics—Current Progress and Future Prospects," J. Chem Biol 19:60-71 (Jan. 2012).
Carlsson et al., Markedly decreased oxygen tension in transplanted rat pancreatic islets irrespective of the implantation site. Diabetes 50:489e95 (2001).
Chawla et al., Biodegradable and biocompatible synthetic saccharide-Peptide hydrogels for three-dimensional stem cell culture. Biomacromolecules 12:560e7 (2011).
Chawla et al., Modulation of chondrocyte behavior through tailoring functional synthetic saccharide-peptide hydrogels. Biomaterials 33:6052e60 (Sep. 1, 2012).
Chen et al., "Bioreducible Hyperbranched Poly(amido amine)s for Gene Delivery," Biomacromolecules 10:2921-2927 (2009).
Creusat et al., "Self-Assembling Polyethylenimine Derivatives Mediate Efficient siRNA Delivery in Mammalian Cells," Chembiochem 9:2787-2789 (2008).
Crombez et al., "Targeting cyclin B1 through peptide-based delivery of siRNA prevents tumour growth," Nucleic Acids Res 37(14):4559-4569 (2009).

Cui et al., "Conjugation Chemistry through Acetals toward a Dextran-Based Delivery System for Controlled Release of siRNA," J Am Chem Soc 134:15840 (Sep. 2012).
Davis et al., "Evidence of RNAi in humans from systemically administered siRNA via targeted nanoparticles," Nature 464:1067-1071 (2010).
Deforest et al., S. Sequential click reactions for synthesizing and patterning three-dimensional cell microenvironments. Nat. Mater. 8:659-664 (2009).
Degoricija et al., Hydrogels for osteochondral repair based on photocrosslinkable carbamate dendrimers. Biomacromolecules 9:2863-2872 (2008).
Discher et al., Tissue cells feel and respond to the stiffness of their substrate. Science 310:1139-1143 (2005).
Drury et al., Hydrogels for tissue engineering: scaffold design variables and applications. J. Biomaterials 24:4337-4351 (2003).
Dunn et al., "Reductively-responsive siRNA-conjugated hydrogel nanoparticles for gene silencing," J Am Chem Soc 134:7423-7430 (May 2012).
Economic costs of diabetes in the U.S. in 2007. Diabetes Care 31:596e 615 (2008).
Elbert et al., Conjugate addition reactions combined with free-radical cross-linking for the design of materials for tissue engineering. Biomacromolecules 2:430-441 (2001).
Engler et al., Matrix elasticity directs stem cell lineage specification. Cell 126:677-689 (2006).
Fischer et al., "Dendritic Polyglycerols with Oligoamine Shells Show Low Toxicity and High siRNA Transfection Efficiency in Vitro," Bioconjug Chem 21:1744-1752 (2010).
Flanagan et al., Neurite branching on deformable substrates. NeuroReport 13: 2411-2415 (2002).
Frisch et al., Anoikis mechanisms. Curr Opin Cell Biol 13:555e62 (2001).
Gelain et al., Designer self-assembling peptide nanofiber scaffolds for adult mouse neural stem cell 3-dimensional cultures. S. PLoS One 1:e119 (2006).
Grieshaber et al., Synthesis and Characterization of Elastin-Mimetic Hybrid Polymers with Multiblock, Alternating Molecular Architecture and Elastomeric Properties. Macromolecules 42:2532-2541(2009).
Guilak et al., Control of stem cell fate by physical interactions with the extracellular matrix. Cell Stem Cell 5, 17-26 (2009).
Haines-Butterick et al., Controlling hydrogelation kinetics by peptide design for three-dimensional encapsulation and injectable delivery of cells. Proc. Natl. Acad. Sci. U.S.A. 104:7791-7796 (2007).
Hiemstra et al., Rapidly in situ forming biodegradable robust hydrogels by combining stereocomplexation and photopolymerization. J. Am. Chem. Soc. 129:9918-9926 (2007).
Hu et al., Rational design of transglutaminase substrate peptides for rapid enzymatic formation of hydrogels. J. Am. Chem. Soc. 125, 14298-14299 (2003).
Hu et al., Hydrogels cross-linked by native chemical ligation. Biomacromolecules 2194-2200 (2009).
Hwang et al., Cartilage tissue engineering: Directed differentiation of embryonic stem cells in three-dimensional hydrogel culture. J. Methods Mol. Biol. 407:351-373 (2007).
Ingber et al., Cell structure and hierarchical systems biology. J. Cell Sci. 116:1157-1173 (2003).
Inukai et al., Preparation and characterization of hyaluronate-hydroxyethyl acrylate blend hydrogel for controlled release device. Chem. Pharm. Bull. 48:850-854 (2000).
Jun et al., Biomimetic self-assembled nanofibers Soft Matter 2:177-181 (2006).
Kersey et al., A hybrid polymer gel with controlled rates of cross-link rupture and self-repair J. R. Soc. Interface 4:373-380 (2007).
Kim et al., "Polyoxalate Nanoparticles as a Biodegradable and Biocompatible Drug Delivery Vehicle," Biomacromolecules 11: 555-560 (2010).
Kim et al., "Dendronized gold nanoparticles for siRNA delivery," Small 8:3253-3256 (Nov. 2012).

(56) References Cited

OTHER PUBLICATIONS

Kleinman et al., Isolation and characterization of type IV procollagen, laminin, and heparan sulfate proteoglycan from the EHS sarcoma. Biochemistry 21:6188-6193 (1982).
Kopecek, Hydrogel Biomaterials: A Smart Future? J. Biomaterials 28:5185-5192 (2007).

* cited by examiner

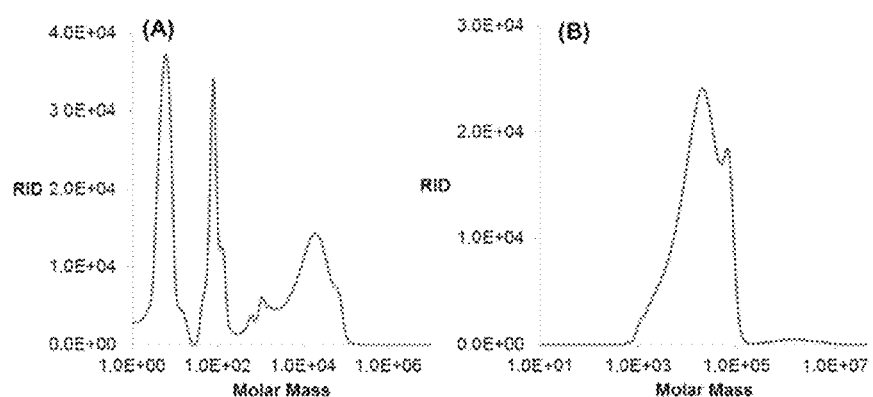
FIGURE 3A-B
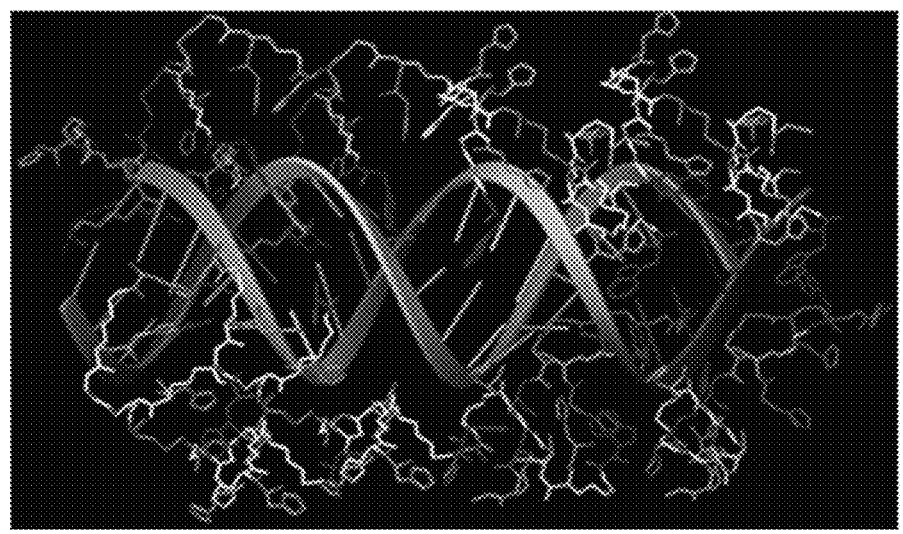
FIGURE 4

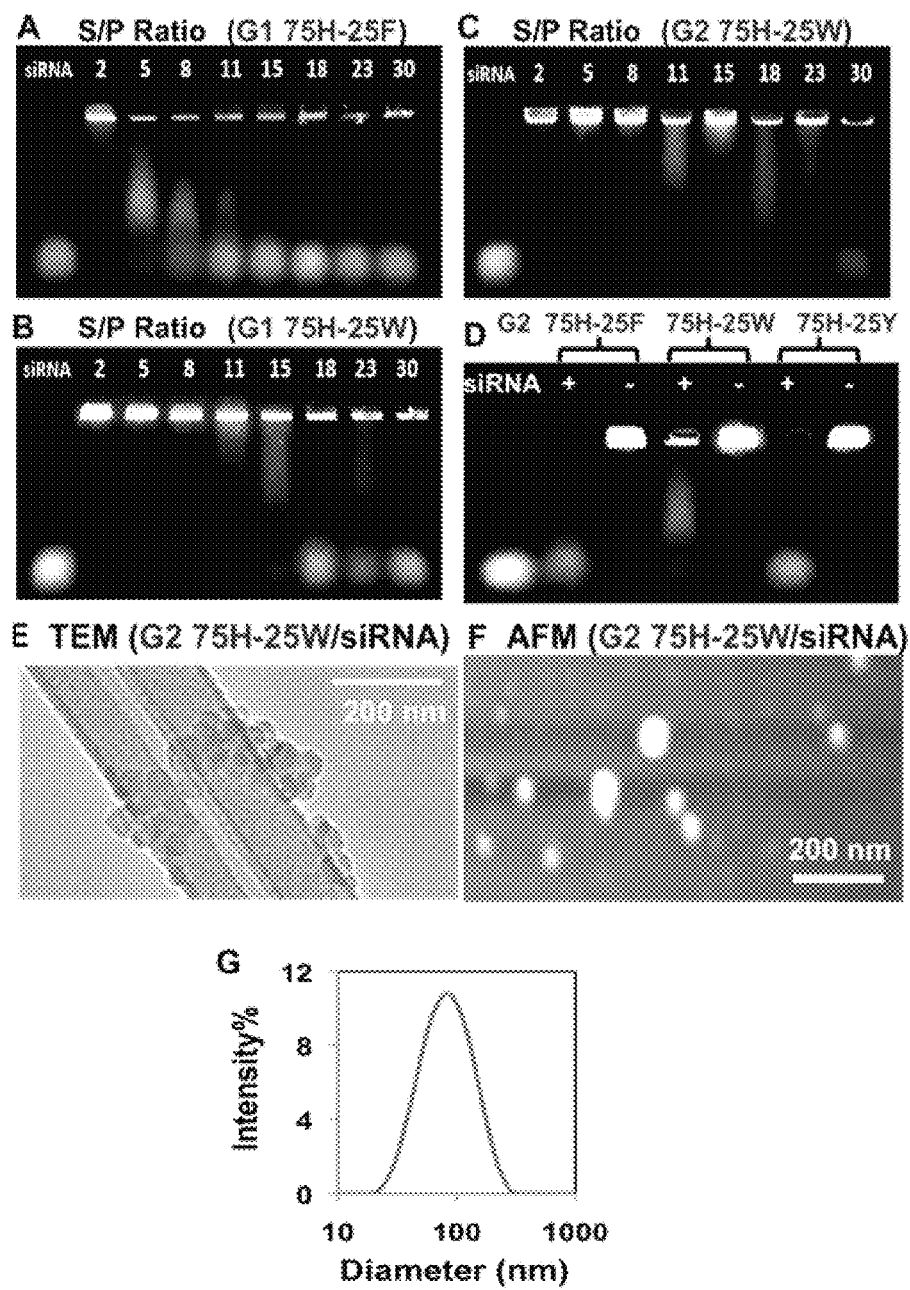
FIGURE 7A-G

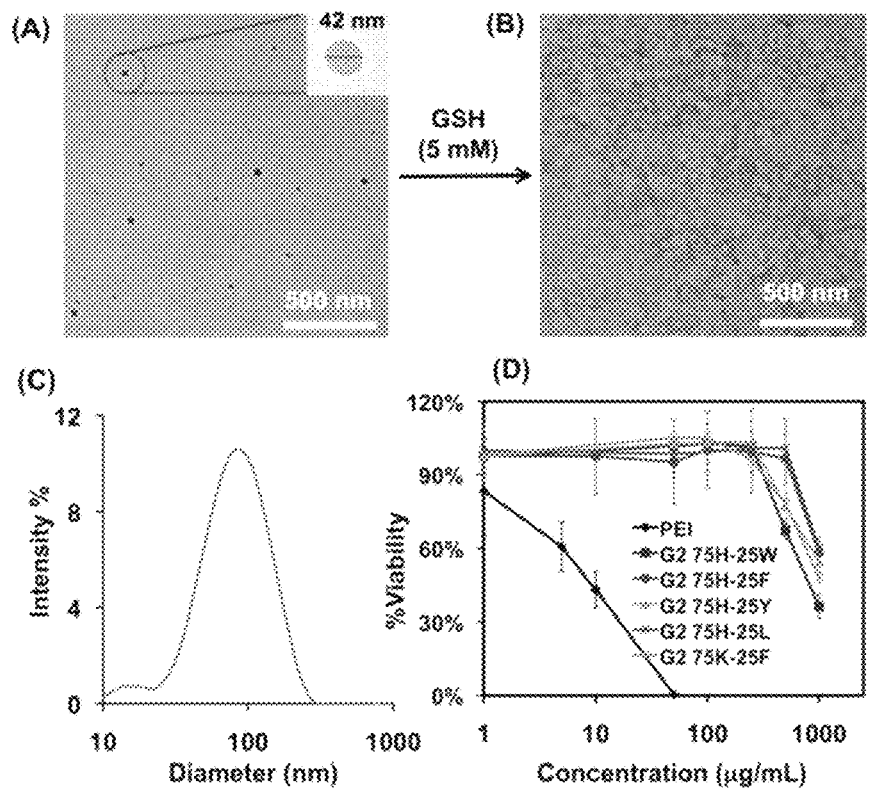
FIGURE 12A-D
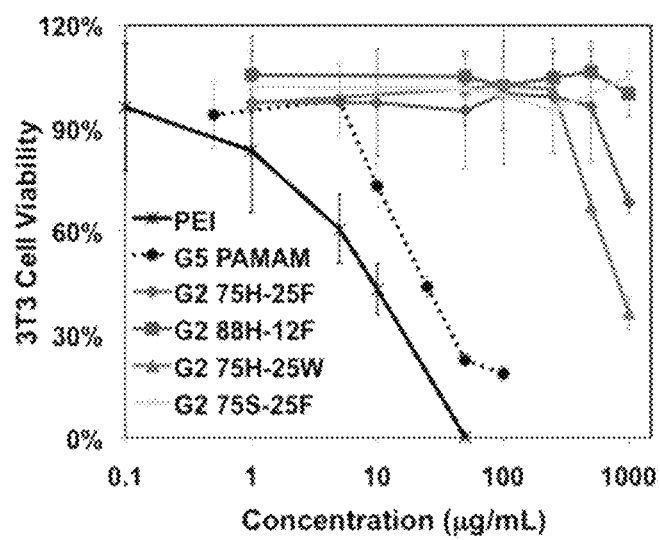
FIGURE 13

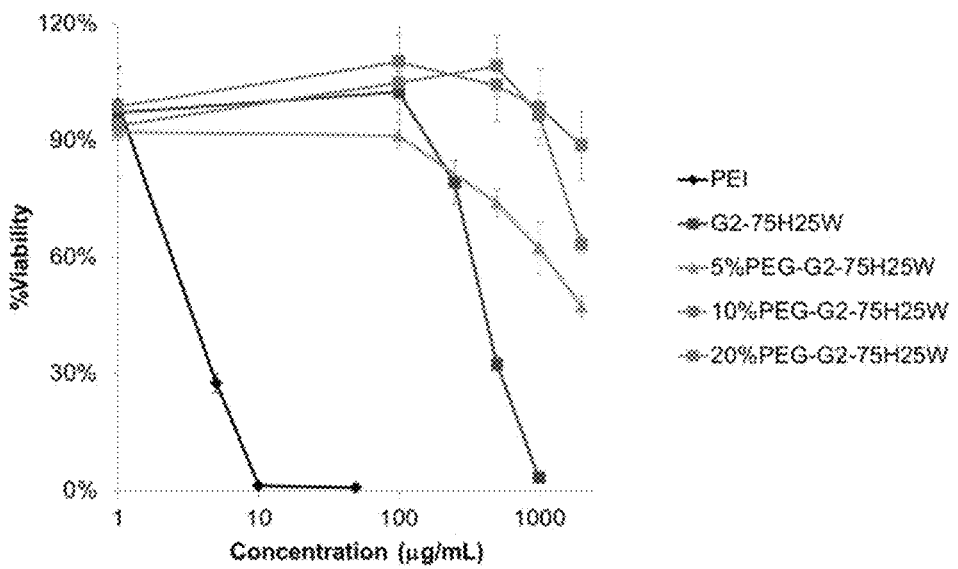
FIGURE 17
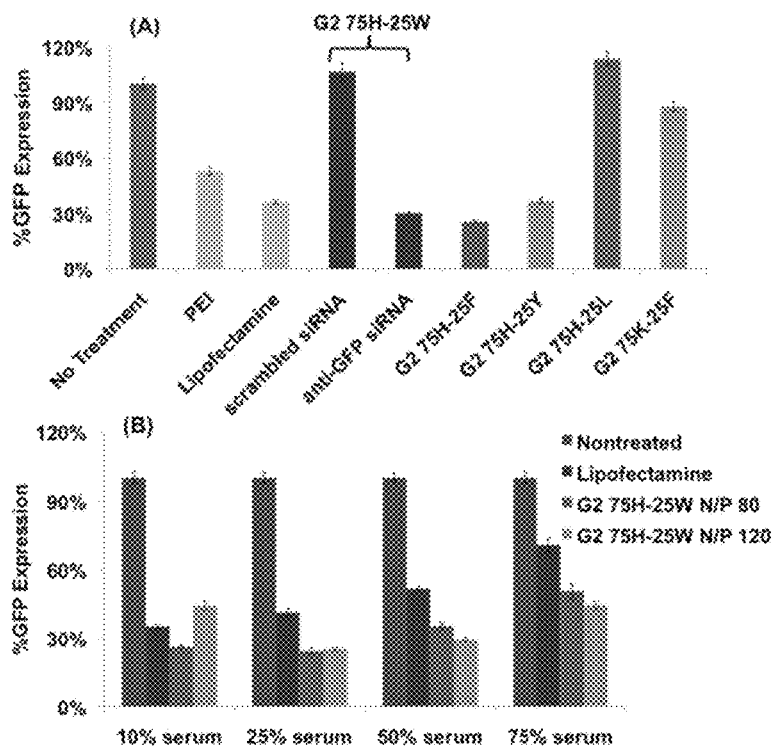
FIGURE 18A-B

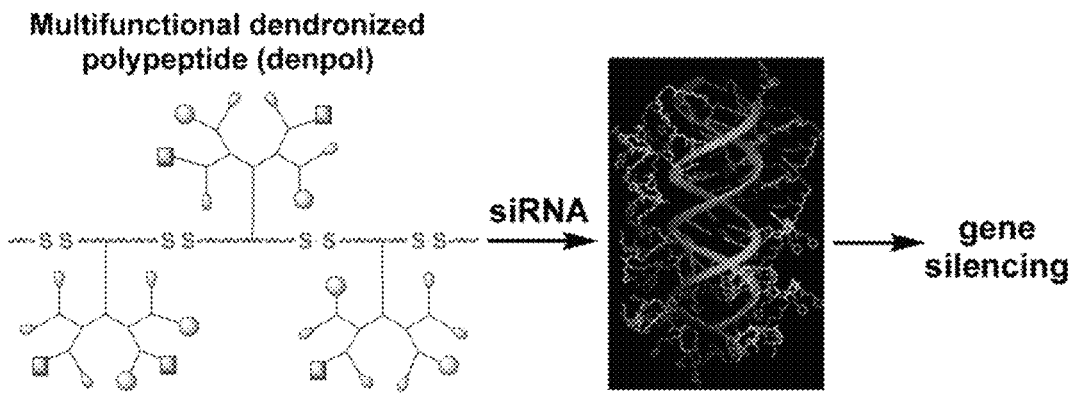
FIGURE 23
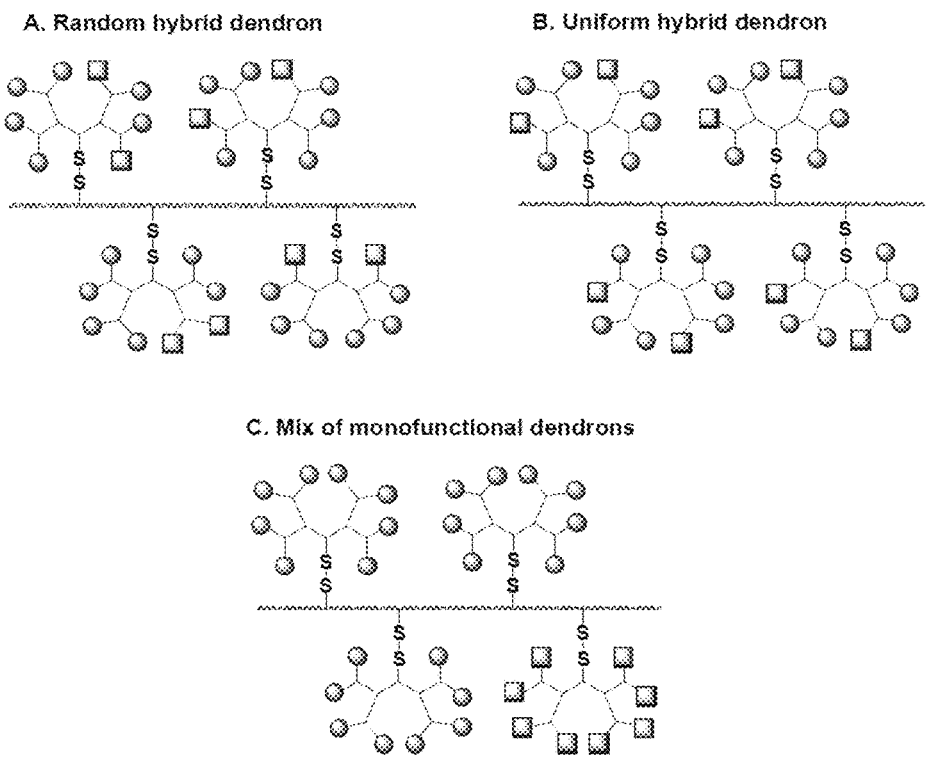
FIGURE 24A-C

DENDRONIZED POLYMERS FOR NUCLEIC ACID DELIVERY

CROSS REFERENCE TO RELATED APPLICATIONS

This application is a continuation application of U.S. application Ser. No. 14/221,249, filed Mar. 20, 2014 (now U.S. Pat. No. 9,745,421), which claims priority under 35 U.S.C. § 119 from Provisional Application Ser. No. 61/803,784 filed Mar. 20, 2013, the disclosures of which are incorporated herein by reference.

GOVERNMENT LICENSE RIGHTS

This invention was made with Government support under Grant No. DMR-0907688, awarded by the National Science Foundation. The Government has certain rights in the invention.

TECHNICAL FIELD

The disclosure provides for dendronized polymers, and the use of the polymers as carriers for the intracellular delivery of nucleic acids.

BACKGROUND

RNAi has tremendous potential for therapeutic treatment. The lack of safe and efficient intracellular delivery of siRNA has significantly hampered the use of RNAi as a treatment option.

SUMMARY

The disclosure provides for an innovative biodegradable peptide-based dendronized polymer ("denpol") architecture that can be used as a carrier for the intracellular delivery of nucleic acids. The dendronized polymers disclosed herein combine the multivalency of dendrimers with the conformational flexibility of linear polymers for optimal binding of nucleic acids (e.g., siRNA). By incorporating multi-functional amino acids, the dendronized polymers of the disclosure were able to overcome various challenges that impeded the intracellular delivery of nucleic acids. Moreover, the dendronized polymers of disclosure have versatile structures that can be tuned both systematically and combinatorially so as to allow for the optimization of denpols for particular applications.

In the Examples provided herein, a focused library was screened and several denpols were identified that could effectively deliver siRNA into cells with minimal toxicity in vitro. Moreover, the denpols of the disclosure had significantly improved transfection efficiencies over Lipofectamine™ (i.e., cationic lipids) in serum-containing media. In fluorescence intracellular trafficking studies, it was determined that the amphiphilicity of the denpols facilitated both cellular uptake and endosomal escape. For example, it was found that denpols comprising histidine moieties exhibited a buffering capacity that promoted endosomal membrane rupture, thus enhancing transfection efficacy. The combination of high delivery efficiency in serum and low cytotoxicity demonstrates that the denpols of the disclosure are effective and safe carriers for the intracellular delivery of nucleic acids.

In particular embodiment, the disclosure provides for a dendronzied polymer comprising a highly branched and flexible architecture that is biocompatible and capable of forming a polyplex with nucleic acids and releasing the nucleic acids within a cell. In a further embodiment, the dendronzied polymer comprises the structure of Formula I:

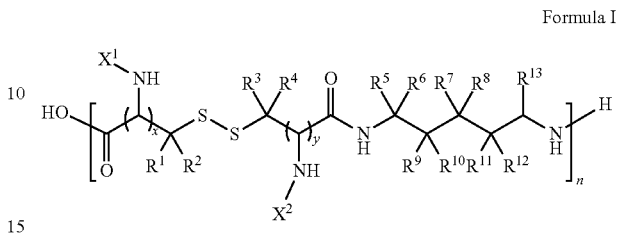

Formula I wherein, n is an integer greater than 50; x and y are in ratio from 1:99 to 99:1; $R^1$-$R^{12}$ are independently selected from H, optionally substituted ($C_{1-12}$)-alkyl, optionally substituted ($C_{1-12}$)-heteroalkyl, optionally substituted ($C_{1-12}$)-alkenyl, optionally substituted ($C_{1-12}$)-heteroalkenyl, optionally substituted ($C_{1-12}$)-alkynyl, optionally substituted ($C_{1-12}$)-heteroalkynyl, optionally substituted cycloalkyl, optionally substituted cycloalkenyl, halide, hydroxyl, ketone, aldehyde, acyl halide, carbonate, carboxylic acid, ester, ether, amide, amine, imine, azide, cyanate, azo, nitrate, nitrile, nitro, nitroso, thiol, sulfide, disulfide, sulfoxide, sulfone, sulfinic acid, sulfonic acid, thiocyanate, thione, thial, phosphine, phosphonic acid, phosphate, phosphodiester, boronic acid, boronic ester, borinic acid, and borinic ester; $R^{13}$ is an ester; $X^1$-$X^2$ are independently a polyoxyalkylene polymer or an optionally substituted L-lysine based dendron that is functionalized on the outer layer by comprising hydrophobic amino acids and hydrophilic amino acids; and wherein at least one of $X^1$-$X^2$ is an optionally substituted L-lysine based dendron. In yet further embodiment, $X^1$ has the structure of:

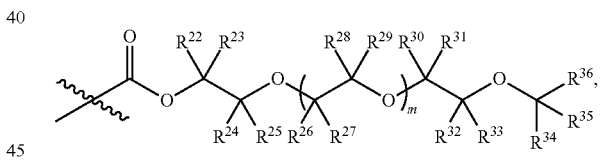

wherein, m is an integer greater than 100; and $R^{22}$-$R^{36}$ are independently selected from H, optionally substituted ($C_{1-6}$)-alkyl, optionally substituted ($C_{1-6}$)-heteroalkyl, optionally substituted ($C_{1-6}$)-alkenyl, optionally substituted ($C_{1-6}$)-heteroalkenyl, optionally substituted ($C_{1-6}$)-alkynyl, optionally substituted ($C_{1-6}$)-heteroalkynyl, optionally substituted cycloalkyl, optionally substituted cycloalkenyl, halide, hydroxyl, ketone, aldehyde, acyl halide, carbonate, carboxylic acid, ester, ether, amide, amine, imine, azide, cyanate, azo, nitrate, nitrile, nitro, nitroso, thiol, sulfide, disulfide, sulfoxide, sulfone, sulfinic acid, sulfonic acid, thiocyanate, thione, thial, phosphine, phosphonic acid, phosphate, phosphodiester, boronic acid, boronic ester, borinic acid, borinic ester, methacrylates, acrylates, maleimides, mesylates, N-hydroxysuccinimide (NHS) esters, reversible addition-fragmentation chain transfer (RAFT) groups, tosylates, and biotin.

In a certain embodiment, the disclosure further provides for a dendronized polymer comprising a structure of Formula I(a):

Formula I(a)

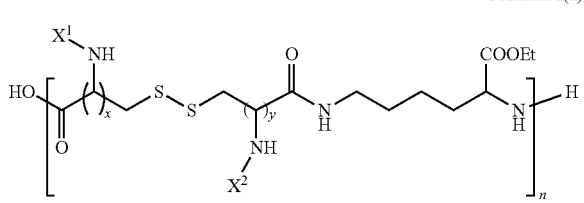

wherein, n is an integer greater than 100; x and y are in ratio from 1:99 to 99:1; and $X^1$-$X^2$ are optionally substituted L-lysine based dendrons that are functionalized on the outer layer by comprising hydrophilic-based amino acids and hydrophobic-based amino acids.

In another embodiment, the disclosure also provides for a dendronized polymer comprising a structure of Formula I(b):

Formula I(b)

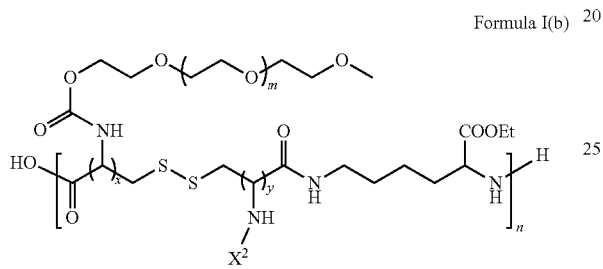

wherein, n is an integer greater than 100; m is an integer greater than 100; x and y are in ratio from 5:95 to 95:5; and $X^2$ is an optionally substituted L-lysine based dendron that is functionalized on the outer layer by comprising hydrophilic-based amino acids (e.g., lysine, serine, histidine, proline, arginine, asparagine, glutamic acid, and aspartic acid) and hydrophobic-based amino acids (e.g., tryptophan, phenylalanine, tyrosine, leucine, alanine, valine, isoleucine, methionine, and cysteine). In a further embodiment, the one or more L-lysine based dendrons comprise hydrophilic amino acids selected from lysine, histidine, and serine, and hydrophobic amino acids selected from phenylalanine, tryptophan, and tyrosine, in a molar ratio of 10:1 to 1:10 or a molar ratio of 4:1 to 1:4. In a particular embodiment, the disclosure for a polyoxyalkylene polymer selected from polyethylene glycol (PEG), PEG that has been functionalized with various functional groups or organic molecules, PEG diblock copolymers, PEG triblock copolymers, poly(ethylene glycol-ran-propylene glycol), and poly(ethylene glycol-ran-propylene glycol) monobutyl ether. In yet a further embodiment, the polyoxyalkylene polymer is PEG having a molecular weight between 4,000-10,000.

In a particular embodiment, the disclosure provides for a dendronized polymer comprising a structure of Formula IV:

Formula IV

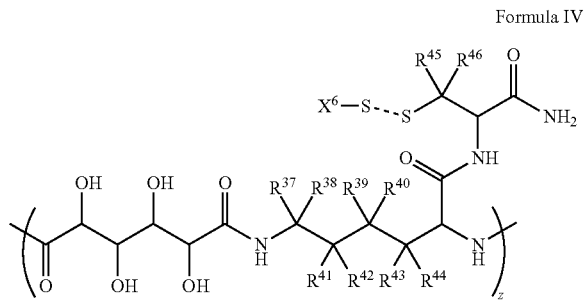

wherein, z is an integer greater than one; $R^{37}$-$R^{46}$ are each independently selected from H, optionally substituted $(C_{1-12})$-alkyl, optionally substituted $(C_{1-12})$-heteroalkyl, optionally substituted $(C_{1-12})$-alkenyl, optionally substituted $(C_{1-12})$-heteroalkenyl, optionally substituted $(C_{1-12})$-alkynyl, optionally substituted $(C_{1-12})$-heteroalkynyl, optionally substituted cycloalkyl, optionally substituted cycloalkenyl, halide, hydroxyl, ketone, aldehyde, acyl halide, carbonate, carboxylic acid, ester, ether, amide, amine, imine, azide, cyanate, azo, nitrate, nitrile, nitro, nitroso, thiol, sulfide, disulfide, sulfoxide, sulfone, sulfinic acid, sulfonic acid, thiocyanate, thione, thial, phosphine, phosphonic acid, phosphate, phosphodiester, boronic acid, boronic ester, borinic acid, and borinic ester; and $X^6$ is a dendron comprised of a plurality of linked amino acids that is attached to the polymer backbone via the sulfide linkage. In a further embodiment, $X^6$ is a dendron comprised of a plurality of linked amino acids having the structure of Formula III:

Formula III

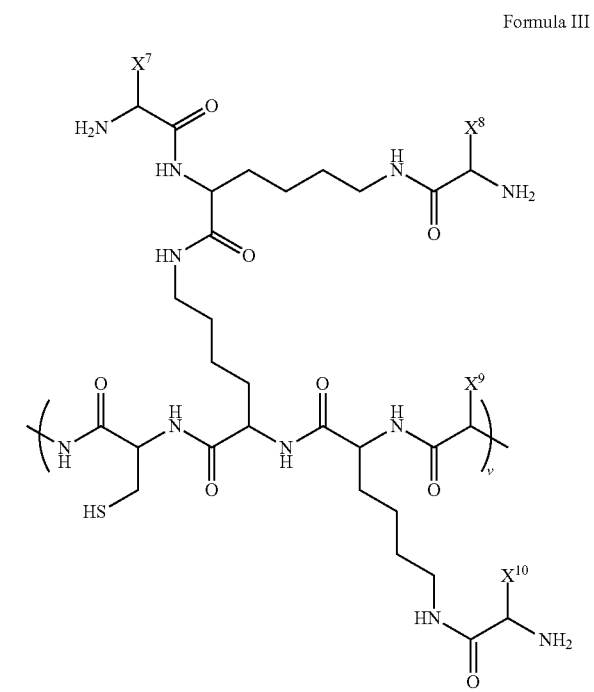

wherein, v is an integer greater than one; $X^7$-$X^{10}$ are each independently hydrophobic or hydrophilic amino acid side groups.

In a certain embodiment, the disclosure provides for dendronized polymer that further comprises a targeting ligand. Examples of targeting ligands include antibodies, aptamers, cholesterol and its derivatives, folate compounds or folate conjugates, transferrin, saccharides and cell-penetrating peptides.

In a particular embodiment, the disclosure further provides for a dendronized polymer disclosed herein which further comprises complexed oligonucleotides or polynucleotides. In a further embodiment, the complexed oligonucleotides are siRNA.

In a certain embodiment, the disclosure also provides for pharmaceutical composition comprising a dendronized polymer/siRNA polyplex.

In another embodiment, the disclosure provides for a method of siRNA to a cell in vitro or in vivo comprising contacting the cell with the pharmaceutical composition of the disclosure. In yet a further embodiment, oligonucleotide induces an RNAi response in the cell.

In a particular embodiment, the disclosure also provides for a method of treating a disease or disorder in a subject comprising administering a pharmaceutical composition disclosed herein. Examples of diseases or disorders includes diabetes; cancer; infectious and parasitic diseases; inflammatory diseases; neurodegenerative diseases; autoimmune diseases; respiratory diseases; endocrine diseases; eye diseases; intestinal diseases; cardiovascular diseases; idiopathic diseases; genetic disorders; growth disorders; congenital disorders; mental or behavioral disorders; adrenal disorders; thyroid disorders; calcium homeostasis disorders; pituitary gland disorders; and sex hormone disorders.

DESCRIPTION OF DRAWINGS

FIG. 3A-B provides a gel permeation chromatography ("GPC") trace of a denpol backbone before (A) and after (B) purification.

FIG. 4 presents a computer generated image of denpol-nucleic acid polyplex. Multivalent charge and hydrophobic intercalation lead to stable polyplex formation, but exposure to a reductive environment leads to the release of the nucleic acid. (Color code: red=$NH_2$, green=His, blue=Trp).

FIG. 7A-G provides images from a gel electrophoresis study of denpol/siRNA complexation. (A)-(C) Dextran sulfate competition with different siRNA/denpol polyplexes prepared at N/P 40: (A) G1 75H-25F, (B) G2 75H-25F, (C) G2 75H-25W. (D) siRNA release from polyplexes prepared at N/P 40 after the treatment of GSH (5 mM) at r.t. for 30 min ("+": treated with GSH; "−": control). (E) Transmission electron microscope images of G2 75H-25W/siRNA polyplex. (F) Atomic force microscope image of G2 75H-25W/siRNA polyplexes. (G) Dynamic light scattering ("DLS") measurement of G2 75K-25F/siRNA polyplex.

FIG. 12A-D characterizes the denpol/siRNA polyplexes of the disclosure. TEM images of siRNA and G2 75H-25W polyplexes at N/P 10 before (A) and after (B) glutathione treatment. (C) Size distribution measured by DLS for G2 75H-25W/siRNA polyplexes at N/P 40. (D) MTT assay of selected denpols using the NIH 3T3 cell line.

FIG. 13 presents an MTT assay of selected denpols using the NIH 3T3 cell line.

FIG. 17 presents MTT cytotoxicity assays of different PEGylated denpols.

FIG. 18A-B provides flow cytometry analysis of transfected NIH 3T3 cells. (A) Transfection summary of selected G2 denpols at optimal N/P ratio in serum free media. (G2 75H-25W and 75K-25F were transfected at N/P 80 and the rest at N/P 120). (B) Comparison of in vitro transfection efficacy between Lipofectamine® and G2 75H-25W at different serum concentration.

FIG. 23 provides a schematic of the process used to deliver siRNA to silence gene expression using the multifunctional dendronized polypeptide polymers of the disclosure.

FIG. 24A-C provides for three variations of the spatial arrangement of dendron functional groups. (A) Examples of dendrons in which different functional groups (indicated by a circle or a square) are distributed randomly on the outer layer of the dendron. (B) Examples of dendrons in which different functional groups (indicated by a circle or a square) are distributed uniformly on the outer layer of the dendrons. (C) Examples of dendrons in which a portion of the dendrons comprise one type of functional group (indicated by a circle), and another portion of dendrons which comprise one type, but different functional group (indicated by a square).

DETAILED DESCRIPTION

As used herein and in the appended claims, the singular forms "a," "an," and "the" include plural referents unless the context clearly dictates otherwise. Thus, for example, reference to "a dendronized polymer" includes a plurality of such dendronized polymers and reference to "the amino acid" includes reference to one or more amino acids and equivalents thereof known to those skilled in the art, and so forth.

Unless defined otherwise, all technical and scientific terms used herein have the same meaning as commonly understood to one of ordinary skill in the art to which this disclosure belongs. Although many methods and reagents are similar or equivalent to those described herein, the exemplary methods and materials are disclosed herein.

All publications mentioned herein are incorporated by reference in full for the purpose of describing and disclosing methodologies that might be used in connection with the description herein. The publications are provided solely for their disclosure prior to the filing date of the present application. Nothing herein is to be construed as an admission that the inventors are not entitled to antedate such disclosure by virtue of prior disclosure. Moreover, with respect to any term that is presented in one or more publications that is similar to, or identical with, a term that has been expressly defined in this disclosure, the definition of the term as expressly provided in this disclosure will control in all respects.

RNA interference (RNAi) presents tremendous potential as a new approach in gene therapy. Particularly, small interference RNAs (siRNAs) has become promising candidates for clinical applications because of their capability to selectively silence the encoded protein expression. Since its discovery, a number of siRNA gene silencing based treatments has reached clinical trials, and the therapeutic potential of siRNA for a variety of diseases including cancer, diabetes, and neurodegenerative diseases have been demonstrated using cell culture as well as animal models. Despite its potential, therapeutic application of siRNA is greatly hindered by the lack of safe and effective delivery agents. Both viral and non-viral delivery agents have been studied extensively in the last decades. Viral based vectors, although having a higher efficiency in general, have safety concerns due to their infectious nature and immunogenicity. On the other hand, synthetic non-viral delivery agents offer versatile and precise structure control and present as promising candidates for siRNA delivery. Of these agents, the most common siRNA delivery agents include cationic lipids, polymers, dendrimers, peptides and nanoparticles. However, many of these agents suffer from low efficiencies, high toxicities, and/or are immunogenic in vivo. Accordingly, very few of these agents have progressed into clinical trials and none have been approved.

Figure 1:
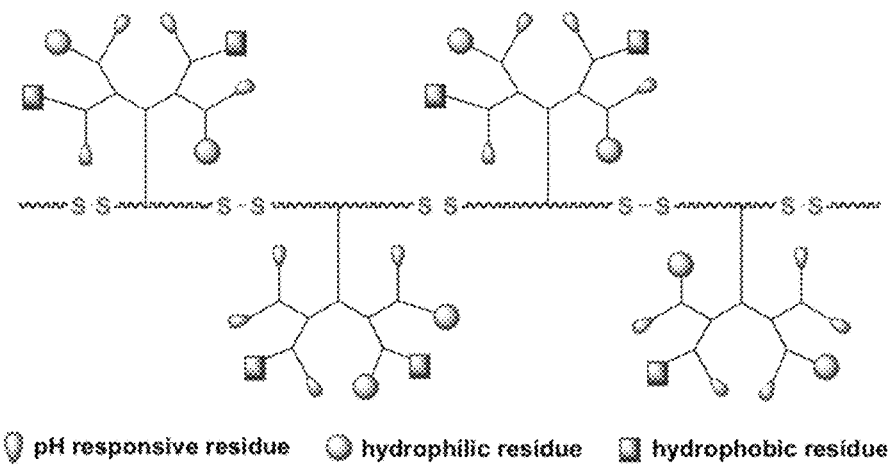
FIG. 1 illustrates one embodiment of a generalized architecture of a multifunctional amphiphilic dendronized polymer disclosed herein.
Figure 2:
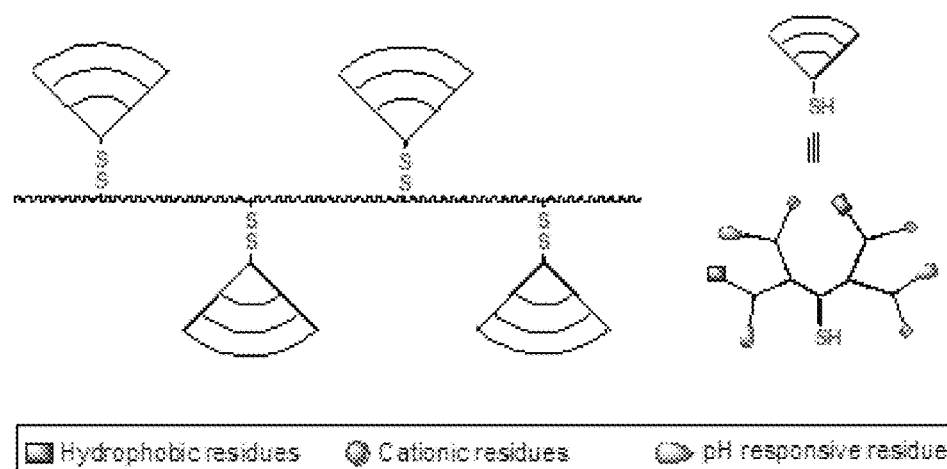
FIG. 2 illustrates another embodiment of a generalized architecture of a multifunctional amphiphilic dendronized polymer disclosed herein.
Figure 5:
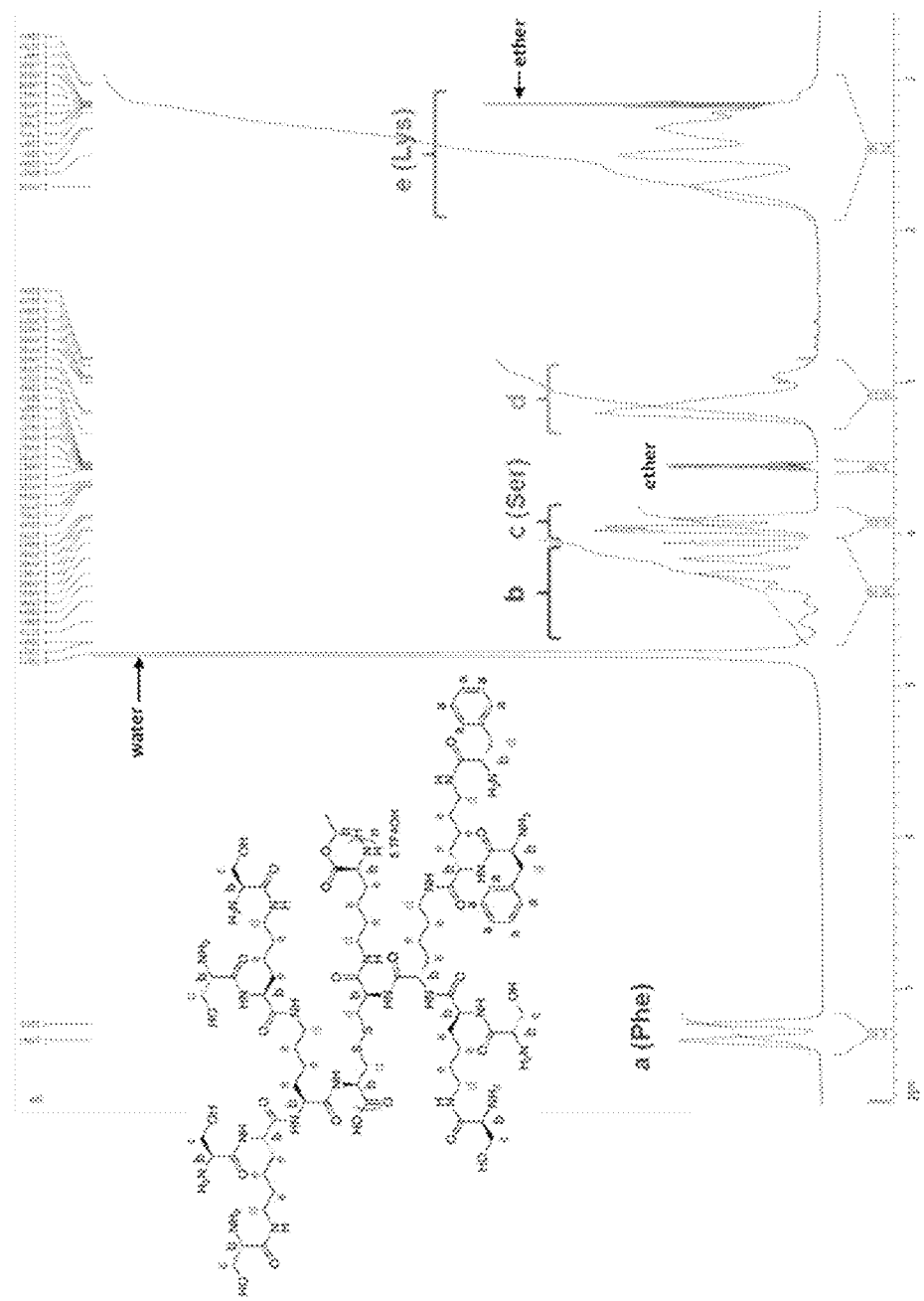
FIG. 5 provides a representative $^1H$ NMR peak assignment (right) of a functionalized denpol (G2 75S-25F (left)) of the disclosure.

The disclosure provides for nucleic acid delivery system comprising dendronized polymers. The dendronized polymers (denpols) disclosed herein are characterized by the following features: (1) the denpols are able to form stable polyplexes with nucleic acids, (2) the denpol/siRNA polyplexes are able to efficiently transport across cell membrane, (3) the internalized polyplexes must be able to efficiently escape the endosome before lysosomal degradation, and (4) the nucleic acid cargo must be able to efficiently dissociate from the delivery vector in cytosol. The dendronized polymers of the disclosure were found to be (1) non-toxic and non-immunogenic, (2) do not negatively interact with blood components, (3) exhibit desirable pharmacokinectics, and (4) are able to penetrate tissues to deliver to the target site. The dendronized polymers disclosed herein are able to provide all these features and characteristics by (1) having a highly branched architecture; and (2) having chain flexibility (e.g., see FIG. 1 and FIG. 2). In a particular embodiment, the disclosure also provides that a dendronized polymer of the disclosure can comprise amphiphilic moieties which help both cellular uptake and endosomal escape by enhancing membrane permeability. In a further embodiment, a dendronized polymer of the disclosure comprises pH responsive moieties which can facilitate endosomal membrane rupture through a "proton sponge" effect and/or increasing amphiphilicity at lower pHs. In yet a further embodiment, the disclosure provides that a dendronized polymer of the disclosure comprises disulfide bonds which allow for dissociation of the siRNA in a reducing environment (i.e., in the cytoplasm of a cell).

Accordingly, the disclosure provides for innovative biodegradable dendronized polymers ("denpols") that effectively deliver nucleic acids (e.g., siRNA) into cells. By contrast to the teachings of the art, which include studies that indicate that high generation dendrimers cannot effectively bind and deliver siRNAs intracellularly, and low generation dendrimers which lack the multivalency for strong siRNA binding, the dendronized polymers disclosed herein combine the mulivalency of dendrimers and conformational flexibility of linear polymers to effectively bind and deliver siRNA intracellularly. Furthermore, the disclosure provides methods to make the dendronized polymers disclosed herein that allow for structural permutation and optimization. In a particular embodiment, the disclosure provides for a dendronzied polymer which comprises a highly branched and flexible architecture that is biocompatible and capable of forming polyplexes with nucleic acids and releasing the nucleic acids within a cell. In a further embodiment, a dendronized polymer disclosed herein is fully composed of natural amino acids so as to ensure biodegradability and low toxicity.

It should be understood, however, the disclosure does not simply provide for dendronized polymers based only on the following presented structural Formulas, but also includes dendronized polymers that are comprised of different polymer backbones and which can contain non-peptide dendrons. Therefore, the dendronized polymers disclosed herein are not limited to the exemplified structures presented herein, but include any structure characterized by the following: a non-toxic and non-immunogenic polymer that (1) has a highly branched architecture and (2) has chain flexibility, and which is further capable of forming polyplexes with nucleic acids and is then able to release these nucleic acids within a cell. For example, the dendronized polymers disclosed herein may comprise sugar moieties or a combination of sugar moieties and amino acid moieties.

In a particular embodiment, the disclosure provides for a dendronized polymer comprising the structure of Formula I:

Formula I

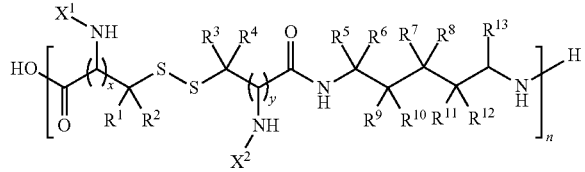

wherein,
n is an integer greater than 1;
x and y are in ratio from 1:99 to 99:1;
$R^1$-$R^{12}$ are independently selected from the group comprising H, optionally substituted ($C_{1-12}$)-alkyl, optionally substituted ($C_{1-12}$)-heteroalkyl, optionally substituted ($C_{1-12}$)-alkenyl, optionally substituted ($C_{1-12}$)-heteroalkenyl, optionally substituted ($C_{1-12}$)-alkynyl, optionally substituted ($C_{1-12}$)-heteroalkynyl, optionally substituted cycloalkyl, optionally substituted cycloalkenyl, halide, optionally substituted oxygen containing functional group (e.g., alcohol, ketone, aldehyde, acyl halide, carbonate, carboxylic acid, ester, and ether), optionally substituted nitrogen containing functional group (e.g., amide, amine, imine, azide, cyanate, azo, nitrate, nitrile, nitro, and nitroso), optionally substituted sulfur containing functional group (e.g., thiol, sulfide, disulfide, sulfoxide, sulfone, sulfinic acid, sulfonic acid, thiocyanate, thione, and thial), optionally substituted phosphorous containing functional group (e.g., phosphine, phosphonic acid, phosphate, phosphodiester), optionally substituted boron containing functional group (e.g., boronic acid, boronic ester, borinic acid, and borinic ester);

$R^{13}$ is an ester;

$X^1$-$X^2$ are independently a polyoxyalkylene polymer or an optionally substituted amino acid based dendron that is functionalized on the outer layer by comprising two different optionally substituted amino acids; and wherein at least one of $X^1$-$X^2$ is an optionally substituted amino acid based dendron.

In a particular embodiment, n is an integer greater than 10, 50, 100, 500, 1000, 5000, 10000, 15000, or 20000.

In a further embodiment, the disclosure provides for a dendronized polymer comprising the structure of Formula I:

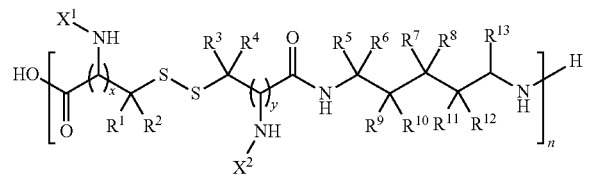

Formula I wherein,
n is an integer greater than 50;
x and y are in ratio from 1:99 to 99:1;
$R^1$-$R^{12}$ are independently selected from the group comprising H, optionally substituted ($C_{1-12}$)-alkyl, optionally substituted ($C_{1-12}$)-heteroalkyl, optionally substituted ($C_{1-12}$)-alkenyl, optionally substituted ($C_{1-12}$)-heteroalkenyl, optionally substituted ($C_{1-12}$)-alkynyl, optionally substituted ($C_{1-12}$)-heteroalkynyl, optionally substituted cycloalkyl, optionally substituted cycloalkenyl, halide, optionally substituted oxygen containing functional group (e.g., alcohol, ketone, aldehyde, acyl halide, carbonate, carboxylic acid, ester, and ether), optionally substituted nitrogen containing functional group (e.g., amide, amine, imine, azide, cyanate, azo, nitrate, nitrile, nitro, and nitroso), optionally substituted sulfur containing functional group (e.g., thiol, sulfide, disulfide, sulfoxide, sulfone, sulfinic acid, sulfonic acid, thiocyanate, thione, and thial), optionally substituted phosphorous containing functional group (e.g., phosphine, phosphonic acid, phosphate, phosphodiester), optionally substituted boron containing functional group (e.g., boronic acid, boronic ester, borinic acid, and borinic ester);

$R^{13}$ is an ester;

$X^1$-$X^2$ are independently a polyoxyalkylene polymer or an optionally substituted L-lysine based dendron that is functionalized on the outer layer by comprising hydrophobic amino acids and hydrophilic amino acids; and wherein at least one of $X^1$-$X^2$ is an optionally substituted L-lysine based dendron.

Examples of hydrophilic-based amino acids include, but are not limited to, lysine, serine, histidine, proline, arginine, asparagine, glutamic acid, and aspartic acid.

Examples of hydrophobic-based amino acids include, but are not limited to, tryptophan, phenylalanine, tyrosine, leucine, alanine, valine, isoleucine, methionine, and cysteine.

Examples of polyoxyalkylene polymers, include but are not limited to: polyethylene glycol (PEG); PEG which has been functionalized with various functional groups or organic molecules, including: halides, acetylenes, amines, azides, hydroxyls, thiols, methacrylates, acrylates, carboxylic acids, maleimides, mesylates, NHS esters, RAFT groups, tosylates, biotin or any combination of the foregoing; PEG diblock copolymers, including PEG-PLA, PEG-PLGA, PEG-PCL, PEG-PE, and PEG-PS; PEG triblock copolymers, including PEG-PPG-PEG, PPG-PEG-PPG, PLA-PEG-PLA, PLGA-PEG-PLGA, and PLCL-PEG-PLCL; poly(ethylene glycol-ran-propylene glycol); and poly(ethylene glycol-ran-propylene glycol) monobutyl ether. Most if not all of these polyoxyalkylene polymers are commercially available from various vendors, such as Sigma-Aldrich (St. Louis, Mo.). Furthermore, a person of ordinary skill in the art would recognize that these polymers can readily be incorporated into synthesis methods presented herein (e.g., SCHEME 6) to produce a denpol of the disclosure (e.g., a polyoxyalkylene-denpol). Additionally, these polyoxyalkylene polymers come in various molecular weights and it is fully contemplated by this disclosure that any molecular size polyoxyalkylene polymer can be used to make a dendronized polymer of the disclosure. For example, PEG having an average molecular weight of about 200, about 300, about 400, about 600, about 1000, about 1450, about 1500, about 2000, about 3000, about 3350, about 4000, about 4600, about 5000, about 6000, about 8000, about 10000, about 12,000, about 20,000, about 35,000, or in a range between any two of the foregoing, can all be used in the synthesis of a denpol of the disclosure.

In a one embodiment, $X^1$-$X^2$ comprise optionally substituted L-lysine based dendron that is functionalized on the outer layer by comprising a ratio of optionally substituted hydrophilic amino acids and optionally substituted hydrophobic amino acids. In a particular embodiment, a dendronized polymer disclosed herein is functionalized with a ratio of hydrophilic-based amino acids to hydrophobic-based amino acids in the range of 20:1 to 1:20; 15:1 to 15:1; 10:1 to 1:10; 9:1 to 1:9, 8:1 to 1:8; 7:1 to 1:7, 6:1 to 1:6, 5:1 to 1:5; 4:1 to 1:4; 3:1 to 1:3; 3:2 to 2:3; 2:1 to 1:2; 1.5:1 to 1:1.5; or about 1:1. In a further embodiment, a dendronized polymer disclosed herein is functionalized with a ratio of a first amino acid selected from lysine, histidine, and serine, to a second amino acid selected from phenylalanine, tryptophan, tyrosine, and leucine, wherein the ratio to the first amino acid to the second amino acid is in the range of 20:1 to 1:20; 15:1 to 15:1; 10:1 to 1:10; 9:1 to 1:9, 8:1 to 1:8; 7:1 to 1:7, 6:1 to 1:6, 5:1 to 1:5; 4:1 to 1:4; 3:1 to 1:3; 3:2 to 2:3; 2:1 to 1:2; 1.5:1 to 1:1.5; or about 1:1. In one embodiment, a dendronized polymer disclosed herein is functionalized with a ratio of histidine to tryptophan in the range of 5:1 to 1:5; 4:1 to 1:4; 3:1 to 1:3; 3:2 to 2:3; 2:1 to 1:2; 1.5:1 to 1:1.5; or about 1:1.

In a further embodiment, the disclosure provides for a L-lysine based dendron comprising the structure of Formula II:

Formula II

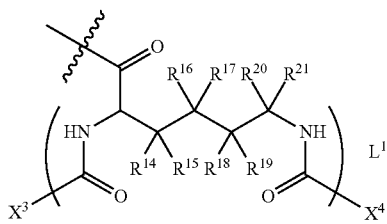

wherein, $R^{14}$-$R^{21}$ are independently selected from the group comprising H, optionally substituted ($C_{1-6}$)-alkyl, optionally substituted ($C_{1-6}$)-heteroalkyl, optionally substituted ($C_{1-6}$)-alkenyl, optionally substituted ($C_{1-6}$)-heteroalkenyl, optionally substituted ($C_{1-6}$)-alkynyl, optionally substituted ($C_{1-6}$)-heteroalkynyl, optionally substituted cycloalkyl, optionally substituted cycloalkenyl, halide, optionally substituted oxygen containing functional group (e.g., alcohol, ketone, aldehyde, acyl halide, carbonate, carboxylic acid, ester, and ether), optionally substituted nitrogen containing functional group (e.g., amide, amine, imine, azide, cyanate, azo, nitrate, nitrile, nitro, and nitroso), optionally substituted sulfur containing functional group (e.g., thiol, sulfide, disulfide, sulfoxide, sulfone, sulfinic acid, sulfonic acid, thiocyanate, thione, and thial), optionally substituted phosphorous containing functional group (e.g., phosphine, phosphonic acid, phosphate, phosphodiester), optionally substituted boron containing functional group (e.g., boronic acid, boronic ester, borinic acid, and borinic ester);

$X^3$-$X^4$ are independently selected from $L^1$, optionally substituted hydrophobic amino acids, and optionally substituted hydrophilic amino acids.

In a particular embodiment, the disclosure provides for a dendronized polymer comprising a polymer backbone Formula I:

Formula I

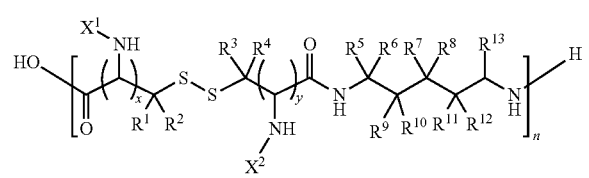

wherein, n is an integer greater than 100;

x and y are in ratio from 1:99 to 99:1;

$R^1$-$R^{12}$ are individually selected from the group comprising H, optionally substituted ($C_{1-12}$)-alkyl, optionally substituted ($C_{1-12}$)-heteroalkyl, optionally substituted ($C_{1-12}$)-alkenyl, optionally substituted ($C_{1-12}$)-heteroalkenyl, optionally substituted ($C_{1-12}$)-alkynyl, optionally substituted ($C_{1-12}$)-heteroalkynyl, optionally substituted cycloalkyl, optionally substituted cycloalkenyl, halide, optionally substituted oxygen containing functional group (e.g., alcohol, ketone, aldehyde, acyl halide, carbonate, carboxylic acid, ester, and ether), optionally substituted nitrogen containing functional group (e.g., amide, amine, imine, azide, cyanate, azo, nitrate, nitrile, nitro, and nitroso), optionally substituted sulfur containing functional group (e.g., thiol, sulfide, disulfide, sulfoxide, sulfone, sulfinic acid, sulfonic acid, thiocyanate, thione, and thial), optionally substituted phosphorous containing functional group (e.g., phosphine, phosphonic acid, phosphate, phosphodiester), optionally substituted boron containing functional group (e.g., boronic acid, boronic ester, borinic acid, and borinic ester);

$R^{13}$ is an ester;

$X^1$ has the structure of:

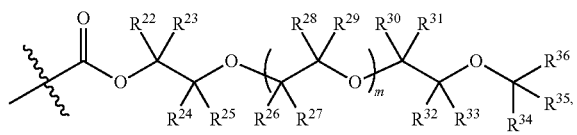

wherein m is an integer greater than 100, and $R^{22}$-$R^{36}$ are independently selected from H, optionally substituted ($C_{1-6}$)-alkyl, optionally substituted ($C_{1-6}$)-heteroalkyl, optionally substituted ($C_{1-6}$)-alkenyl, optionally substituted ($C_{1-6}$)-heteroalkenyl, optionally substituted ($C_{1-6}$)-alkynyl, optionally substituted ($C_{1-6}$)-heteroalkynyl, optionally substituted cycloalkyl, optionally substituted cycloalkenyl, halide, optionally substituted oxygen containing functional group (e.g., alcohol, ketone, aldehyde, acyl halide, carbonate, carboxylic acid, ester, and ether), optionally substituted nitrogen containing functional group (e.g., amide, amine, imine, azide, cyanate, azo, nitrate, nitrile, nitro, and nitroso), optionally substituted sulfur containing functional group (e.g., thiol, sulfide, disulfide, sulfoxide, sulfone, sulfinic acid, sulfonic acid, thiocyanate, thione, and thial), optionally substituted phosphorous containing functional group (e.g., phosphine, phosphonic acid, phosphate, phosphodiester), optionally substituted boron containing functional group (e.g., boronic acid, boronic ester, borinic acid, and borinic ester), and $R^{32}$ is selected from H, optionally substituted ($C_{1-6}$)-alkyl, optionally substituted ($C_{1-6}$)-heteroalkyl, optionally substituted ($C_{1-6}$)-alkenyl, optionally substituted ($C_{1-6}$)-heteroalkenyl, optionally substituted ($C_{1-6}$)-alkynyl, optionally substituted ($C_{1-6}$)-heteroalkynyl, optionally substituted cycloalkyl, optionally substituted cycloalkenyl, halide, optionally substituted oxygen containing functional group (e.g., alcohol, ketone, aldehyde, acyl halide, carbonate, carboxylic acid, ester, and ether), optionally substituted nitrogen containing functional group (e.g., amide, amine, imine, azide, cyanate, azo, nitrate, nitrile, nitro, and nitroso), optionally substituted sulfur containing functional group (e.g., thiol, sulfide, disulfide, sulfoxide, sulfone, sulfinic acid, sulfonic acid, thiocyanate, thione, and thial), optionally substituted phosphorous containing functional group (e.g., phosphine, phosphonic acid, phosphate, phosphodiester), optionally substituted boron containing functional group (e.g., boronic acid, boronic ester, borinic acid, and borinic ester), methacrylates, acrylates, maleimides, mesylates, N-hydroxysuccinimide (NHS) esters, reversible addition-fragmentation chain transfer (RAFT) groups, tosylates, and biotin; and $X^2$ is an optionally substituted L-lysine based dendron that is functionalized on the outer layer by comprising hydrophilic-based amino acids and hydrophobic-based amino acids.

In a particular embodiment, the disclosure provides for a dendronized polymer comprising a structure of Formula I(a):

Formula I(a)

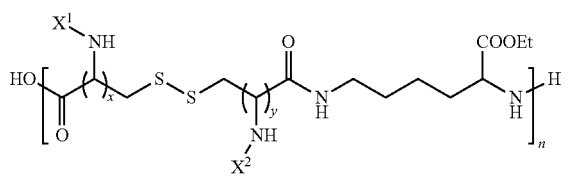

wherein, n is an integer greater than 100;

x and y are in ratio from 1:99 to 99:1; and $X^1$-$X^2$ are optionally substituted L-lysine based dendrons that are functionalized on the outer layer by comprising hydrophilic-based amino acids and hydrophobic-based amino acids.

In another embodiment, the disclosure provides for a dendronized polymer comprising a structure of Formula I(b):

Formula I(b)

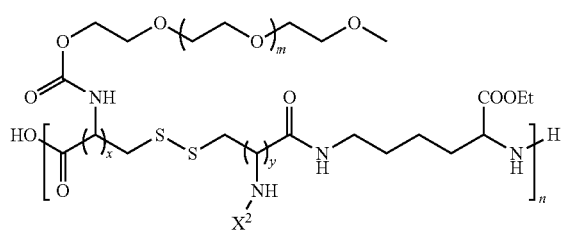

wherein, n is an integer greater than 100;

m is an integer greater than 100;

x and y are in ratio from 5:95 to 95:5; and $X^2$ is an optionally substituted L-lysine based dendron that is functionalized on the outer layer by comprising hydrophilic-based amino acids and hydrophobic-based amino acids.

In a particular embodiment, the disclosure provides for a dendronized polymer comprising a structure of Formula III:

Formula IV

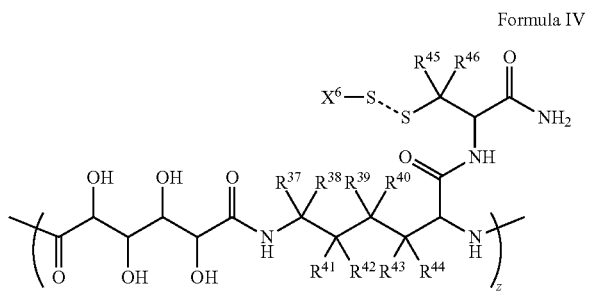

wherein, z is an integer greater than one;

$R^{37}$-$R^{46}$ are each independently selected from the group comprising H, optionally substituted $(C_{1-12})$-alkyl, optionally substituted $(C_{1-12})$-heteroalkyl, optionally substituted $(C_{1-12})$-alkenyl, optionally substituted $(C_{1-12})$-heteroalkenyl, optionally substituted $(C_{1-12})$-alkynyl, optionally substituted $(C_{1-12})$-heteroalkynyl, optionally substituted cycloalkyl, optionally substituted cycloalkenyl, halide, optionally substituted oxygen containing functional group (e.g., alcohol, ketone, aldehyde, acyl halide, carbonate, carboxylic acid, ester, and ether), optionally substituted nitrogen containing functional group (e.g., amide, amine, imine, azide, cyanate, azo, nitrate, nitrile, nitro, and nitroso), optionally substituted sulfur containing functional group (e.g., thiol, sulfide, disulfide, sulfoxide, sulfone, sulfinic acid, sulfonic acid, thiocyanate, thione, and thial), optionally substituted phosphorous containing functional group (e.g., phosphine, phosphonic acid, phosphate, phosphodiester), optionally substituted boron containing functional group (e.g., boronic acid, boronic ester, borinic acid, and borinic ester);

$X^6$ is a dendron comprised of a plurality of linked amino acids that is attached to the polymer backbone via a sulfide linkage.

In a certain embodiment, $X^6$ is a dendron comprised of a plurality of linked amino acids having the structure of Formula III:

Formula III

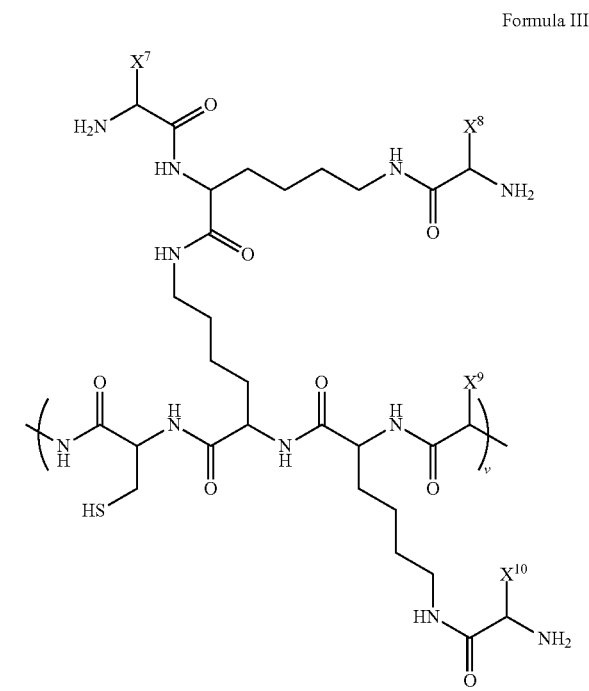

wherein, v is an integer greater than one;

$X^7$-$X^{10}$ are each independently hydrophobic or hydrophilic amino acid side groups.

The disclosure further provides that a "graft-from" approach can be used to produce the dendronized polymers of the disclosure. For example, dendronized polymers comprising the structure of Formula I can be made by following the generalized "graft from" method of SCHEME 1:

SCHEME 1
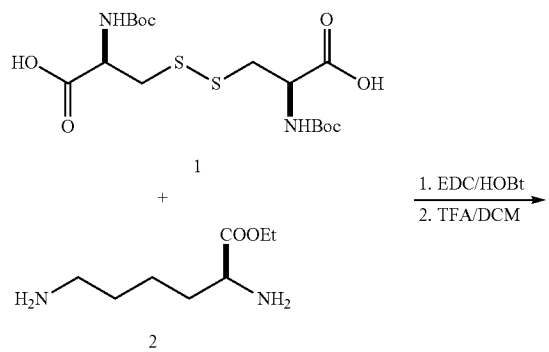
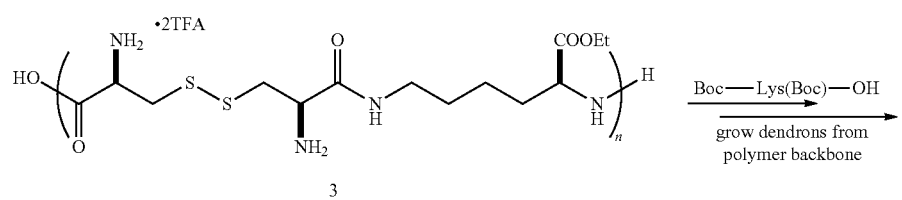
GPC Mn~15 kDa, PDI~1.8
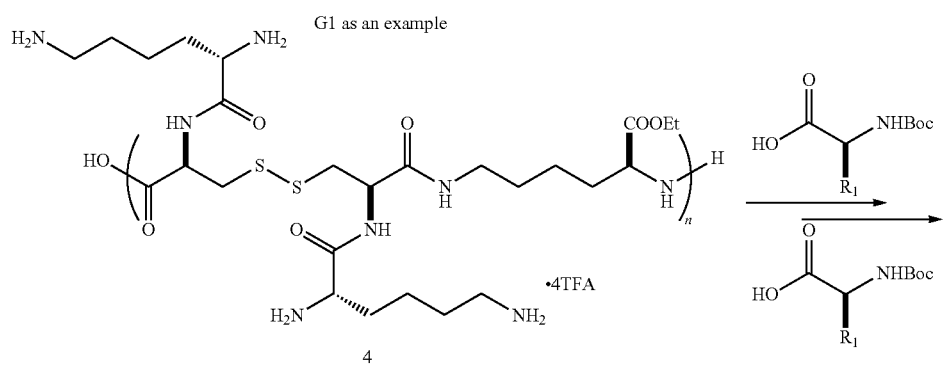

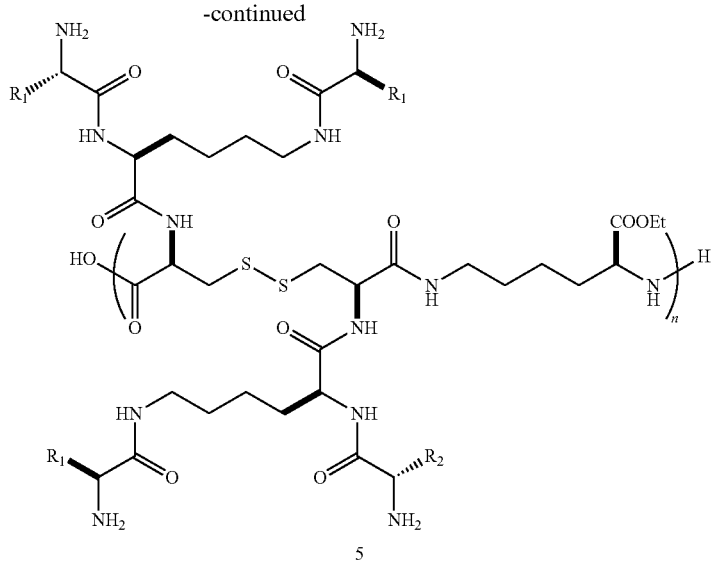

5

R₁ (hydrophilic):

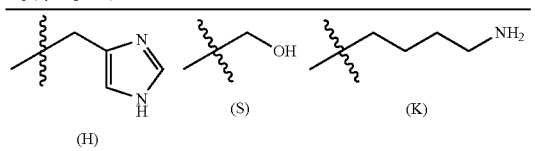

(H)  (S)  (K)

R₂ (hydrophobic):

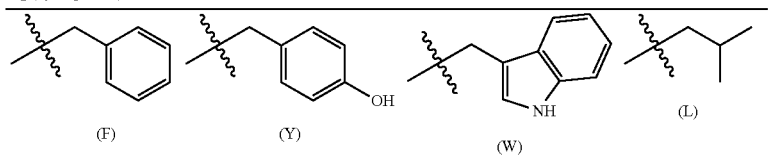

(F)  (Y)  (W)  (L)

A focused library of amphiphilic denpois
made by the "graft-from" approach:
G1: 75K-25F, 75K-25W, 75H-25F, 75H-25W G2: 50K-50F, 50H-50F, 75K-25F, 75K-25W,
75S-25F, 75H-25F, 75H-25W, 75H-25Y,
75H-25L, 88H-12F, 88H-12W In a particular embodiment, a "graft-from" approach can be used to construct denpols of the disclosure (SCHEME 1). The backbone of denpol is prepared by simple in situ peptide coupling polymerization between a dicysteine monomer 1 and a lysine monomer 2 (polymer $M_n$~15KD, PDI~1.8 by GPC). The disulfide linkages on the polymer backbone are introduced to be biodegradable under a reducing environment in the cytoplasm so as to facilitate nucleic acid decomplexation. After Boc deprotection, lysine-based dendrons were grown from the polymer backbone 4 generation by generation through solution phase peptide coupling. Finally, hydrophilic and hydrophobic amino acids at different molar ratios were coupled to the outer layer of the scaffold to introduce different functionalities 5. The chemical structures of the final denpols can then be characterized by ¹H NMR analysis. Following this "graft-from" protocol, a small focused library of amphiphilic denpols was quickly generated. Lysine and serine were chosen for the hydrophilic moiety with either charged or neutral side chain, and histidine was chosen for its good buffering capacity, which could help the endosomal escape by the "proton sponge" mechanism. Amino acids carrying aromatic or aliphatic hydrophobic group were incorporated into the denpol with different ratio. Throughout this disclosure, single letter amino acid codes will be used for naming. For example, G2 75H-25W represents a denpol with gen-2 dendrons composed of 75 mol % histidine (H) and 25 mol % tryptophan (W) residues on dendrons.

In an alternate embodiment, the disclosure provides a "combinatorial" approach can be used to produce the dendronized polymers of the disclosure. For example, dendronized polymers comprising the structure of Formula III can be made by following the generalized "combinatorial" method of SCHEME 2:

SCHEME 2
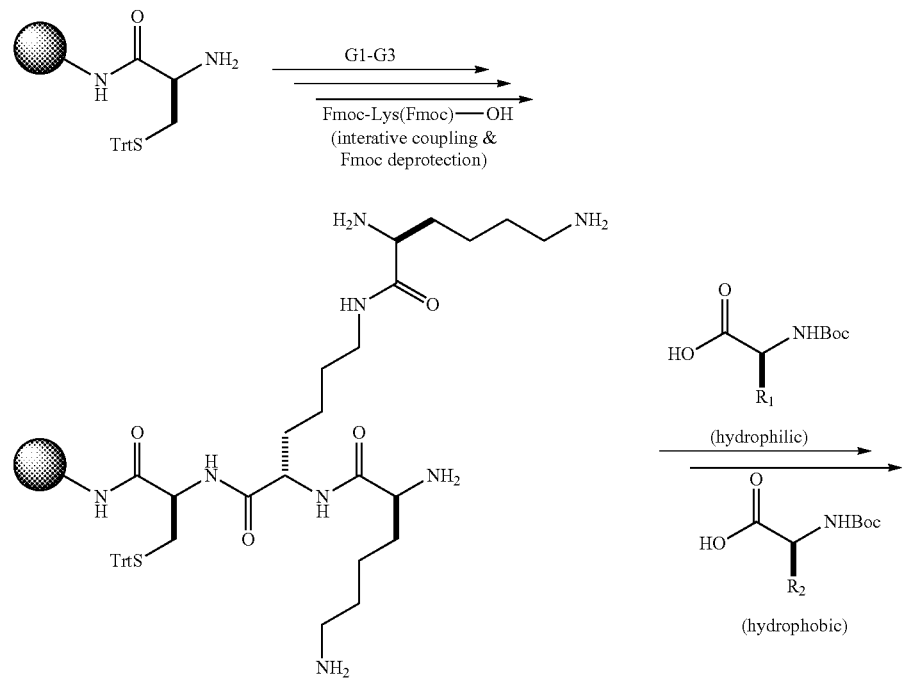
(show G2 synthesis as an example)
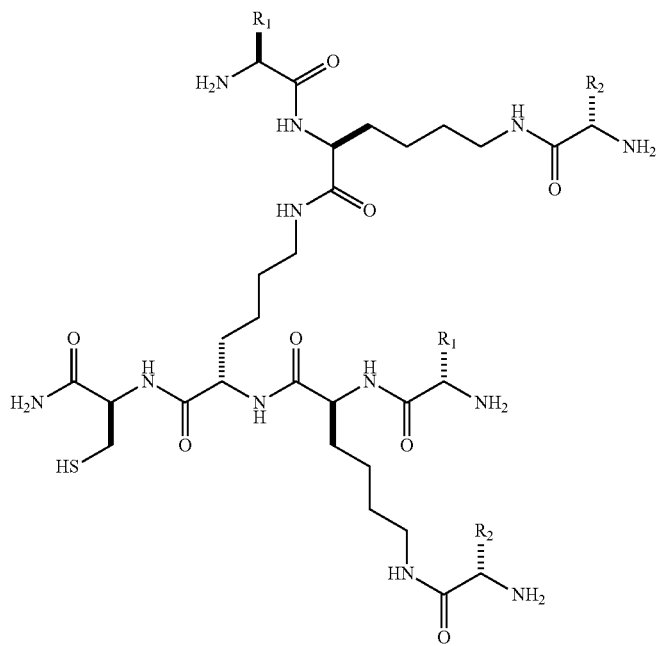
(show G2-dendron as an example)
G1-G3 dendrons:
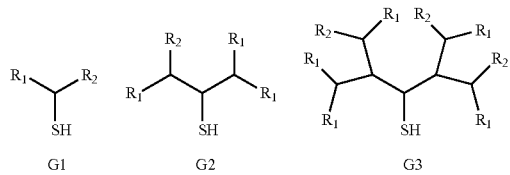

R₁ (hydrophilic side chain):

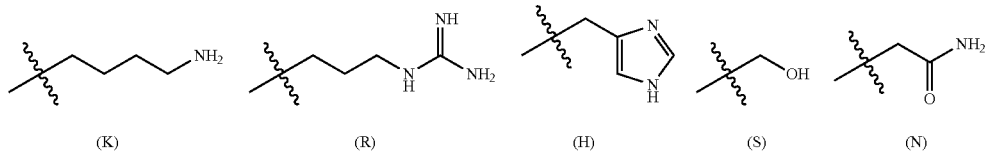

(K)　　　(R)　　　(H)　　　(S)　　　(N)

R₂ (hydrophobic side chain):

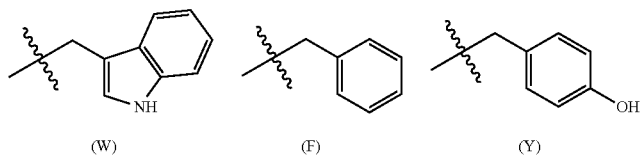

(W)　　　(F)　　　(Y)

In a particular embodiment, oligolysine can be used to construct the polymer backbone. Oligolysine can be facilely made by SPPS. Following procedure of Kantchev et al. (*Org Biomol Chem* 6(8):1377-85 (2008)), a library of dendrons with controlled size and functionalities are synthesized by automated SPPS (SCHEME 2). Briefly, Rink Amide Resin is first coupled with cysteine, which is then used as an anchoring group for grafting to the polymer backbone through a disulfide linkage. Lysine dendron is grown step by step until reaching the desired generation. Finally, the out layer is functionalized with a combination of hydrophilic (R₁) and hydrophobic (R₂) amino acids. Each of the outer layer amino acid residues carries one positive charge from the α-amino group, providing the base level of cationic charge density for the denpols. Depending on the coupling protocol, the spatial placement of different functional groups on the dendrons can be precisely controlled. After acid cleavage, each individual dendron is purified and characterized. SPPS is ideally suited because it provides expedient access to a large library of dendrons. Once promising dendrons are identified in later studies, standard solution phase synthesis can be easily adapted for making larger quantities of the identified dendrons for further studies.

In another embodiment, the disclosure provides a "graft-to" approach can be used to produce the dendronized polymers of the disclosure. For example, dendronized polymers comprising the structure of Formula IV can be made by following the generalized "graft-to" method of SCHEME 3:

SCHEME 3

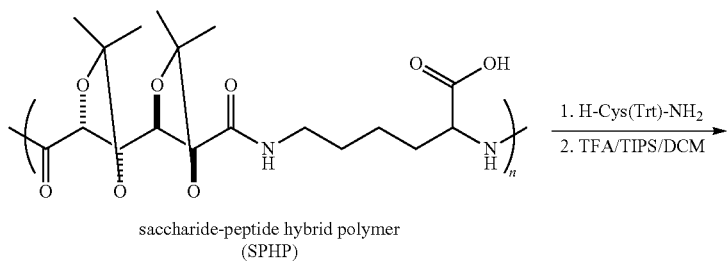

saccharide-peptide hybrid polymer
(SPHP)

6

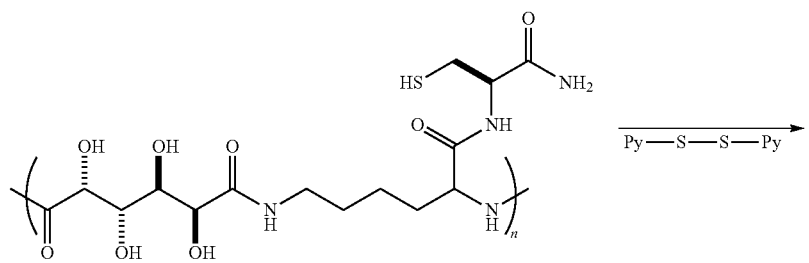

7

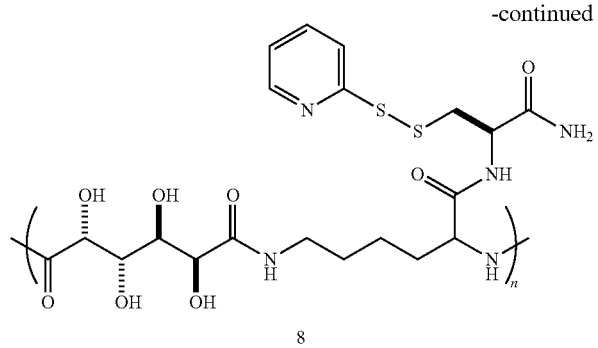

8

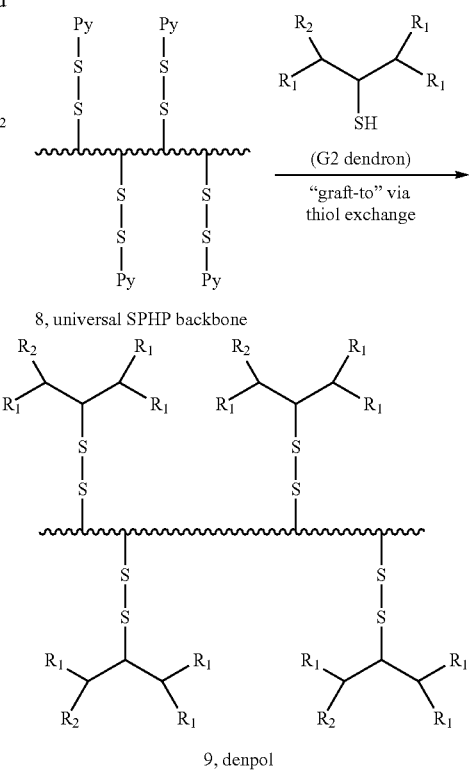

8, universal SPHP backbone 9, denpol

In a certain embodiment, a saccharide-peptide hybrid polymer (SPHP, 6) can be used to form a denpol of the disclosure. This polymer features facile synthesis, biodegradability, versatile functionalization and is nontoxic and non-immunogenic. The dendrons will be conjugated to the SPHP polymer backbone via disulfide bonds, which can be cleaved by cytosolic glutathione (GSH) to facilitate decomplexation of siRNA in cytosol. For this purpose, cysteine will be first coupled to the polymer backbone and then activated by 2,2'-dithioldipyridine. With this universal backbone 8, cysteine-terminated dendrons (G1-G3) can be conveniently grafted to polymer backbone via a thiol exchange reaction (SCHEME 3).

In a particular embodiment, a denpol disclosed herein comprises both hydrophilic and hydrophobic amino acids. In a further embodiment the denpol of the disclosure comprises one or more hydrophilic amino acids based on (1) moieties that have a positive charge that can facilitate binding with siRNAs (e.g., lysine (K) and arginine (R)); (2) moieties which can form hydrogen bonds (e.g., serine (S) and asparagine (N)); moieties that have good buffering capacity (e.g., histidine (H)). In another embodiment, the hydrophobic amino acids are hydrophobic aromatic amino acids (e.g., tryptophan (W), phenylalanine (F), and tyrosine (Y)). The indole ring of W can intercalate into double stranded siRNA and therefore increase binding strength. In addition, indole (W) and phenol (Y) groups are cytoprotective antioxidant that may help subside the oxidative immune response and improve cell viability after transfection. Use aforementioned methods, a binary library of G1-G3 dendrons can be synthesized which comprise hydrophobic amino acid residues and hydrophilic amino acid residues in a molar ratio of hydrophilic/hydrophobic ranging from 90:10, 75:25, or 60:40.

In another embodiment, the disclosure provides for systematic tuning of the spatial arrangement of the functional groups. The spatial placement of ligands can greatly affect the receptor binding and downstream biological response. A comparative study of the following three types of spatial arrangements (FIG. 24A-C) can be performed as follows to optimize the spatial arrangement of the functional groups to meet a specific application. First, a random hybrid dendron is prepared by adding a mixture of two different amino acids at the end of dendron synthesis (SCHEME 2) to distribute the functional groups randomly on the outer layer (FIG. 24A). A uniform hybrid dendron is then prepared by using Fmoc-Lys(Cbz)-OH in dendron preparation. Selective deprotection and subsequent coupling allows for the precise placement of different functional group at each position on the outer layer (FIG. 24B). Two mono-functional dendrons are also prepared, which will be co-grafted onto the denpol backbone at the desired ratio (FIG. 24C). All three types of denpols are prepared to have the same composition, and their biological properties are then compared in subsequent studies. Second, in conjugating dendrons onto polymer backbone, the space between dendrons can be controlled by the grafting density, which is modulated by the molar ratio of dendron to polymer backbone. The remaining functional sites are capped by a concurrent reaction with 2-mercaptoethanol ($HSCH_2CH_2OH$).

In a further embodiment, a dendronized polymer disclosed herein further comprises targeting ligands. Examples of targeting ligands, include but are not limited to, antibodies, aptamers, cholesterol and its derivatives, folate compounds or folate conjugates, transferrin, saccharides (e.g., mono-, di-, oligo-saccharides), and cell-penetrating peptides. These targeting ligands can be conjugated to the dendronized polymers by using the techniques presented in Shu et al. (*Annual Review of Physical Chemistry* 64:631-657 (2013)), Gauthier et al. (*Chem. Commun* 23:2591-2611 (2008)), Menzel (*Advances in Polymer Science* 253:1-36 (2013)), Mero et al. (*Methods Mol Biol.* 751:95-129 (2011)), Roberts et al. (*Advanced Drug Delivery Reviews* 54:459-476 (2002)), Steenis et al. (*Journal of Controlled Release* 87:167-176 (2003)), which are incorporated herein in-full, including the references cited therein.

In another embodiment, the dendronized polymers disclosed herein further comprise an oligonucleotide (e.g., siRNA) or a polynucleotide.

In a particular embodiment, the disclosure provides methods for delivering an oligonucleotide or polynucleotide to a cell in vitro or in vivo comprising contacting the cell with a pharmaceutical composition disclosed herein or a dendronized polymer of the disclosure. In a further embodiment, the disclosure provides methods for inducing an RNAi response in a cell by delivering a siRNA into a cell by using a dendronized polymer disclosed herein.

Extracellularly, siRNAs are highly susceptible to degradation by enzymes found in serum and tissues. The half-life of naked siRNAs in serum ranges from several minutes to an hour. The large size and negative charge of naked siRNAs thwarts their diffusion across the plasma membrane and prevents intracellular accumulation. siRNA delivery strategies that take advantage of endocytosis also must provide for endosomal escape. In the experiments presented herein, the dendronized polymers of the disclosure can form complexes with siRNA, are stable in serum, allow for siRNA diffusion across the plasma membrane, and provide for endosomal escape. Accordingly, the dendronized polymers disclosed herein are particularly suited for delivering siRNAs to cells.

As used herein, a nucleic acid domain, used interchangeably with oligonucleotide or polynucleotide domain can be any oligonucleotide or polynucleotide (e.g., a ribozyme, antisense molecule, siRNA, dsRNA, polynucleotide, oligonucleotide and the like). Oligonucleotides or polynucleotides generally contain phosphodiester bonds, although in some cases, nucleic acid analogs are included that may have alternate backbones, comprising, e.g., phosphoramidate, phosphorothioate, phosphorodithioate, or O-methyl-phophoroamidite linkages (see Eckstein, Oligonucleotides and Analogues: A Practical Approach, Oxford University Press); and peptide nucleic acid backbones and linkages. Other analog nucleic acids include those with positive backbones; non-ionic backbones, and non-ribose backbones, including those described in U.S. Pat. Nos. 5,235,033 and 5,034,506, and Chapters 6 and 7, ASC Symposium Series 580, Carbohydrate Modifications in Antisense Research, Sanghui & Cook, eds. Nucleic acids containing one or more carbocyclic sugars are also included within one definition of nucleic acids. Modifications of the ribose-phosphate backbone may be done for a variety of reasons, e.g. to increase the stability and half-life of such molecules in physiological environments. Oligonucleotides, as used this disclosure, therefore encompass siRNAs which have been chemically modified to prolong the siRNA half-life in serum and increased cellular uptake. Examples of such modifications, including modifying the sugar moiety by incorporating a 2'-fluoro, 2'-omethyl, 2'-halogen, 2'-amine, or 2-'deoxy, or by bridging the sugar's 2' and 4' positions with a —O—$CH_2$ linker (i.e., a 'locked nucleic acid'); by modifying the internucleotide phosphate linkage in siRNA by replacing the phosphodiester linkage with phosphothioate or boranophosphate; by modifying the siRNA nucleobases by replacing uridine bases with 4-thiouridine, 5-bromouridine, 5-iodouridine, N-3-Me-uridine or 2,6-diaminopurine residues, or by replacing seed region nucleotides 2-8 (from the 5'end of the guide strand) of siRNA with DNA nucleotides. Mixtures of naturally occurring nucleic acids and analogs are encompassed by the term oligonucleotide and polynucleotide; alternatively, mixtures of different nucleic acid analogs, and mixtures of naturally occurring nucleic acids and analogs can be made. Furthermore, hybrids of DNA and RNA can be used. dsDNA, ssDNA, dsRNA, siRNA are encompassed by the term oligonucleotide and polynucleotide. Additionally, the term oligonucleotides and polynucleotides, as used herein, includes modifications of siRNA termini, including tagging the ends of siRNAs with moieties such as cholesterol, folate, various peptides, and aptamers; fluorescent molecules; 3'-biotin; and 3'-ends with dinucleotide overhangs that mimic Dicer cleavage products.

A polynucleotide refers to a polymeric compound made up of any number of covalently bonded nucleotide monomers, including nucleic acid molecules such as DNA and RNA molecules, including single-double- and triple-stranded such molecules, and is expressly intended to embrace that group of polynucleotides commonly referred to as "oligonucleotides", which are typically distinguished as having a relatively small number (no more than about 30, e.g., about 5-10, 10-20, and 20-30) of nucleotide bases.

As used herein, the term "siRNA" is an abbreviation for "short interfering RNA", also sometimes known as "small interfering RNA" or "silencing RNA", and refers to a class of nucleotide-long double-stranded ribonucleic acid molecules that in eukaryotes are involved in the RNA interference (RNAi) pathway that results in post-transcriptional, sequence-specific gene silencing.

The term "dsRNA" is an abbreviation for "double-stranded RNA" and as used herein refers to a ribonucleic acid molecule having two complementary RNA strands.

As described above, the nucleic acid may be DNA, both genomic and cDNA, RNA or a hybrid, where the nucleic acid may contain combinations of deoxyribo- and ribo-nucleotides, and combinations of bases, including uracil, adenine, thymine, cytosine, guanine, inosine, xanthine hypoxanthine, isocytosine, isoguanine, etc. As used herein, the term "nucleoside" includes nucleotides and nucleoside and nucleotide analogs, and modified nucleosides such as amino modified nucleosides. In addition, "nucleoside" includes non-naturally occurring analog structures. Thus, e.g. the individual units of a peptide nucleic acid, each containing a base, are referred to herein as a nucleoside.

The nucleic acid domain of a nucleic acid construct described herein is not limited by any particular sequence. Any number of oligonucleotide or polynucleotides useful for diagnostics, therapeutics and research can be used in the methods and compositions of the disclosure.

The practice of phosphoramidite chemistry to prepare oligonucleotides is known from the published work of M. Caruthers and S. Beaucage and others. U.S. Pat. Nos. 4,458,066, 4,500,707, 5,132,418, 4,415,732, 4,668,777, 4,973,679, 5,278,302, 5,153,319, 5,218,103, 5,268,464, 5,000,307, 5,319,079, 4,659,774, 4,672,110, 4,517,338, 4,725,677 and Re. 34,069, each of which is herein incorporated by reference, describe methods of oligonucleotide synthesis. Additionally, the practice of phosphoramidite chemistry has been systematically reviewed by Beaucage and Iyer (*Tetrahedron* 48:2223-2311 (1942)) and (*Tetrahedron* 49:6123-6194 (1993)), or references referred to therein, all of which are herein incorporated by reference.

Nucleic acid synthesizers are commercially available and their use is generally understood by persons of ordinary skill in the art as being effective in generating nearly any oligonucleotide of reasonable length which may be desired.

In practicing phosphoramidite chemistry useful 5'OH sugar blocking groups are trityl, momomethoxytrityl, dimethoxytrityl and trimethoxytrityl, especially dimethoxytrityl (DMTr). In practicing phosphoramidite chemistry useful phosphite activating groups, i.e., $NR_2$, are dialkyl substituted nitrogen groups and nitrogen heterocycles. One approach includes the use of the di-isopropylamino activating group.

Oligonucleotides can be synthesized by a Mermade-6 solid phase automated oligonucleotide synthesizer or any commonly available automated oligonucleotide synthesizer. Triester, phosphoramidite, or hydrogen phosphonate coupling chemistries described in, for example, M. Caruthers, Oligonucleotides: Antisense Inhibitors of Gene Expression., pp. 7-24, J. S. Cohen, ed. (CRC Press, Inc. Boca Raton, Fla., 1989) or Oligonucleotide synthesis, a practical approach, Ed. M. J. Gait, IRL Press, 1984; "Oligonucleotides and Analogues, A Practical Approach", Ed. F. Eckstein, IRL Press, 1991, are employed by these synthesizers to provide the desired oligonucleotides. The Beaucage reagent, as described in, for example, *Journal of American Chemical Society* 112:1253-1255 (1990), or elemental sulfur, as described in Beaucage et al., (*Tetrahedron Letters* 22:1859-1862 (1981)), is used with phosphoramidite or hydrogen phosphonate chemistries to provide substituted phosphorothioate oligonucleotides. For example, the reagents comprising the protecting groups recited herein can be used in numerous applications where protection is desired. Such applications include, but are not limited to, both solid phase and solution phase, oligo-synthesis, polynucleotide synthesis and the like. The use of nucleoside and nucleotide analogs is also contemplated by this disclosure to provide oligonucleotide or oligonucleoside analogs bearing the protecting groups disclosed herein. Thus the terms nucleoside, nucleotide, deoxynucleoside and deoxynucleotide generally include analogs such as those described herein. These analogs are those molecules having some structural features in common with a naturally occurring nucleoside or nucleotide such that when incorporated into an oligonucleotide or oligonucleoside sequence, they allow hybridization with a naturally occurring oligonucleotide sequence in solution. Typically, these analogs are derived from naturally occurring nucleosides and nucleotides by replacing and/or modifying the base, the ribose or the phosphodiester moiety. The changes can be tailor made to stabilize or destabilize hybrid formation or enhance the specificity of hybridization with a complementary nucleic acid sequence as desired.

For instance, structural groups are optionally added to the ribose or base of a nucleoside for incorporation into an oligonucleotide, such as a methyl, propyl or allyl group at the 2'-0 position on the ribose, or a fluoro group which substitutes for the 2'-O group, or a bromo group on the ribonucleoside base. For use with phosphoramidite chemistry, various amidite reagents are commercially available, including 2'-deoxy amidites, 2'-O-methyl amidites and 2'-O-hydroxyl amidites. Any other means for such synthesis may also be employed. The actual synthesis of the oligonucleotides is well within the talents of those skilled in the art. It is also well known to use similar techniques to prepare other oligonucleotides such as the phosphorothioates, methyl phosphonates and alkylated derivatives. It is also well known to use similar techniques and commercially available modified amidites and controlled-pore glass (CPG) products such as biotin, Cy3, fluorescein, acridine or psoralen-modified amidites and/or CPG (available from Glen Research, Sterling Va.) to synthesize fluorescently labeled, biotinylated or other conjugated oligonucleotides.

In a certain embodiment, the disclosure provides for a pharmaceutical composition which comprises the dendronized polymers of the disclosure. Moreover, the pharmaceutical composition can be formulated into a form suitable for administration to a subject including the use of carriers, excipients, additives or auxiliaries. Frequently used carriers or auxiliaries include magnesium carbonate, titanium dioxide, lactose, mannitol and other sugars, talc, milk protein, gelatin, starch, vitamins, cellulose and its derivatives, animal and vegetable oils, polyethylene glycols and solvents, such as sterile water, alcohols, glycerol, and polyhydric alcohols. Intravenous vehicles include fluid and nutrient replenishers. Preservatives include antimicrobial, antioxidants, chelating agents, and inert gases. Other pharmaceutically acceptable carriers include aqueous solutions, non-toxic excipients, including salts, preservatives, buffers and the like, as described, for instance, in Remington's Pharmaceutical Sciences, 15th ed., Easton: Mack Publishing Co., 1405-1412, 1461-1487 (1975), and The National Formulary XIV., 14th ed., Washington: American Pharmaceutical Association (1975), the contents of which are hereby incorporated by reference. The pH and exact concentration of the various components of the pharmaceutical composition are adjusted according to routine skills in the art. See Goodman and Gilman's, The Pharmacological Basis for Therapeutics (7th ed.).

The pharmaceutical compositions according to the disclosure may be administered at a therapeutically effective amount either locally or systemically. As used herein, "administering a therapeutically effective amount" is intended to include methods of giving or applying a pharmaceutical composition of the disclosure to a subject that allow the composition to perform its intended therapeutic function. The therapeutically effective amounts will vary according to factors, such as the degree of infection in a subject, the age, sex, and weight of the individual. Dosage regime can be adjusted to provide the optimum therapeutic response. For example, several divided doses can be administered daily or the dose can be proportionally reduced as indicated by the exigencies of the therapeutic situation.

The pharmaceutical composition can be administered in a convenient manner, such as by injection (e.g., subcutaneous, intravenous, and the like), oral administration, inhalation, transdermal application, or rectal administration. Depending on the route of administration, the pharmaceutical composition can be coated with a material to protect the pharmaceutical composition from the action of enzymes, acids, and other natural conditions that may inactivate the pharmaceutical composition. The pharmaceutical composition can also be administered parenterally or intraperitoneally. Dispersions can also be prepared in glycerol, liquid polyethylene glycols, and mixtures thereof, and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersions. The composition will typically be sterile and fluid to the extent that easy syringability exists. Typically the composition will be stable under the conditions of manufacture and storage and preserved against the contaminating action of microorganisms, such as bacteria and fungi. The carrier can be a solvent or dispersion medium containing, for example, water, ethanol, polyol (for example, glycerol, propylene glycol, and liquid polyetheylene glycol, and the like), suitable mixtures thereof, and vegetable oils. The proper fluidity can be maintained, for example, by the use of a coating, such as lecithin, by the maintenance of the required particle size, in the case of dispersion, and by the use of surfactants. Prevention of the action of microorganisms can be achieved by various antibacterial and antifungal agents, for example, parabens, chlorobutanol, phenol, ascorbic acid, thimerosal, and the like. In many cases, isotonic agents, for example, sugars, polyalcohols, such as mannitol, sorbitol, or sodium chloride are used in the composition. Prolonged absorption of the injectable compositions can be brought about by including in the composition an agent that delays absorption, for example, aluminum monostearate and gelatin.

Sterile injectable solutions can be prepared by incorporating the pharmaceutical composition in the required amount in an appropriate solvent with one or a combination of ingredients enumerated above, as required, followed by filtered sterilization. Generally, dispersions are prepared by incorporating the pharmaceutical composition into a sterile vehicle that contains a basic dispersion medium and the required other ingredients from those enumerated above.

The pharmaceutical composition can be orally administered, for example, with an inert diluent or an assimilable edible carrier. The pharmaceutical composition and other ingredients can also be enclosed in a hard or soft-shell gelatin capsule, compressed into tablets, or incorporated directly into the subject's diet. For oral therapeutic administration, the pharmaceutical composition can be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations can, of course, be varied and can conveniently be between about 5% to about 80% of the weight of the unit.

The tablets, troches, pills, capsules, and the like can also contain the following: a binder, such as gum gragacanth, acacia, corn starch, or gelatin; excipients such as dicalcium phosphate; a disintegrating agent, such as corn starch, potato starch, alginic acid, and the like; a lubricant, such as magnesium stearate; and a sweetening agent, such as sucrose, lactose or saccharin, or a flavoring agent such as peppermint, oil of wintergreen, or cherry flavoring. When the dosage unit form is a capsule, it can contain, in addition to materials of the above type, a liquid carrier. Various other materials can be present as coatings or to otherwise modify the physical form of the dosage unit. For instance, tablets, pills, or capsules can be coated with shellac, sugar, or both. A syrup or elixir can contain the agent, sucrose as a sweetening agent, methyl and propylparabens as preservatives, a dye, and flavoring, such as cherry or orange flavor. Of course, any material used in preparing any dosage unit form should be pharmaceutically pure and substantially non-toxic in the amounts employed. In addition, the pharmaceutical composition can be incorporated into sustained-release preparations and formulations.

Thus, a "pharmaceutically acceptable carrier" is intended to include solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the pharmaceutical composition, use thereof in the therapeutic compositions and methods of treatment is contemplated. Supplementary active compounds can also be incorporated into the compositions.

It is especially advantageous to formulate parenteral compositions in dosage unit form for ease of administration and uniformity of dosage. "Dosage unit form" as used herein, refers to physically discrete units suited as unitary dosages for the subject to be treated; each unit containing a predetermined quantity of pharmaceutical composition is calculated to produce the desired therapeutic effect in association with the required pharmaceutical carrier. The specification for the dosage unit forms of the disclosure are related to the characteristics of the pharmaceutical composition and the particular therapeutic effect to be achieve.

The principal pharmaceutical composition is compounded for convenient and effective administration in effective amounts with a suitable pharmaceutically acceptable carrier in an acceptable dosage unit. In the case of compositions containing supplementary active ingredients, the dosages are determined by reference to the usual dose and manner of administration of the said ingredients.

For use in the therapeutic applications described herein, kits and articles of manufacture are also described herein. Such kits can comprise a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. The containers can be formed from a variety of materials such as glass or plastic.

For example, the container(s) can comprise one or more denpols described herein, optionally in a composition or in combination with another agent (e.g., siRNAs) as disclosed herein. The container(s) optionally have a sterile access port (for example the container can be an intravenous solution bag or a vial having a stopper pierceable by a hypodermic injection needle). Such kits optionally comprise an identifying description or label or instructions relating to its use in the methods described herein.

A kit will typically comprise one or more additional containers, each with one or more of various materials (such as reagents, optionally in concentrated form, and/or devices) desirable from a commercial and user standpoint for use of a compound described herein. Non-limiting examples of such materials include, but are not limited to, buffers, diluents, filters, needles, syringes; carrier, package, container, vial and/or tube labels listing contents and/or instructions for use, and package inserts with instructions for use. A set of instructions will also typically be included.

A label can be on or associated with the container. A label can be on a container when letters, numbers or other characters forming the label are attached, molded or etched into the container itself, a label can be associated with a container when it is present within a receptacle or carrier that also holds the container, e.g., as a package insert. A label can be used to indicate that the contents are to be used for a specific therapeutic application. The label can also indicate directions for use of the contents, such as in the methods described herein. These other therapeutic agents may be used, for example, in the amounts indicated in the Physicians' Desk Reference (PDR) or as otherwise determined by one of ordinary skill in the art.

The following examples are intended to illustrate but not limit the disclosure. While they are typical of those that might be used, other procedures known to those skilled in the art may alternatively be used.

EXAMPLES

Materials.

Unless otherwise noticed, all reagents were used as received from commercial suppliers without further purification. Protected amino acids were purchased from Advanced ChemTech (Loiusville, Ky.) and Aroz Technologies, LLC. (Cincinnati, Ohio). Coupling reagents were purchased from GL Biochem Ltd. (Shanghai, China). Branched polyethyleneimine (PEI, 25 kDa) was purchased from Sigma-Aldrich (St. Louis, Mo.). Sodium Dextran Sulfate (25 kDa) was purchased from TCI America (Portland, Oreg.) and was used as received. GelRed™ siRNA stain was purchased from VWR (Radnor, Pa.). Silencer anti-GFP siRNA, Silencer Select negative control siRNA, Silencer Cy™-3 labeled Negative Control siRNA and Lipofectamine® RNAiMAX were purchased from Invitrogen (Carlsbad, Calif.). All reactions were performed in HPLC grade unless otherwise noted. All water used in biological experiments was nanopure water obtained from Barnstead Nanopure Diamond (Waltham, Mass.). Cell culture media, Dulbecco's modified Eagle's medium ("DMEM") and fetal bovine serum ("FBS") were purchased from Invitrogen (Carlsbad, Calif.).

Instruments.

All the denpols were characterized by nuclear magnetic resonance ("NMR") and the molecular weight and molecular weight distribution of denpol backbone was measured by gel permeation chromatography ("GPC"). $^1$H NMR spectra were recorded at 500 MHz on Bruker instruments. $^1$H NMR chemical shifts were reported as values in ppm relative to deuterated solvents $D_2O$ (4.80). GPC was performed on an Agilent 1100 SEC system using a OHpak SB-803 HQ column from Shodex, and the molecular weight was determined with respect to poly(ethylene glycol) ("PEG") standards purchased from Aldrich. DMF with 0.1% LiBr (wt/v) was used as the eluent at a flow rate of 1.0 mL/min with column temperature at 45° C. The size and zeta potential of denpol/siRNA polyplexes were measured at 633 nm using Zetasizer (NanoZS) dynamic light scattering instrument (Malvern Instruments, Malvern, UK) at 25° C. with detection angle of 173°. The nanoparticle formed by denpol/siRNA complexes was visualized on a FEI/Philips CM-20 conventional TEM operated at an accelerating voltage of 200 kV. The flow cytometry data was obtained on a Becton-Dickinson LSR II flow cytometer with argon ion excitation laser at 488 nm (Becton-Dickinson, Franklin Lakes, N.J.). Confocal fluorescence images were acquired using a Zeiss LSM 510 inverted laser-scanning confocal microscope.

Procedure for Denpol Functionalization:

In a one drum glass vial were added unfunctionalized denpol (30 mg) at a desired generation, and two different boc-protected amino acids at a specified ratio. DMF (1 mL) was added to dissolve the solids, followed by adding BOP (1.05 equiv to the primary amines) and DIPEA (1.05 equiv to the primary amines). The reaction was left to stir for 24 hours at ambient temperature. Protected denpol was precipitated in an excess amount of deionized water. After removing water completely, the solid was dissolved in TFA (3 mL), DCM (1 mL) and triisopropylsilane (0.1 mL) as the scavenger. After stirring overnight, excess TFA and DCM was removed in vacuo, the resulting polymer was redissovled in methanol and precipitated in ether. The precipitate was dissolved in water and lyophilized to give a white powder. All denpols were characterized by $^1$H NMR. The functionalization ratio in NMR was calculated by comparing the characteristic side chain peak with the aliphatic region in lysine.

Gel Electrophoresis.

The binding of siRNA to denpol was studied by agarose gel electrophoresis. Both siRNA and denpol were diluted with 10 mM phosphate buffer (pH 7.4). Different amounts of a denpol solution (5 mg/mL) were added to a 4 μM siRNA solution (5.0 μL) to achieve different N/P ratios (the molar ratio of primary amine groups from denpol and phosphate groups from siRNA, imidazole groups of histidine residues were not counted because they are not protonated at pH 7.4). The same buffer was added to adjust the final volume to 10.0 μL, followed by a 30 minute incubation at room temperature. 6× gel loading dye (2.5 μL) was added to each sample and 10 μL of the mixture was loaded into each well of a 1% agarose gel with 1×GelRed™ dye. Electrophoresis was run in TAE buffer (pH 7.9) at 60 V for 45 min and the gel was visualized under a UV transilluminator.

Dextran Sulfate Competitive Binding Assay.

The binding strength of siRNA to denpol was studied by competitive binding assay with dextran sulfate ("DS"). To a 4 μM siRNA solution (5 μL) was added different denpol solutions at N/P 40 and incubated for 1 hour at ambient temperature. A DS solution (1 μL) having different concentrations was added to the complex to achieve the different S/P ratios (the molar ratio of sulfate groups from DS and phosphate groups from siRNA) The mixture was then incubated for another 30 minutes. The samples were then subjected to agarose gel electrophoresis under the aforementioned conditions.

Glutathione Triggered Release of siRNA from Denpol Complexes.

To a 4 μM siRNA solution (5 μL) was added a concentrated denpol solution to achieve N/P 40 and the final volume was adjusted to 10 μL by adding phosphate buffer (pH 7.4). After a 1 hour incubation at room temperature, 55 mM glutathione (GSH) (1 μL) was added to the polyplex solution to achieve a 5 mM final concentration that was then followed by a 30 minute incubation at ambient temperature. All samples were then subjected to agarose gel electrophoresis under the aforementioned conditions.

DLS Measurements.

The size and zeta potential of denpol/siRNA polyplexes were measured at 633 nm using a Zetasizer (NanoZS) dynamic light scattering instrument (Malvern Instruments, Malvern, UK) at 25° C. with detection angle of 173°. Both denpol and siRNA were diluted in nanopure water, and a denpol solution (50 μL) was added to a 1.5 μM siRNA solution (50 μL; N/P 40), followed by brief vortexing. After incubating at ambient temperature for 30 minutes, a DLS measurement was taken. The solution was then diluted with PBS (600 μL), and subjected to zeta-potential measurement. For PEGylated denpol studies, branched PEI ($M_n$=25 k) was complexed with siRNA at N/P=15 and included in the measurement as a control. At least three measurements were taken for each sample and the mean values were reported.

TEM Characterization.

The nanoparticle formed by denpol/siRNA complexes was visualized on a FEI/Philips CM-20 conventional TEM operated at an accelerating voltage of 200 kV. Samples were prepared by placing a drop of siRNA/denpol complex solution in DI water (1 mg/mL) on a TEM grid (Ted Pella, Silicon Monoxide Type-A, 300 Mesh). The excess solvent was removed by placing the sample on a filter paper. The siRNA/denpol complexes were stained by placing a drop of 1.0 wt % aqueous solution of uranyl acetate for 1 minute, followed by removal of excess solvent.

Cell Culture.

NIH 3T3 fibroblast cells with or without green fluorescent protein (GFP) were cultured in a standard $CO_2$ incubator. The culture media was DMEM with 10% fetal bovine serum (FBS). The cells were trypsinized and passaged when they reached ~90% confluency.

MTT Assay.

NIH 3T3 fibroblast cells were seeded at a density of 5000 cells/well in 96-well plates for 24 hours. The culture media was then changed from DMEM (100 μL) with 10% fetal bovine serum (FBS) to serum free DMEM (80 μL) before the toxicity assay. A PBS solution (20 μL) containing different amounts of denpols were added to each well, followed by a 24 hour incubation. The media was then changed back to DMEM with 10% FBS and cultured for another 48 hours. The media was replaced with a DMEM solution (50 μL) containing 0.5 mg/mL MTT, followed by a 4 hour incubation at 37° C. DMSO (100 μL) was added to the solution to dissolve the formed fomazan. A MTT reading was obtained by using a plate reader (Abs 540 nm). As a positive control, cells were also treated with poly(ethylene imine) ("PEI") at different concentrations under the same conditions.

Transfection Screening.

NIH 3T3 fibroblast cells expressing GFP were seeded at a density of 5000 cells/well in 96-well plates for 4 hours. Prior to transfection, the media was replaced with serum free DMEM (80 μL). Different polyplex solutions (20 μL) at various N/P ratios were added to each well to make the final siRNA concentration of 100 nM, which was followed by incubating at 37° C. for 4 hours. The media was changed back to DMEM with 10% FBS. After 48 hours, the fluorescence of each well was measured by using a plate reader (Ex. 460 nm, EM. 525 nm). After the fluorescence reading, cell viability was measured by a MTT assay and the fluorescence was then normalized by percent viability to eliminate toxicity-induced GFP reduction. As positive controls, two bench-mark vectors, PEI and Lipofectamine® RNAiMAX were also included in the study, and the transfection was carried out following the manufacturer's protocol (100 nM siRNA concentration).

Flow Cytometry Analysis of Transfected Cells.

NIH 3T3 fibroblast cells expressing GFP were seeded at a density of 10,000 cells/well in 48-well plates for 24 hours. Prior to transfection, the media was replaced with serum free DMEM (200 μL). Different siRNA/denpol complex solutions (50 μL) were added to each well to make the final siRNA concentration 100 nM. After incubating for 4 or 24 hours, the media was changed back to DMEM with 10% serum and cultured for another 24 or 48 hours. Before the analysis, cells were released from each well by trypsin and harvested by centrifugation. The GFP fluorescence of transfected cells was measured on a Becton-Dickinson LSR II flow cytometer with argon ion excitation laser at 488 nm (Becton-Dickinson, Franklin Lakes, N.J.). For each sample, data representing 10,000 objects were collected as a list-mode file and analyzed using FACSDiva™ software (Becton Dickinson, version 6.1.3). The transfection efficiency was presented by comparing the fluorescence of transfected cells with untreated cells.

Confocal Laser Scanning Microscopy.

Confocal laser scanning microscopy was used to track labeled siRNA in the transfected cells. Unmodified NIH 3T3 fibroblast cells were seeded at a density of 15000 cells/well on an 8-well chamber slide (Lab-Tek, Rochester, N.Y.) for 24 hours. Cy3-labeled siRNA was complexed with different denpols at N/P 80 and used to transfect the cells under the aforementioned conditions. After transfection, the media was switched back to DMEM with 10% serum. Confocal fluorescence spectroscopy was performed at different time points after the transfection. The nucleus was counter-stained with DAPI. All confocal images were acquired using a Zeiss LSM 510 inverted laser-scanning confocal microscope. A 40×numerical aperture of 1.4 oil immersion planapochromat objective was used for all experiments. A 559 nm helium-neon laser, a SMD640 dichroic mirror, and a 575-620 nm band-pass barrier filter were used to obtain the images of Cy3-labeled siRNA. Images of DAPI-stained nuclei were acquired using a 780 nm two-photon excitation light, a 635 nm dichroic mirror, and a 655-755 nm band-pass barrier filter. The two fluorescent images were scanned separately and overlaid together with the differential interference contrast image (DIC). The cells were scanned as a z-stack of two-dimensional images (1024×1024 pixels) and an image cutting approximately through the middle of the cellular height was selected to present the intracellular siRNA localization.

Statistical Analysis.

All quantitative assays were performed in triplicates, data were expressed as mean±SEM.

Small Focused Library Screening Assays.

To demonstrate the proof of concept, a small focused library of amino acid based denpol by a "graft-from" approach as presented in SCHEME 4:

SCHEME 4

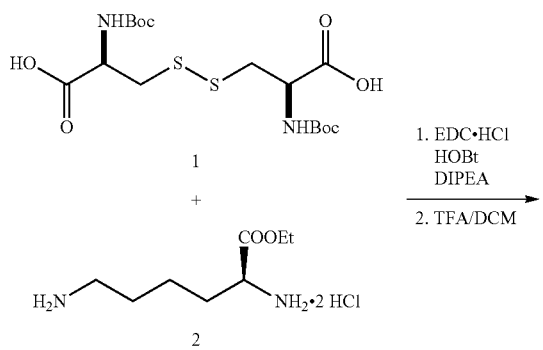

-continued
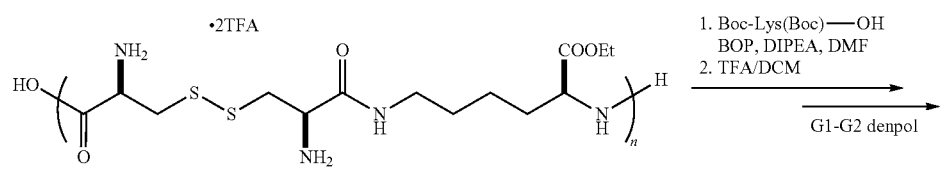
3
Mn - 12~15 kDa, PDI = 1.6~1.9
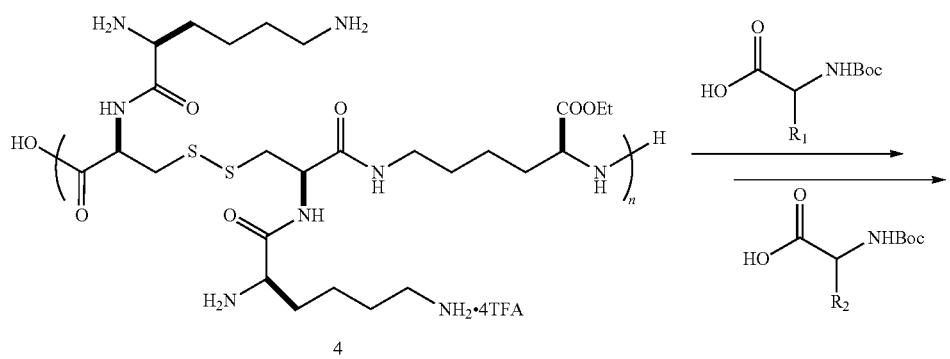
4
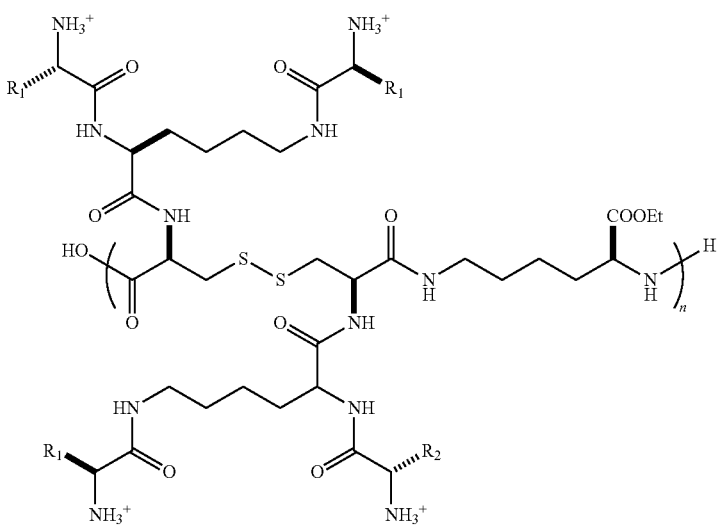
5
(G1 Denpol as example)
R₁ (hydrophilic):
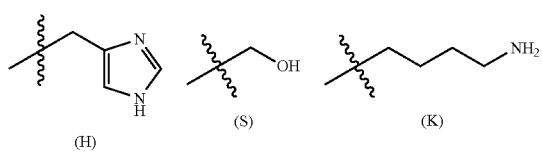
(H)  (S)  (K)
R₂ (hydrophobic):
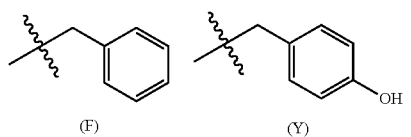
(F)  (Y)

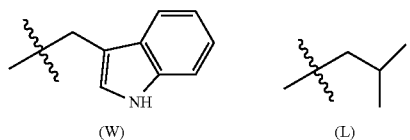

(W)      (L)

Denpol Library:
G1: 75K-25F, 75K-25W, 75H-25F, 75H-25W, 75H-25Y
G2: 25K-75F, 50K-50F, 50H-50F, 75K-25F, 75K-25W, 75S-25F 75H-25F, 75H-25W, 75H-25Y, 75H-25L, 88H-12F, 88H-12W The polymer backbone was synthesized by step-growth polymerization of dicysteine 1 and L-lysine 2 using 1-ethyl-3-(3-dimethylaminopropyl)carbodiimide ("EDC") as the coupling reagent (polymer $M_n$~15 kD, PDI~1.8 by GPC). Dicysteine was introduced into the polymer backbone as the environmentally responsive motif for facilitated siRNA release in the cytoplasm. Onto the linear polymer backbone 3, L-lysine-based dendron was then grown generation by generation through solution-phase peptide coupling. Finally, after reaching the desired generation 4, the outer layer of the dendron was functionalized by a combination of one hydrophilic and one hydrophobic amino acid at various ratios 5. Using the combinatorial synthesis method, three hydrophilic amino acids (lysine: K, serine: S, and histidine: H) and four hydrophobic amino acids (tryptophan: W, phenylalanine: F, tyrosine: Y, and leucine: L) were used to quickly generate a small focused library of G1-G2 amphiphilic denpols. For simplicity, the denpols were named after the generation of the dendron and the compositions of the amphiphilic amino acids on the outer layer using one-letter amino acid codes. For example, G2 75H-25W represents a denpol carrying multivalent second-generation denrons having 75 mol % histidine and 25 mol % tryptophan incorporated on the outer layer.

Denpol Synthesis and Characterization.

Following SCHEME 5, polymer backbone 1, G1 Denpol 2 and G2 Denpol 3 were generated, which was further functionalized to make functionalized G2 Denpol:

SCHEME 5

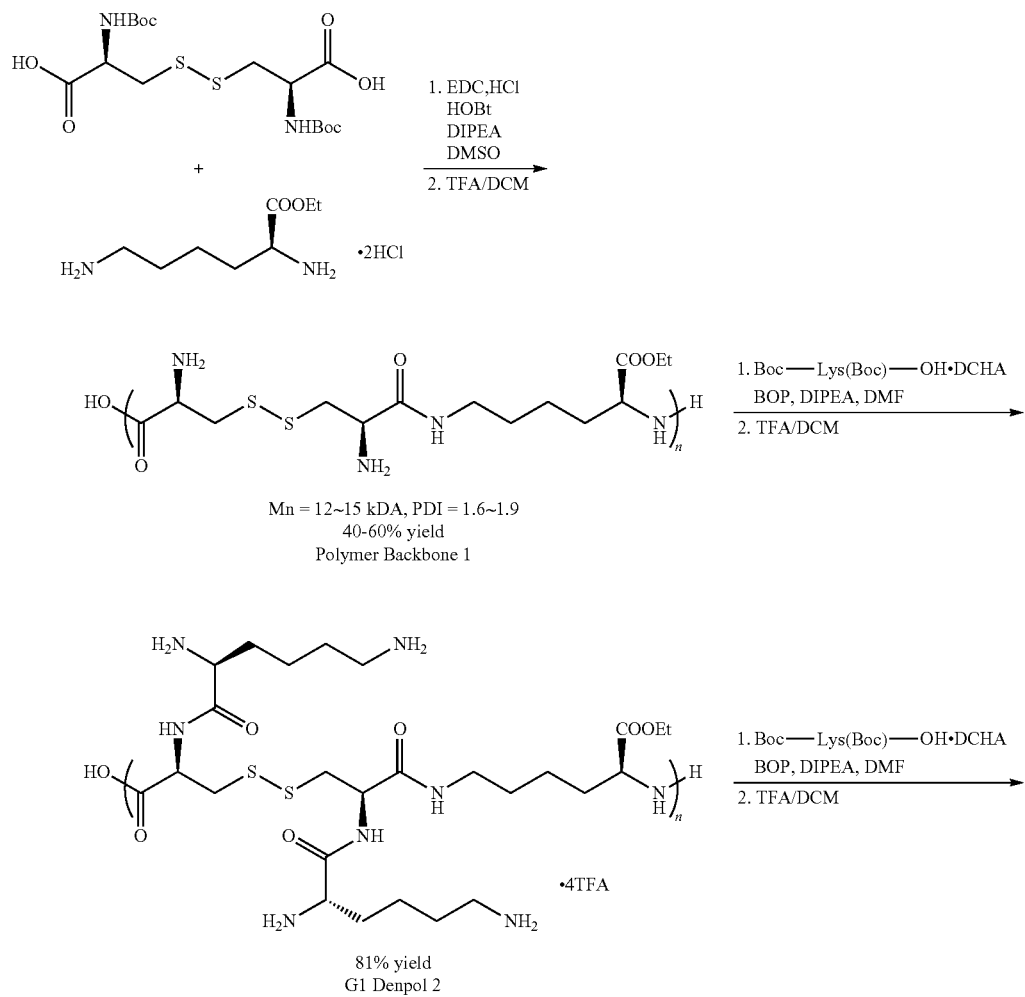

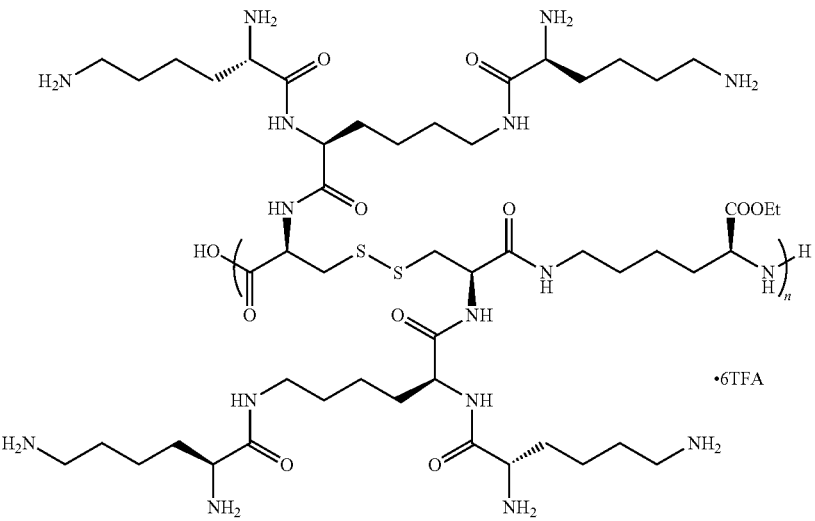
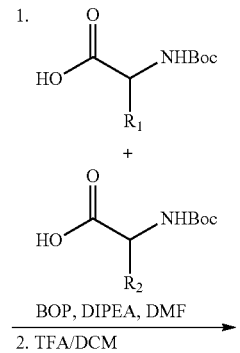
85% yield
G2 Denpol 3
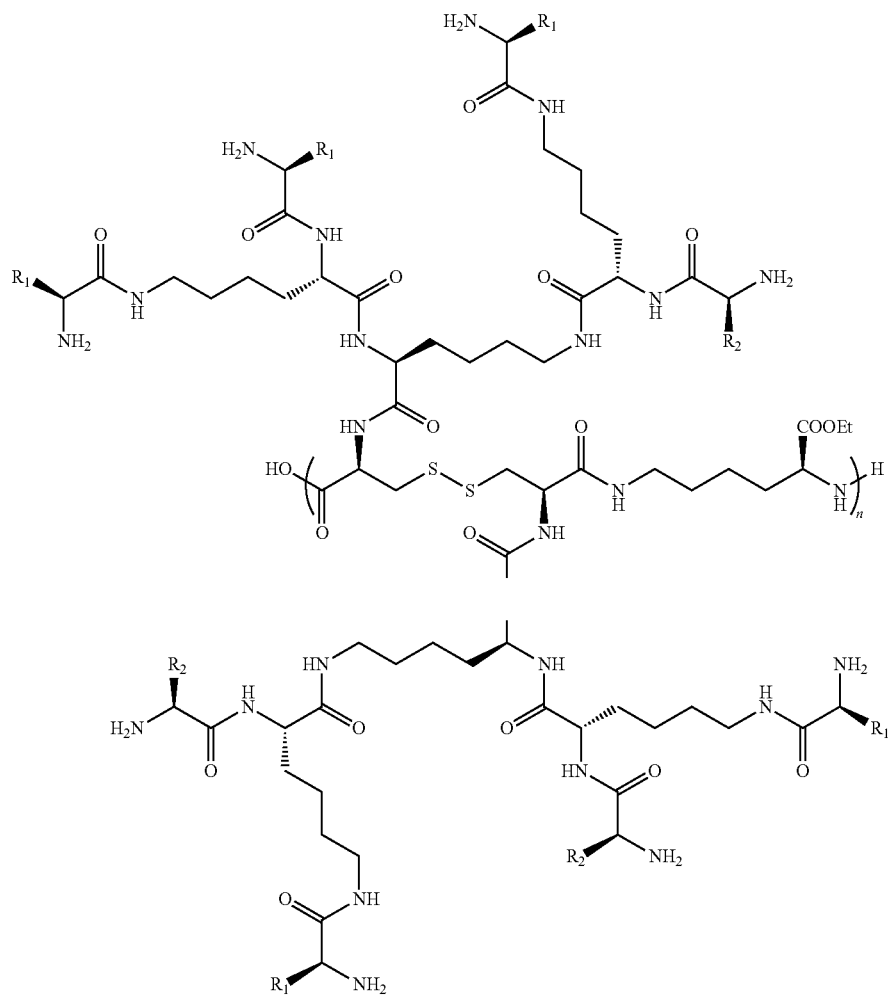
Functionalized G2 Denpol

Synthesis of Polymer Backbone 1:

H-Lys-OEt.2HCl (2.471 g, 10.0 mmol), (Boc-Cys-OH)$_2$ (4.405 g, 10.0 mmol) were dissolved in DMSO (15.0 mL) in a wide, shallow glass jar. Once the amino acids were dissolved after vigorous stirring, EDC.HCl (11.502 g, 60.0 mmol), HOBt (2.973 g, 22 mmol), and DIPEA (4.355 mL, 25 mmol) were added to the reaction. The reaction vessel was capped and the mixture was left to stir at ambient temperature for 48 hours. One drop of the crude reaction mixture was diluted with DMF and subjected to GPC analysis. Crude polymer was precipitated by adding the reaction mixture to water and then separated by centrifugation. After completely removing water, the polymer was dissolved in trifluoroacetic acid ("TFA") (50 mL) and DCM (10 mL) and left to stir for 24 hours at ambient temperature. After deprotection, the solvent was removed with rotary evaporation and the resulting solid was re-dissolved in methanol. Deprotected polymer was then obtained by precipitation of the methanol solution in diethyl ether. The polymer was further purified by dialysis against methanol for 2 days with MWCO 3,500. After removing methanol in vacuo, the polymer was lyophilized to give a white powder. (3.30 g, 56% yield) $^1$H NMR (500 MHz, D$_2$O): δ 4.52-4.34 (2H), 4.34-4.18 (3H), 3.47-3.12 (6H), 2.0-1.86 (1H), 1.86-1.68 (1H), 1.68-1.52 (2H), 1.52-1.37 (2H), 1.34-1.23 (t, 3H). The protected polymer was characterized by GPC with 0.1% LiBr DMF as the eluent, poly(ethylene glycol) ("PEG") standards were used as the reference: $M_n$=15.0 kDa, $M_w/M_n$=1.76.

Synthesis of G1 Denpol 2.

In a round bottom flask (25 Ml), 2.20 g of 1 (3.72 mmol, 1 equiv) and 3.93 g boc-lys(boc)-OH.DCHA (7.44 mmol, 2 equiv) were dissolved in DMF (10 mL). After which, DIPEA (8.18 mmol, 2.2 equiv) (1.42 mL) and BOP (8.18 mmol, 2.2 equiv) (3.62 g) were added. The reaction was left to stir overnight at ambient temperature. The protected denpol was then precipitated by pouring the solution into water. After completely removing water, the polymer was dissolved in a TFA/DCM solution (3:1) (20 mL) and stirred overnight at ambient temperature. Excess TFA and DCM were removed in vacuo. The resulting polymer was redissovled in methanol and precipitated in ether. The precipitate was dissolved in water and lyophilized to give a white powder. (3.29 g, 81% yield) $^1$H NMR (500 MHz, D$_2$O): δ 4.74-4.55 (2H), 4.38-4.24 (1H), 4.24-4.13 (2H), 4.03 (2H), 3.28-2.88 (10H), 1.97-1.26 (18H), 1.23 (3H).

Synthesis of G2 Denpol 3.

In a round bottom flask (25 mL), 2.00 g of 2 (1.81 mmol, 1 equiv) and 3.81 g boc-lys(boc)-OH.DCHA (7.22 mmol, 4 equiv) were dissolved in DMF (10 mL). After which, DIPEA (7.60 mmol, 4.2 equiv) (1.30 mL) and BOP (7.60 mmol, 4.2 equiv) (3.36 g) were added. The reaction was left to stir overnight at ambient temperature. The protected denpol was then precipitated by pouring the solution into water. After completely removing water, the polymer was dissolved in a TFA/DCM solution (3:1) (20 mL) and stirred overnight at ambient temperature. Excess TFA and DCM were removed in vacuo. The resulting polymer was re-dissolved in Methanol and precipitated in ether. The precipitate was dissolved in water and lyophilized to give a white powder. (3.20 g, 85% yield). $^1$H NMR (500 MHz, D$_2$O): δ 4.74-4.63 (1H), 4.63-4.49 (1H), 4.42-4.23 (3H), 4.23-4.10 (2H), 4.06-3.96 (2H), 3.90 (2H), 3.29-2.89 (18H), 1.98-1.26 (42H), 1.23 (3H).

G1 Denpol:

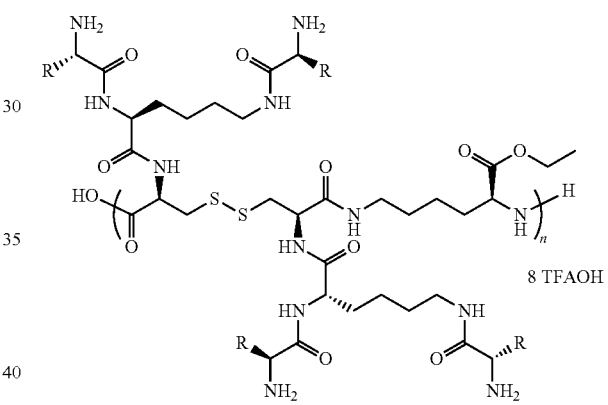

G1 75K-25F: white powder, 92% yield, $^1$H NMR (D$_2$O): δ 7.37 (3H), 7.24 (2H), 4.73-3.84 (11H), 3.33-2.84 (18H), 2.01-1.12 (39H). Percent functionalization by $^1$H NMR: 75% K-23% F. G1 75K-25W: white powder, 71% yield, $^1$H NMR (D$_2$O): δ 7.84-6.93 (5H), 4.48-3.83 (11H), 3.50-2.66 (18H), 2.13-0.77 (39H). Percent functionalization by $^1$H NMR: 75% K-19% W.

G1 75H-25F: white powder, 87% yield, $^1$H NMR (D$_2$O): δ 8.66 (3H), 7.67-6.92 (8H), 4.64-3.90 (11H), 3.49-2.77 (18H), 2.06-1.04 (21H). Percent functionalization by $^1$H NMR: 68% H-26% F.

G1 75H-25W: white powder, 91% yield, $^1$H NMR (D$_2$O): δ 8.79-8.32 (3H), 7.73-6.84 (8H), 4.66-3.88 (11H), 3.46-2.87 (18H), 1.98-1.06 (21H). Percent functionalization by $^1$H NMR: 75% H-25% W.

G1 75H-25Y: white powder, 87% yield, $^1$H NMR (D$_2$O): δ 8.64 (3H), 7.48-7.24 (3H), 7.17-6.93 (2H), 6.91-6.67 (2H), 4.67-3.96 (11H), 3.45-2.92 (18H), 1.95-1.06 (21H). Percent functionalization by $^1$H NMR: 70% H-24% Y.

G2 Denpol:

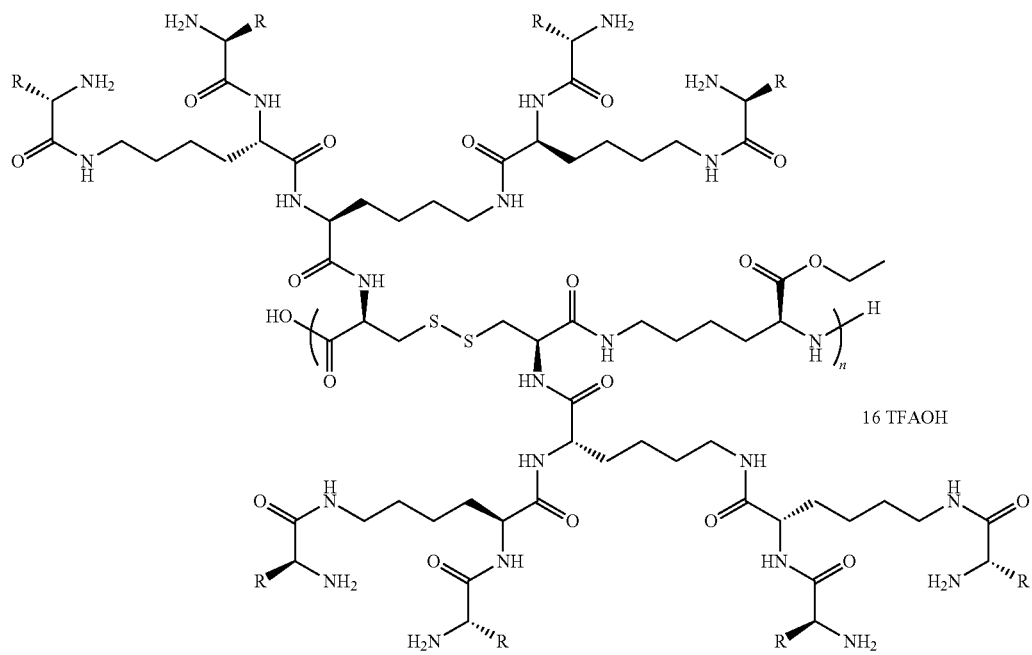

16 TFAOH

G2 25K-75F: white powder, 67% yield, $^1$H NMR (D$_2$O): δ 7.35 (18H), 7.24 (12H) 4.66-3.83 (19H), 3.33-2.80 (34H), 2.01-0.93 (57H). Percent functionalization by $^1$H NMR: 25% K-62% F.

G2 50K-50F: white powder, 63% yield, $^1$H NMR (D$_2$O): δ 7.38 (12H), 7.27 (8H), 4.69-3.88 (19H), 3.40-2.86 (34H), 2.05-0.98 (69H). Percent functionalization by $^1$H NMR: 50% K-45% F.

G2 50H-50F: white powder, 79% yield, $^1$H NMR (D$_2$O): δ 8.48 (4H), 7.28-6.93 (24H), 4.67-3.77 (19H), 3.33-2.60 (34H), 1.86-0.76 (45H). Percent functionalization by $^1$H NMR: 41% H-41% F.

G2 75K-25F: white powder, 84% yield, $^1$H NMR (D$_2$O): δ 7.33 (6H), 7.23 (4H), 4.73-3.87 (19H), 3.36-2.80 (34H), 2.07-0.92 (81H). Percent functionalization by $^1$H NMR: 75% K-23% F.

G2 75K-25W: white powder, 92% yield, $^1$H NMR (D$_2$O): δ 7.63-6.91 (10H), 4.62-3.79 (19H), 3.53-2.61 (34H), 2.09-0.68 (81H). Percent functionalization by $^1$H NMR: 75% K-23% W.

G2 75S-25F: white powder, 93% yield, $^1$H NMR (D$_2$O): δ 7.34 (6H), 7.23 (4H), 4.73-4.02 (19H), 4.02-3.81 (12H), 3.31-2.85 (22H), 1.93-0.98 (45H). Percent functionalization by $^1$H NMR: 73% S-22% F.

G2 75H-25F: white powder, 69% yield, $^1$H NMR (D$_2$O): δ 8.50 (6H), 7.31 (16H), 4.87-3.99 (19H), 3.44-2.83 (34H), 2.00-1.11 (45H). Percent functionalization by $^1$H NMR: 75% H-25% F.

G2 75H-25W: white powder, 78% yield, $^1$H NMR (D$_2$O): δ 8.64 (6H), 7.74-6.78 (16H), 4.46-3.86 (19H), 3.47-2.63 (34H), 2.04-0.80 (45H). Percent functionalization by $^1$H NMR: 75% H-21% W.

G2 75H-25Y: white powder, 76% yield, $^1$H NMR (D$_2$O): δ 8.66 (6H), 7.38 (6H), 7.05 (4H), 6.76 (4H), 4.63-3.95 (19H), 3.48-2.77 (34H), 1.97-1.05 (45H). Percent functionalization by $^1$H NMR: 75% H-20% Y.

G2 75H-25L: white powder, 79% yield, $^1$H NMR (D$_2$O): δ 8.68 (6H), 7.39 (6H), 4.48-3.84 (19H), 3.48-2.87 (30H), 1.99-1.10 (51H), 0.90 (12H). Percent functionalization by $^1$H NMR: 75% H-22% L.

G2 88H-12F: white powder, 69% yield, $^1$H NMR (D$_2$O): δ 8.77-8.25 (7H), 7.31 (10H), 7.20 (2H), 4.72-4.01 (19H), 3.42-2.83 (34H), 1.92-1.09 (45H). Percent functionalization by $^1$H NMR: 83% H-15% F.

G2 88H-12W: white powder, 84% yield, $^1$H NMR (D$_2$O): δ 8.72-8.26 (7H), 7.63-6.88 (12H), 4.74-3.96 (19H), 3.43-2.70 (34H), 1.94-1.06 (45H). Percent functionalization by $^1$H NMR: 88% H-12% W.

G2 88H-12Y: white powder, 76% yield, $^1$H NMR (D$_2$O): δ 8.80-8.50 (7H), 7.41 (7H), 7.10 (2H), 6.95-6.72 (2H), 4.66-4.00 (19H), 3.51-2.82 (34H), 1.89-1.18 (45H). Percent functionalization by $^1$H NMR: 86% H-11% Y.

PEGylated Denpol Synthesis:

By slightly modifying the denpol synthesis procedure above, PEGylated denpols were generated. 5% PEG denpol can be synthesized by following the reactions presented in SCHEME 6. Moreover, additional percentages of PEG (e.g., 10% or 20%) were synthesized by using SCHEME 6 but with a different molar ratio of PEG5000 for incorporation.

SCHEME 6
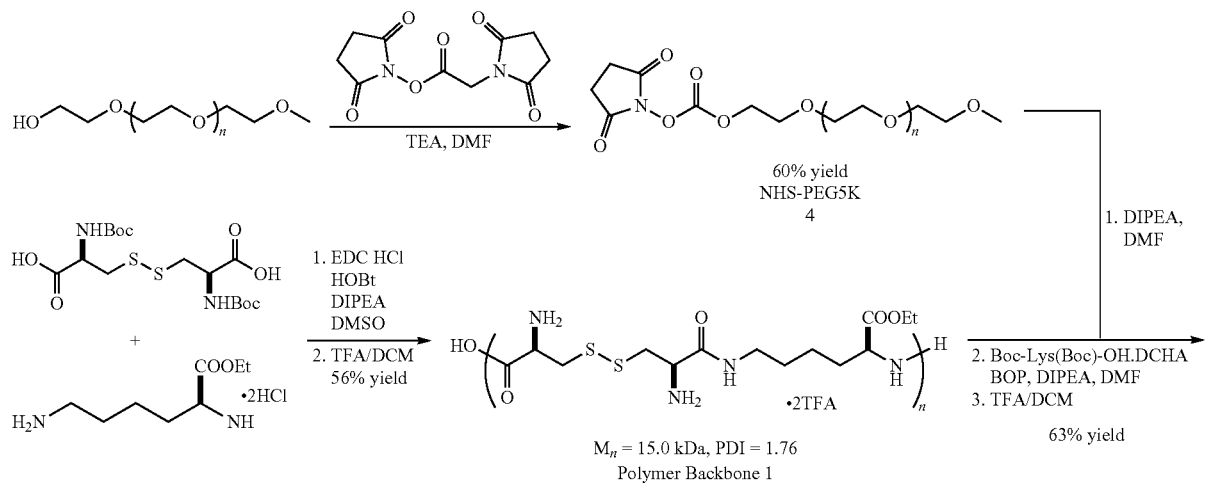
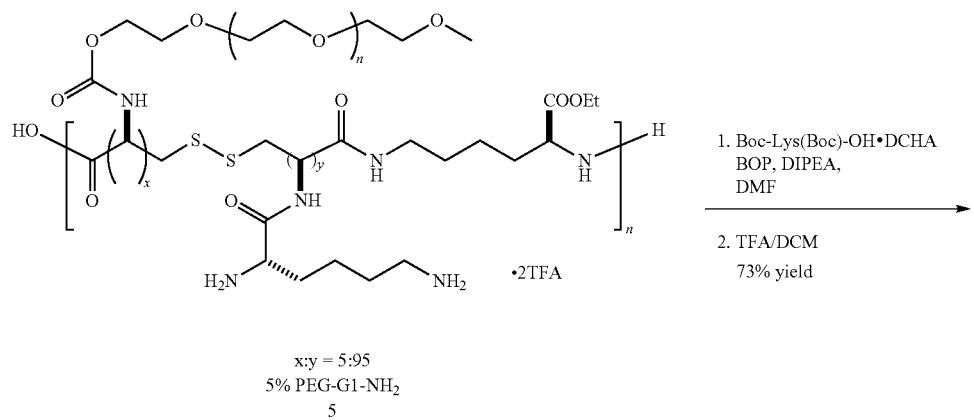
x:y = 5:95
5% PEG-G1-NH$_2$
5
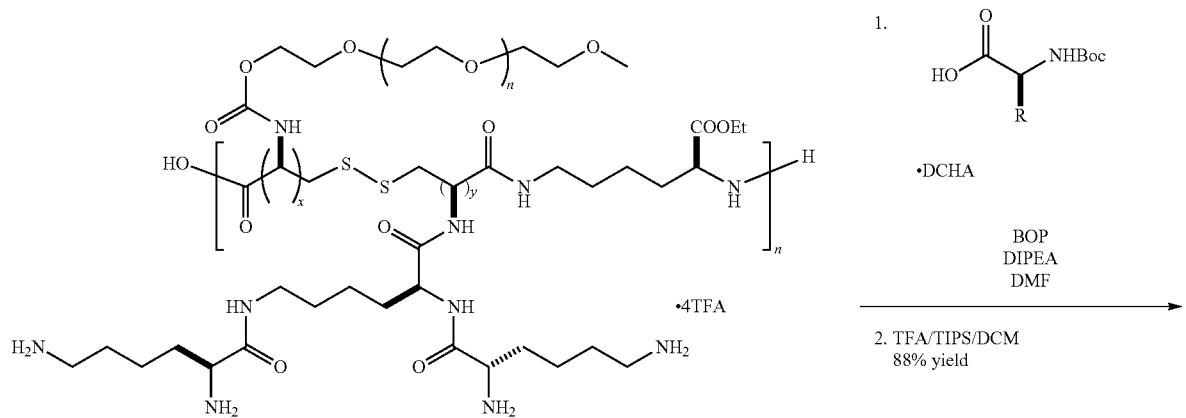
x:y = 5:95
5% PEG-G2-NH$_2$
6

-continued

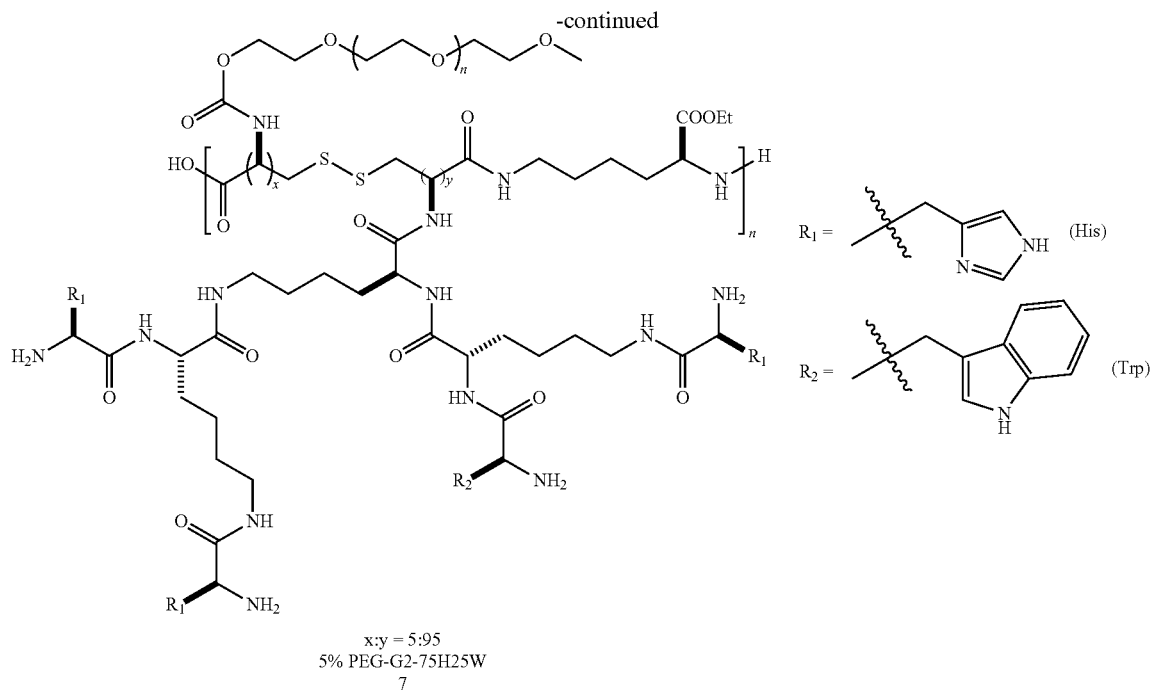

x:y = 5:95
5% PEG-G2-75H25W
7

Synthesis of NHS-PEG5k 4:

Under nitrogen, 17.010 g (3.00 mmol, 1 equiv) of poly(ethylene glycol) methyl ether (PEG5k, $M_n$=5000, Sigma-Aldrich) and triethylamine (TEA) (0.460 mL, 3.3 mmol, 1.1 equiv) were dissolved in 30 mL anhydrous DCM in a 100 mL round bottom flask. The solution was stirred for 30 min on ice. Under nitrogen, N,N'-disuccinimidyl carbonate (1.153 g, 4.50 mmol, 1.5 equiv) was suspended in 5 mL anhydrous DCM in another flask. Using an ice bath, the PEG5k/TEA solution was added dropwise to the flask containing N,N'-Disuccinimidyl carbonate under nitrogen. The reaction was left to stir for 30 min on ice and another 24 hours at room temperature. After the reaction, the solution was diluted with chloroform and washed with ice cold brine (3×). The organic layer was dried over sodium sulfate and all solvents were removed in vacuo to afford the NHS-PEG5K as a white solid (10.2 g, 60%). $^1$H NMR (500 MHz, CDCl$_3$): δ 4.50 (m, 2H), 4.38-4.52 (m, 496H), 3.42 (s, 3H), 2.88 (s, 4H).

Synthesis of Polymer Backbone 1:

H-Lys-OEt.2HCl (2.471 g, 10.0 mmol), (Boc-Cys-OH)$_2$ (4.405 g, 10.0 mmol) were dissolved in DMSO (15.0 mL) in a wide, shallow glass jar. Once the amino acids were dissolved after vigorous stirring, EDC.HCl (11.502 g, 60.0 mmol), HOBt (2.973 g, 22 mmol), and DIPEA (4.355 mL, 25 mmol) were added to the reaction mixture. The reaction vessel was capped and the mixture was left to stir at room temperature for 48 hours. One drop of the crude reaction mixture was diluted with DMF and subjected to GPC analysis. Crude polymer was precipitated by adding the reaction mixture to water and then separated by centrifugation. After the water was completely removed, the polymer was dissolved in 50 mL trifluoroacetic acid (TFA) and 10 mL DCM and left to stir for 24 hours at room temperature. After deprotection, the solvent was removed with rotary evaporation and the resulting solid was re-dissolved in methanol. Deprotected polymer was then obtained by precipitating the methanol solution in diethyl ether. The polymer was further purified by dialysis against methanol for 2 days with MWCO 3,500. After removing the methanol in vacuo, the polymer was dissolved in water and lyophilized to give a white powder. (3.30 g, 56% yield) $^1$H NMR (500 MHz, D$_2$O): δ 4.52-4.34 (2H), 4.34-4.18 (3H), 3.47-3.12 (6H), 2.0-1.86 (1H), 1.86-1.68 (1H), 1.68-1.52 (2H), 1.52-1.37 (2H), 1.34-1.23 (t, 3H). The protected polymer was characterized by GPC with 0.1% LiBr DMF as the eluent, poly(ethylene glycol) (PEG) standards were used as the reference: $M_n$=15.0 kDa, $M_w/M_n$=1.76.

Synthesis of 5% PEG-G1-NH$_2$ Denpol 5.

Under nitrogen and in an oven-dried 10 mL round bottom flask, polymer backbone 1 (100 mg, 0.160 mmol repeating units, 1.00 equiv) and NHS-PEG5k 4 (80 mg, 0.016 mmol, 0.10 equiv) were dissolved in 2 mL anhydrous DMF followed by addition of 14 μL DIPEA (0.080 mmol, 0.5 equiv). The reaction was left to stir under nitrogen overnight. Without purification, the reaction was diluted with 2.0 mL DMF, followed by the addition of Boc-lys(boc)-OH.DCHA (168 mg, 0.320 mmol, 2.00 equiv), BOP (142 mg, 0.320 mmol, 2.00 equiv) and DIPEA (56 μL, 0.320 mmol, 2.00 equiv). The reaction was stirred at room temperature for another 24 hours. Afterwards, the solution was diluted with methanol and dialyzed against methanol for 2 days with MWCO 8000 membrane. After removing the methanol in vacuo, the protected polymer was dissolved in a 5 mL TFA/DCM solution (5:1) and stirred overnight at room temperature. Excess TFA and DCM was removed in vacuo, the resulting polymer was re-dissolved in methanol and dialyzed against methanol again with MWCO 8000 membrane. After removing the methanol, the deprotected polymer was dissolved in water and lyophilized to give a white powder. (162 mg, 63% yield)$^1$H NMR (500 MHz, D$_2$O): δ 4.40 (1H), 4.24 (2H), 4.11 (2H), 3.80-3.60 (77H, PEG, —OCH$_2$CH$_2$O—, 7 mol %), 3.42 (0.42H, PEG, —OMe, 7 mol %), 3.31-3.00 (8H), 2.05-1.33 (16.48H, lys-dendron, 92 mol %), 1.28 (3H).

Synthesis of 5% PEG-G2-NH$_2$ denpol 6.

In a 5 mL round bottom flask, 5% PEG-G1-NH2 5 (150 mg, 0.094 mmol, 1.00 equiv) and boc-lys(boc)-OH.DCHA (198.4 mg, 0.376 mmol, 4.00 equiv) was dissolved in 5 mL DMF, followed by the addition of DIPEA (69 µL, 0.395 mmol, 4.20 equiv) and BOP (174.7 mg, 0.395 mmol, 4.2 equiv). The reaction was left to stir overnight at room temperature. Afterwards, the solution was diluted with methanol and dialyzed against methanol for 2 days with MWCO 8000 membrane. After removing the methanol in vacuo, the protected polymer was dissolved in a 5 mL TFA/DCM solution (5:1) and stirred at overnight at room temperature. Excess TFA and DCM was removed in vacuo, the resulting polymer was redissolved in methanol and dialyzed against methanol again with MWCO 8000 membrane. After removing MeOH, the deprotected polymer was dissolved in water and lyophilized to give a white powder. (195 mg, 73% yield). $^1$H NMR (500 MHz, D$_2$O): δ 4.60 (1H), 4.40-4.20 (5H), 4.01 (1.82H), 3.89 (1.89H), 3.83-3.50 (77.8H, PEG, —OCH$_2$CH$_2$O—), 3.38 (0.46H, PEG, —OMe), 3.31-3.05 (7.4H), 2.98 (9.15H), 2.05-1.33 (39.8H, lys-dendron), 1.25 (3H).

Synthesis of 5% PEG-G2-75H25W 7:

In a one drum glass vial, 5% PEG-G2-NH$_2$ 6 (30 mg, 0.0105 mmol, 1.00 equiv), Boc-His(boc)-OH.DCHA (33.8 mg, 0.0630 mmol, 6.00 equiv) and Boc-Trp(boc)-OH (8.5 mg, 0.0210 mmol, 2.00 equiv) were dissolved in DMF (1.5 mL), followed by the addition of DIPEA (15 µL, 0.0861 mmol, 8.20 equiv) and BOP (38.1 mg, 0.0861 mmol, 8.20 equiv). The reaction was left to stir at rt for 24 hours. Protected denpol was purified by dialysis against methanol with 8000 MWCO membrane. After removing the methanol, the solid was dissolved in TFA (3 mL), DCM (1 mL) and triisopropylsilane (0.1 mL) as the scavenger. After stirring overnight, excess TFA and DCM were removed in vacuo, the resulting polymer was re-dissolved in methanol and dialyzed against methanol with a MWCO 8000 membrane. After removing the methanol, the deprotected polymer was dissolved in water and lyophilized to give a white powder. (40.7 mg, 88% yield). $^1$H NMR (500 MHz, D$_2$O): δ 8.05-7.70 (5H, His), 7.60-6.80 (13.8H, His+Trp), 4.60 (1.2H), 4.40-4.00 (16H), 3.83-3.50 (71.3H, PEG, —OCH$_2$CH$_2$O—), 3.38 (0.68H, PEG, —OMe), 3.31-2.80 (31.6H), 1.95-0.90 (45H, lys-dendron).

Figure 6A:
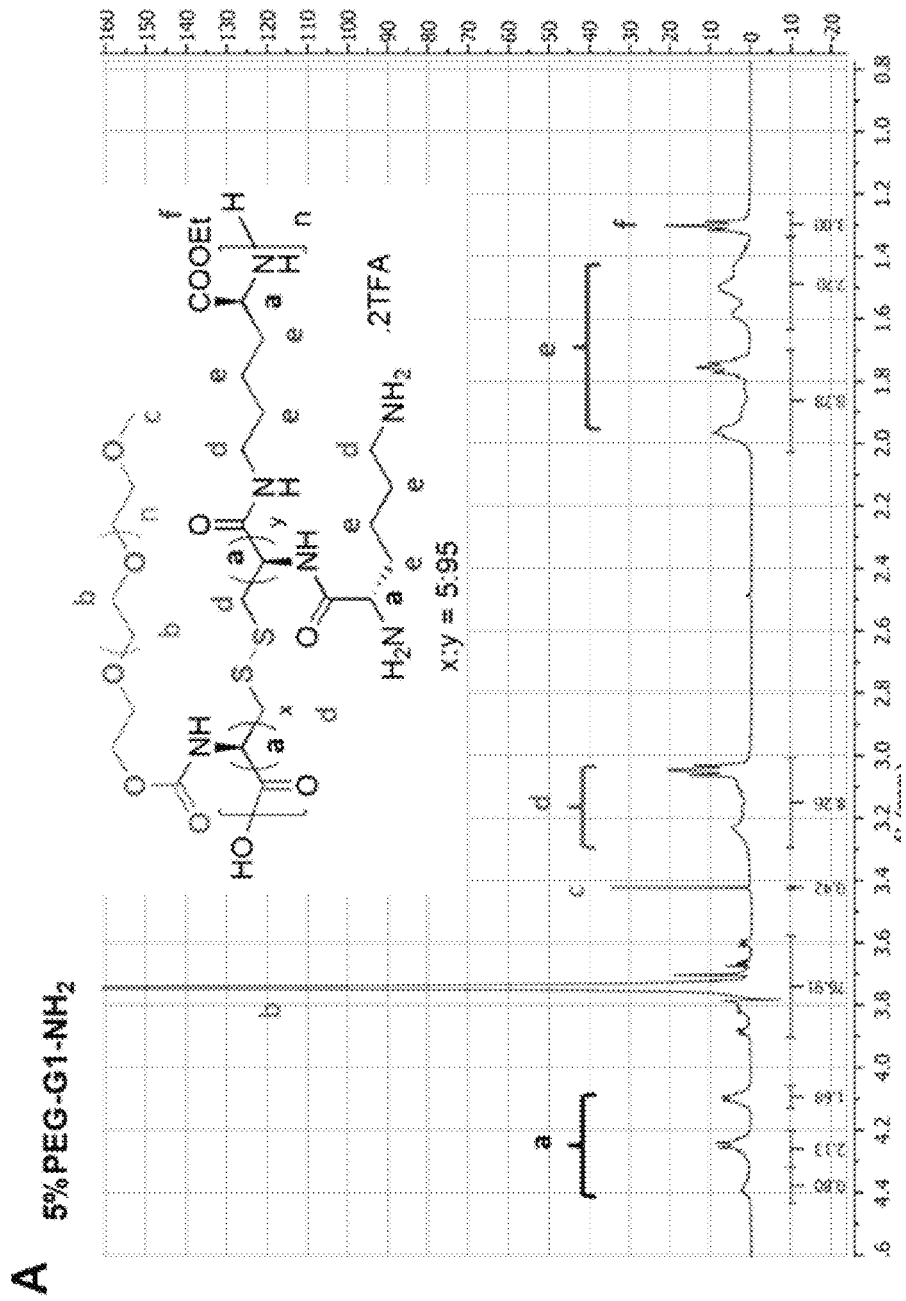
FIG. 6A-B provides representative $^1H$ NMR peak assignments for PEGylated denpols: (A) 5% PEG-G1-$NH_2$, and (B) 5% PEG-G2-75H25W.
Figure 6B:
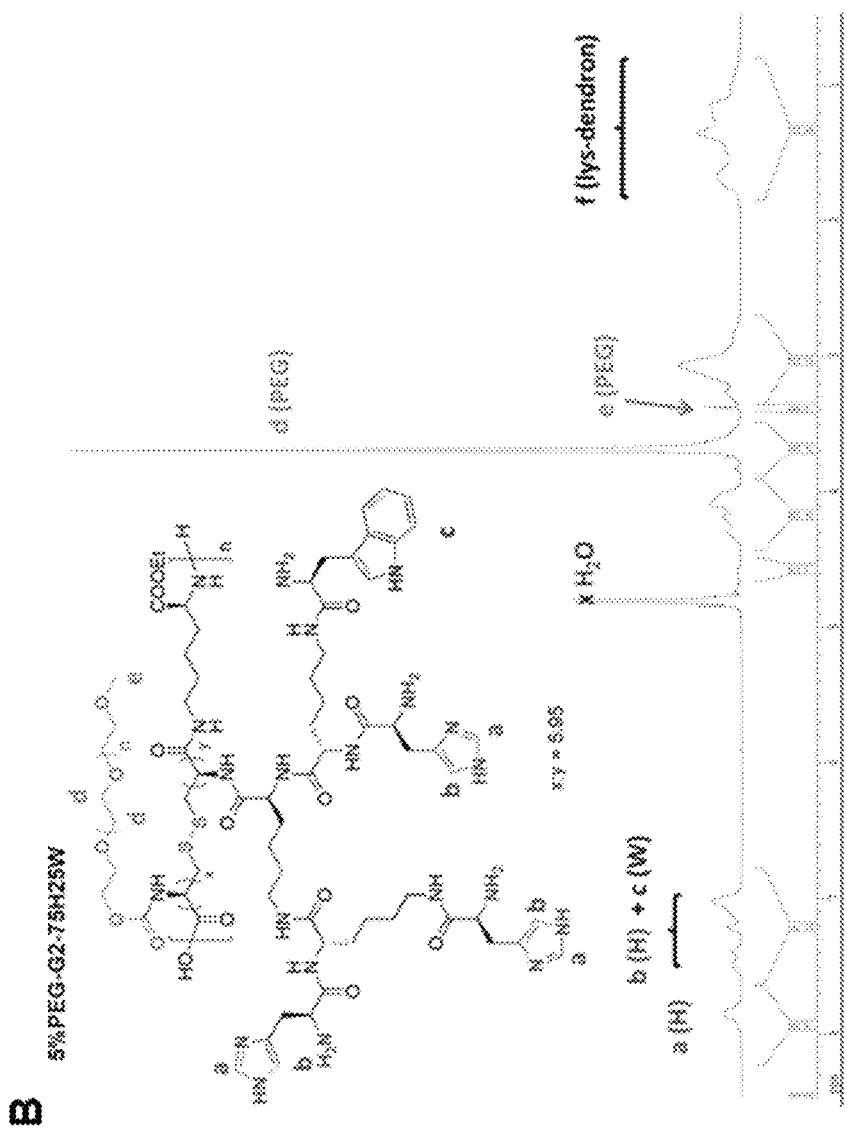

PEGylation Ratio and Functionalization Ratio of Different Denpols:

The ratio of PEG incorporation was calculated by comparing the methyl peak (—OCH$_3$) and methylene peaks (—OCH$_2$CH$_2$O—) of the PEG with ethyl ester peak (—COOCH$_2$CH$_3$) of the polymer backbone in G1 denpol (see FIG. 6A). The functionalization ratio of histidine and tryptophan was calculated by comparing the characteristic side chain peak with the aliphatic region in lysine (see FIG. 6B). TABLE 1 summarizes the characterization of the three different PEG denpols.

TABLE 1

Functionalization ratio of different PEGylated denpols

| Sample | PEG 5k | Dendron | His | Trp |
|---|---|---|---|---|
| 5% PEG-G2-75H25W | 7% | 92% | 68% | 24% |
| 10% PEG-G2-75H25W | 12% | 86% | 75% | 25% |
| 20% PEG-G2-75H25W | 19% | 80% | 69% | 25% |

*All ratios were molar ratio based on $^1$H NMR analysis.

Assessing Denpols/siRNA Complexes.

The binding capability of the denpols with siRNA was initially assayed by using gel electrophoresis, and most denpols could completely complex with siRNA at an N/P ratio from 10~30. The binding strength was further evaluated by competitive binding assays using an anionic polymer, dextran sulfate (DS, MW=25 kD) as the challenger (selected examples are shown in FIG. 7A-C). For this purpose, polyplexes prepared at N/P 40 were incubated with different amount of DS to compete with siRNA. A number of trends were observed in the competitive binding assay: (1) the generation of dendron is important for binding strength to siRNA; (2) the second generation denpol has much stronger binding strength than first generation (see FIG. 7A-B), due to the increased multivalent binding sites from the dendrons; and (3) the composition of amino acids on the outer layer also has a significant impact on the binding capability to siRNA. In our small library of denpols, tryptophan (W) incorporated denpols show the strongest binding to siRNA. For example, no appreciable siRNA release could be observed for G2 75H-25W at S/P up to 30 (FIG. 7C). As previously reported, the indole ring on tryptophan could intercalate into nucleotide base pairs (e.g., see Rajeswari et al., *Biochemistry* 1987, 26, 6825; and Rajeswari et al., *Biochemistry* 1992, 31, 6237). These interactions could account for the increased binding affinity of tryptophan functionalized denpol to siRNA. Lastly, due to the dicysteine building blocks on the polymer backbone, complexed siRNAs can be released from the polyplexes by the addition of a reducing agent. For this assay, different denpol/siRNA polyplexes were treated with glutathione (GSH) at a concentration close to physiological conditions (5 mM). Gel assays demonstrate that siRNA was completely released from most denpols after the GSH treatment (see FIG. 7D). For the tryptophan containing G2 denpol, which has the strongest binding affinity to siRNA, the binding strength was significantly reduced. Presumably, the reduced binding affinity to siRNA after GSH treatment is due to the reduction-triggered degradation of the denpol, which decreases the multivalency for binding. GSH triggered release or exposure to a reducing environment in the cell should be beneficial for intracellular siRNA delivery, by releasing the siRNA from denpol once inside the cell. Both transmission electron microscope ("TEM") and atomic force microscope ("AFM") images show denpol/siRNA polyplexes as spherical nanoparticles with 30-80 nm in diameter (see FIG. 7E-F). Based on dynamic light scattering ("DLS"), most G2 denpols were able to condense with siRNA into nanoparticles with diameter smaller than 100 nm in buffer solution (see FIG. 7G).

Studies to Determine the Size of Denpol/siRNA Polyplexes and PEGylated Denpol/siRNA Polyplexes.

Figure 8:
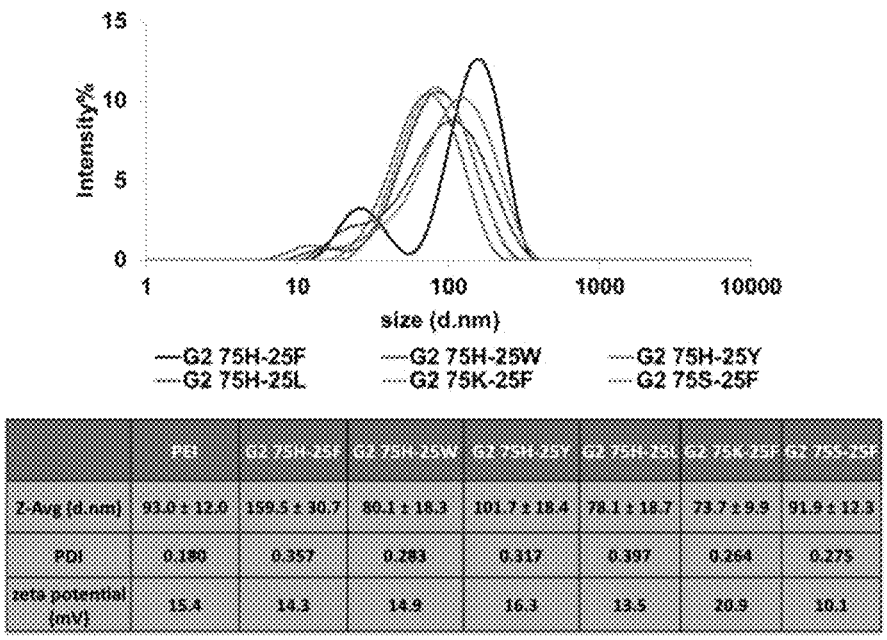
FIG. 8 provides a DLS measurement of different denpol/siRNA complexes.
Figure 9:
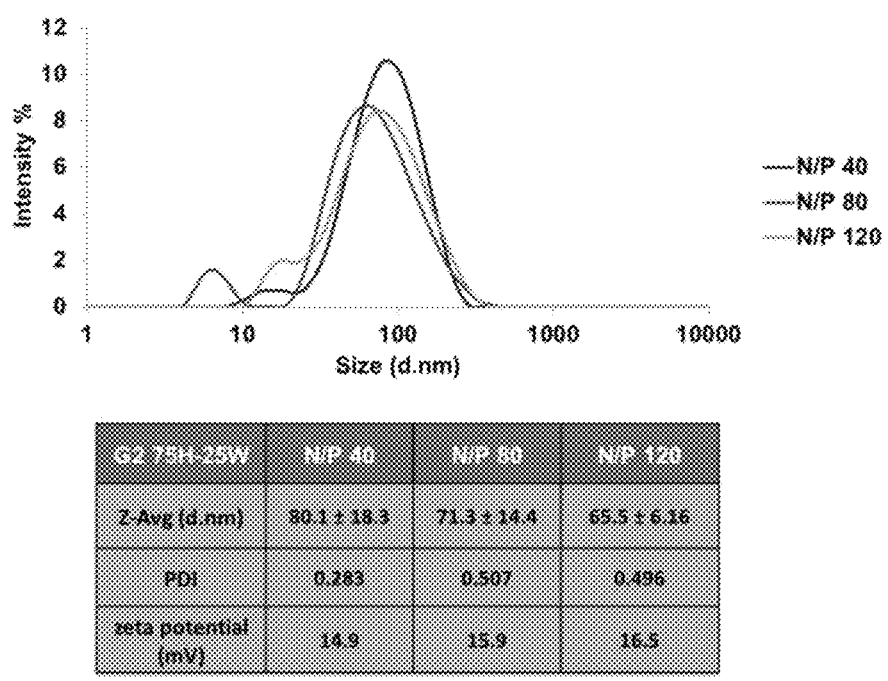
FIG. 9 provides a DLS measurement of G2-75H25W/siRNA complexes at different ratios (Note: Due to the presence of excess free polymer, samples at N/P 80 and 120 are quite polydispersed and the measurement is less accurate.)
Figure 10:
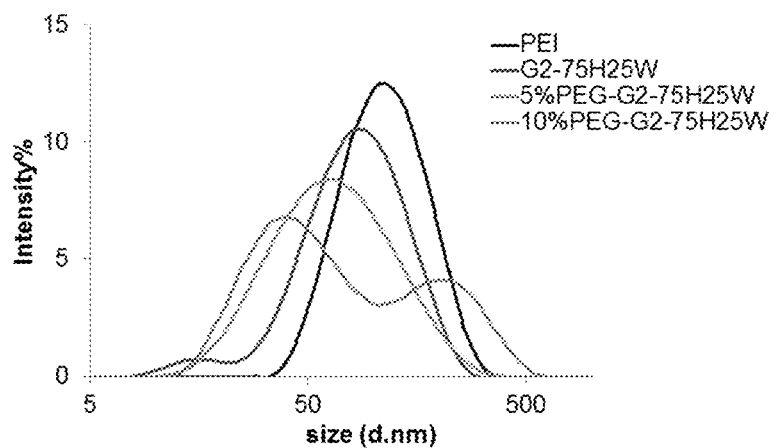
FIG. 10 provides a dynamic light scattering ("DLS") measurement of PEGylated denpol/siRNA complexes.
Figure 11:
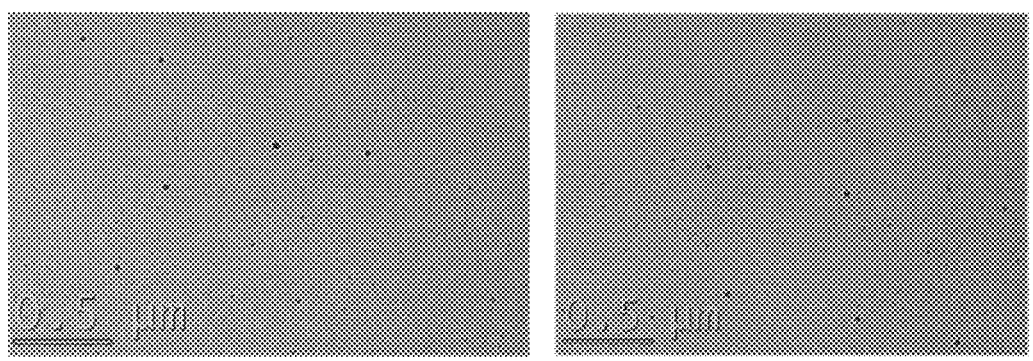
FIG. 11 presents transmission electron microscopy ("TEM") images of G2 75H-25W/siRNA complexes at N/P 10.

The size of the polyplexes was investigated by DLS and TEM. The DLS results showed that most denpols were able to condense siRNA into particles smaller than 100 nm in diameter (see FIG. 8 and FIG. 9). Further, the polyplexes have a moderate positive charge (zeta-potential ~15 mV). The PEGylated denpols form smaller particles with siRNA, but the polydispersity also increases (see FIG. 10). Also the PEGylation greatly reduces the surface charge of the nanoparticle. With 10% PEGylated denpol, the surface charge is near neutral, which therefore increases serum stability of polyplexes and is very beneficial for systemic in vivo delivery. FIG. 12C shows a representative DLS curve of polyplexes prepared from G2 75H-25W at N/P 40 (z-avg=80 nm, PDI=0.317). TEM provides direct visualization of the polyplexes. TEM shows the polyplexes as spherical nanoparticles with diameters ~20-80 nm (see FIG. 11, and FIG. 12A). After GSH treatment, however, no discreet nanoparticle could be observed under TEM (see FIG. 12B), which confirmed the particle responsiveness to reducing agent as observed by gel assay (see FIG. 12D).

siRNA Transfection Studies in NIH 3T3 Cells Using Denpols.

Figure 14:
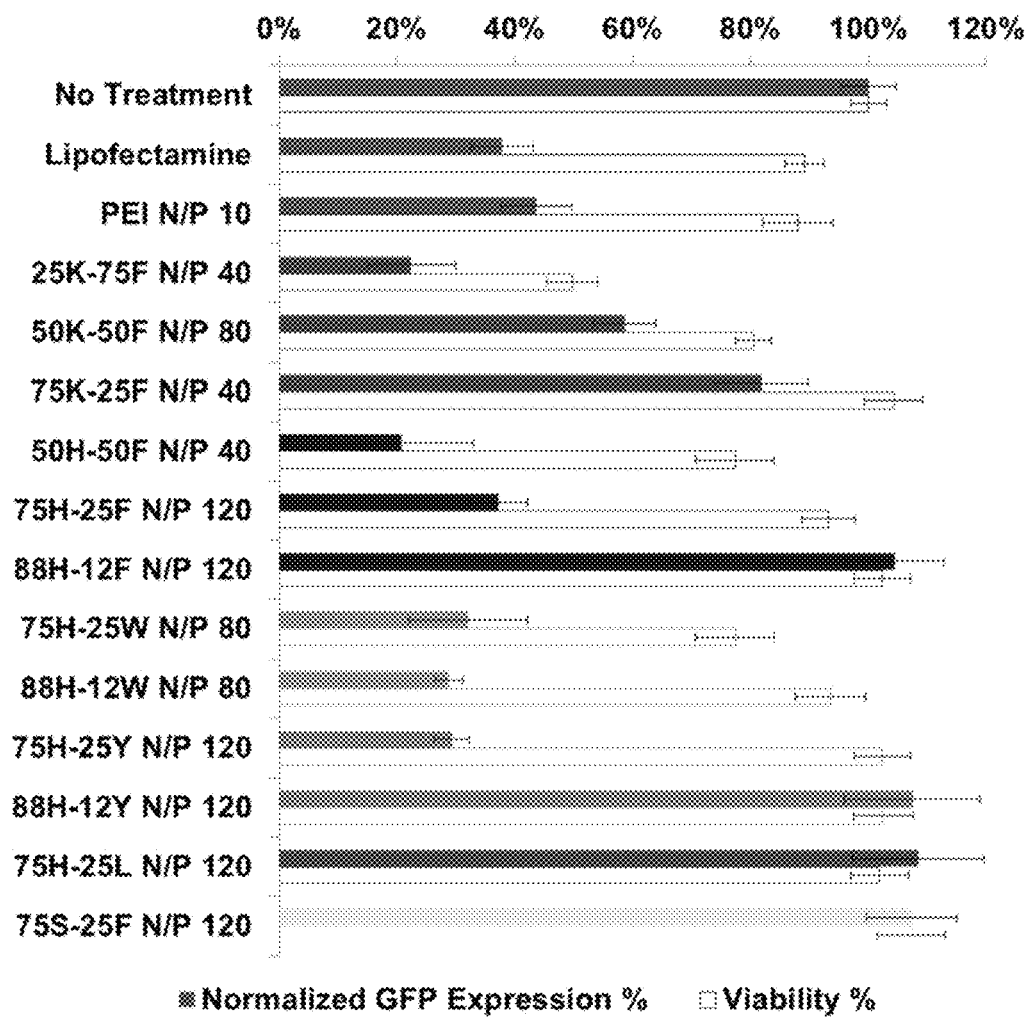
FIG. 14 presents in vitro transfection screening results of select G2 denpols at the optimal N/P ratio by measuring the reduction of expression of green fluorescent protein ("GFP").
Figure 15:
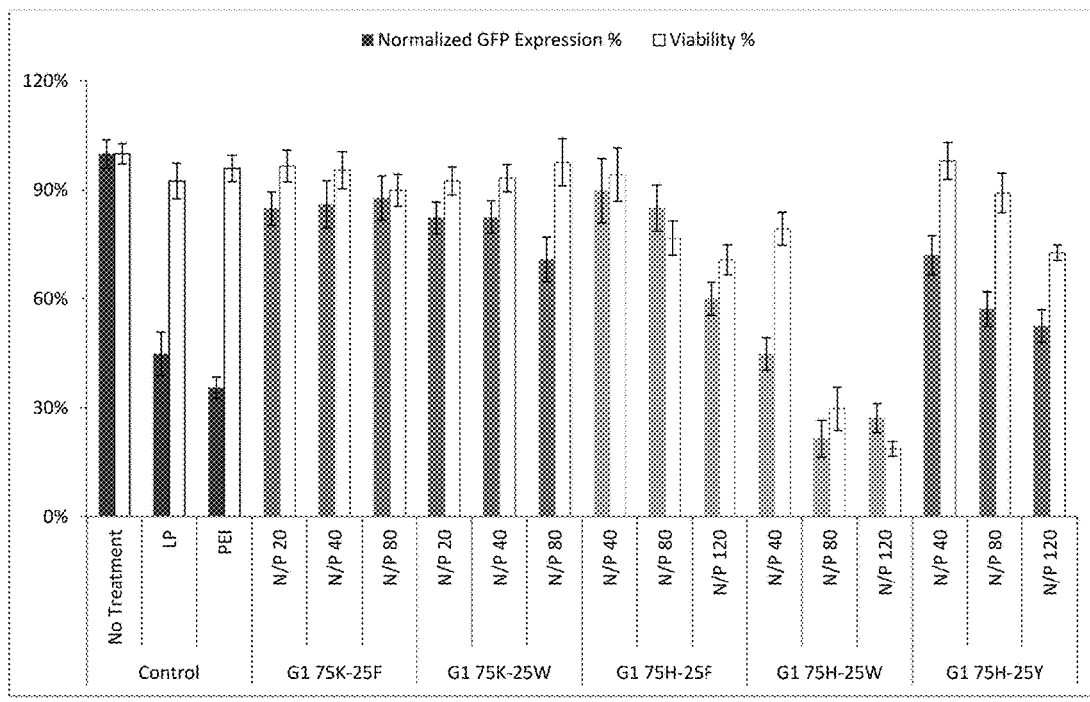
FIG. 15 presents in vitro transfection screening results of G1 denpols at an optimal N/P ratio by measuring the reduction of expression of green fluorescent protein.
Figure 16:
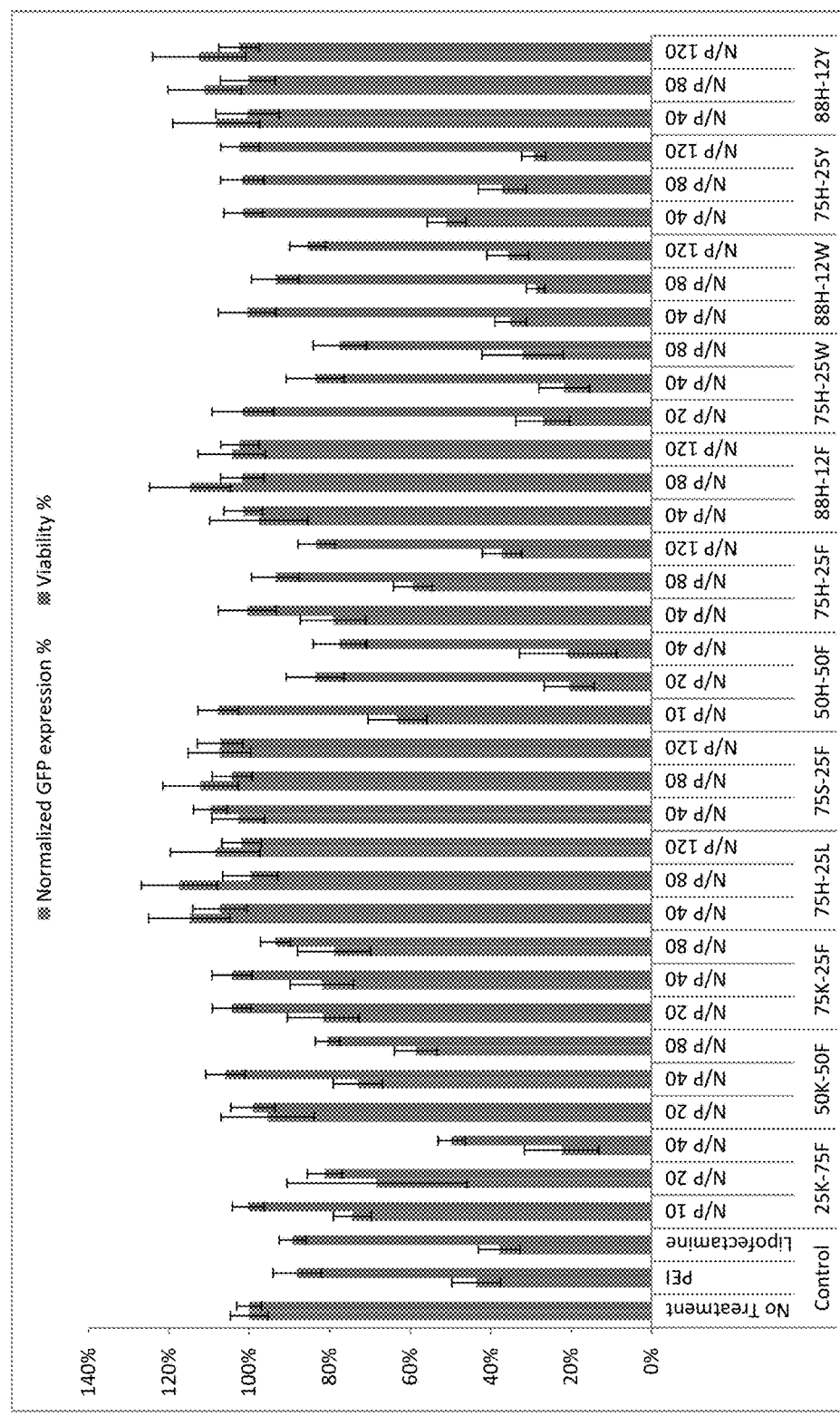
FIG. 16 presents in vitro transfection screening results of G2 denpols at an optimal N/P ratio by measuring the reduction of expression of green fluorescent protein.
Figure 19:
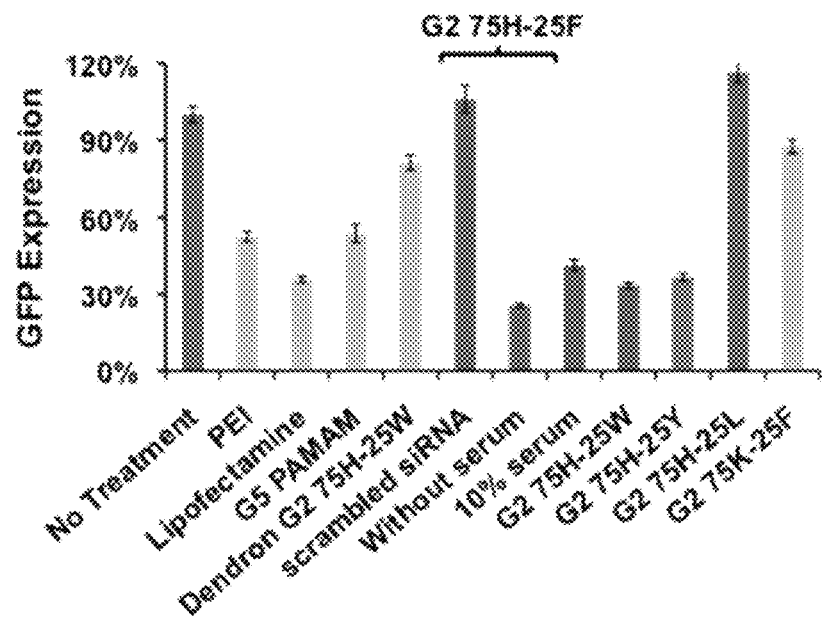
FIG. 19 presents GFP silencing in 3T3 cells by different denpols.

The efficacy of siRNA transfection was first screened using an engineered NIH 3T3 cell line expressing enhanced green fluorescence protein ("GFP"). siRNA against GFP was complexed with different denpols at N/P 20~120 and used to transfect 3T3 cells cultured in a 96-well plates. After incubating for 48 hours, the GFP fluorescence of each well was measured by using a plate reader and the cell viability was determined by an MTT assay. GFP fluorescence was then normalized by percent viability to eliminate toxicity-related GFP reduction. Two benchmark transfection agents, branched poly(ethylene imine) ("PEI," MW~25 kD) and Lipofectamine®, were used as the positive controls. The screening results of transfection efficiency for G2 denpols at optimal N/P ratio are summarized in FIG. 14 (complete screening data for G1 denpols and G2 denpols are shown in FIG. 15 and FIG. 16, respectively).

Denpols carrying both histidine and aromatic amino acids show very high transfection efficiency and low cytotoxicity (75H-25F, 88H-12W, 75H-25Y). Without aromatic groups (75H-25L), no transfection could be observed. And without histidine, substantial silencing only occurred at a very high ratio of hydrophobic amino acid (25K-75F), which caused significant cytotoxicity.

On the basis of the initial screening results, several denpols were selected for more detailed investigation. The dose-dependent toxicity was first determined by MTT assay. As shown in FIG. 12D, all the denpols are two orders of magnitude less toxic than PEI, suggesting the denpols of the disclosure are a very safe platform for siRNA delivery. PEGylation further reduces the toxicity of the denpol system. With 5% PEGylation, the toxicity was greatly reduced at high concentration, and with 10% and 20% PEGylation, the polymers were non-toxic up to 2.5 mg/mL (see FIG. 17).

Flow Cytometry Analysis of siRNA Transfected NIH 3T3 Cells Using Denpols.

The transfection of selected denpols was then repeated and analyzed by flow cytometry for a more accurate measurement. The results agreed well with the initial screening result and confirmed that both histidine and aromatic groups were important for GFP silencing (see FIG. 18A). Denpols with either K-F (lacking H) or H-L (lacking aromatic residue) combinations didn't show any significant gene knockdown. Scrambled siRNA/G2 75H-25W was also transfected and showed minimal effect to GFP expression, indicating high specificity and low off-target effect (see FIG. 18A).

siRNA Transfection Studies in NIH 3T3 Cells Using Denpols in Serum Containing RNase.

For a successful in vivo delivery system, the polyplexes must be able to protect siRNA from the RNase in the serum, and should also have minimum aggregation with negatively charged proteins in serum. In order to study the serum compatibility of the current system, transfection of denpol/siRNA was carried out in DMEM solution containing 10% to 75% fetal bovine serum. Denpol G2 75H-25W was chosen because it showed the highest siRNA binding affinity and high transfection efficiency in serum-free condition. At all serum concentrations tested, this denpol showed significantly higher transfection efficiency over Lipofectamine® (see FIG. 18B). Even at 75% serum concentration, higher than 50% knockdown could still be observed for this denpol.

Figure 20:
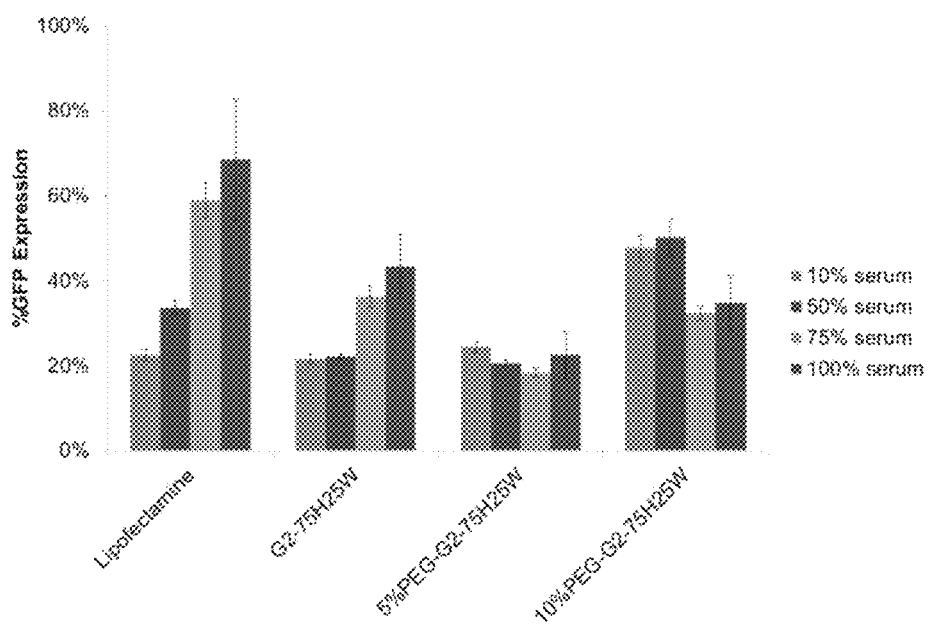
FIG. 20 presents in vitro transfection screening of PEGylated Denpols in Serum. Different denpols were complexed with siRNA at optimized N/P ratio (G2-75H25W N/P=120, 5% PEG-G2-75H25W and 10% PEG-G2-75H25W N/P=400) and transfected to NIH 3T3 cells in different serum concentrations for 24 hours.

In order to study the serum stability of the PEGylated denpol complexes, in vitro transfection was carried out in DMEM containing different concentration of fetal bovine serum. As shown in FIG. 20, transfection efficiency of Lipofectamine® greatly reduces as the serum concentration increases. And without PEGylation, the denpol works well up to 50% serum concentration, but efficiency drops significantly at higher serum concentration. Encouragingly, with 5% or 10% PEGylated denpols, the serum showed minimum effect on the transfection efficiency and high protein knockdown (80%) could still be achieved at 100% concentration. The low toxicity and high transfection efficiency in serum make the PEGylated denpol ideal candidate for in vivo applications.

Intracellular Confocal Fluorescence Trafficking Studies Using Cy3-Labelled siRNA and Select Denpols.

Figure 21:
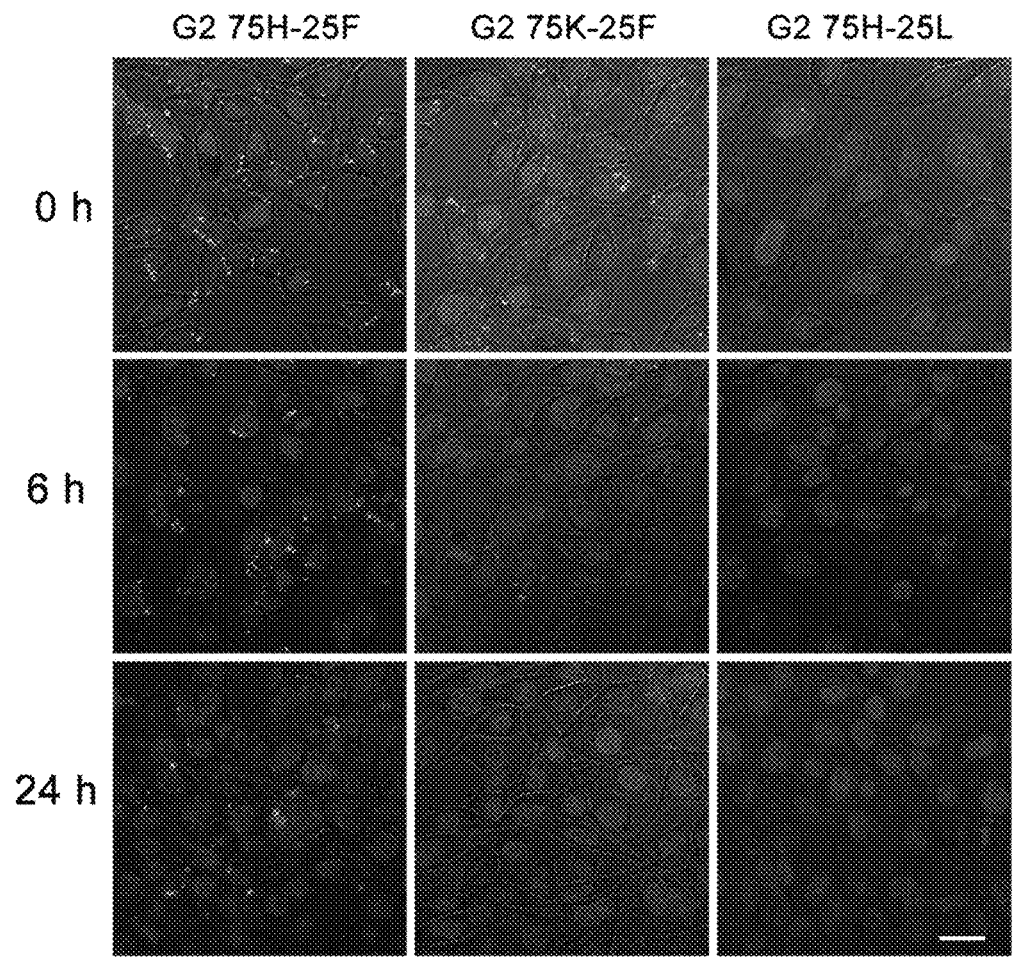
FIG. 21 provides images from an intracellular fluorescence trafficking of transfected NIH 3T3 cells. Cells were incubated with Cy3-labeled siRNA (red) complexed with different denpols for 4 hours. The media was changed back to fresh DMEM with 10% serum. Fluorescence images were taken at 0 hours, 6 hours or 24 hours after the transfection. Cell nucleus was counter-stained with DAPI (blue). Scale bar: 20 µm.
Figure 22:
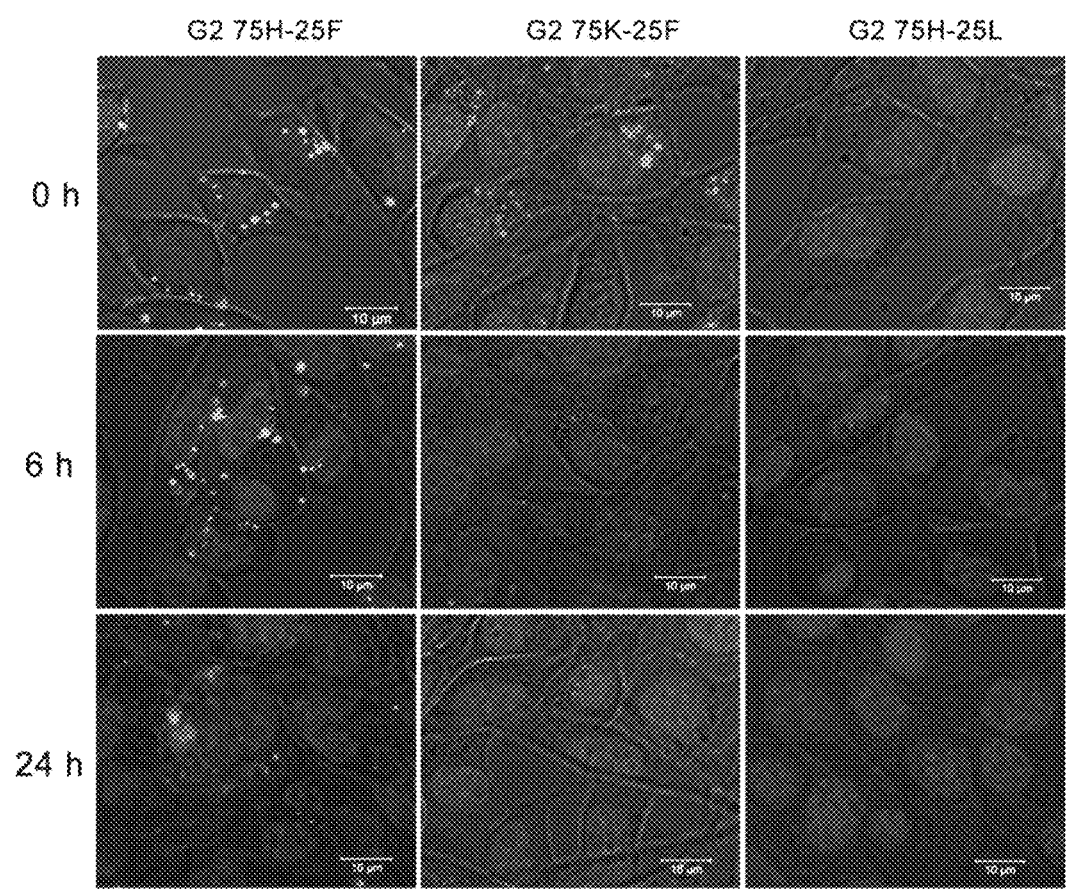
FIG. 22 provides the same images from an intracellular fluorescence trafficking of transfected NIH 3T3 cells as in FIG. 21, but at a much higher magnification.

In order to gain insights into the role of different functional groups, intracellular fluorescence trafficking study using a Cy3-labeled siRNA. Three amphiphilic analogues of G2 denpols were chosen for comparative studies: one having both H and an aromatic residue (G2 75H-25F), one having an aromatic residue but no H (G2 75K-25F), and the last one having H but no aromatic residue (G2 75H-25L). Various Cy3-labeled polyplexes were exposed to 3T3 cells for 4 hours in serum free media and then replaced with normal media with 10% serum. Confocal fluorescence images were taken at different time points after the transfection. As shown in FIG. 21 and FIG. 22, the aromatic residue (F) is important for cellular uptake. While no siRNA internalization was observed with H-L functionalized denpol (G2 75H-25L), both H-F and K-F combinations show very effective cell uptake (G2 75H-25F, G2 75K-25F). On the other hand, the buffering capacity of histidine was also important for successful delivery. In G2 75K-25F transfected cells, the siRNA fluorescence greatly diminished after 6 hours, and no siRNA could be observed 24 hours after transfection. In contrast, siRNA remained present in G2 75H-25F transfected cells for up to 24 hours. It is hypothesized that the buffering capacity of histidine could aid endosomal membrane disruption through either "proton sponge" mechanism or increased amphiphilicity. Without the pH responsive groups (G2 75K-25F), endocytosed siRNA would likely be transported to lysosome, followed by enzymatic degradation and fast clearance.

On the basis of the transfection and fluorescence trafficking results, amphiphilicity of aromatic amino acids and the buffering capacity of histidine could work synergistically for effective siRNA delivery in a denpol system disclosed herein. Denpols with aromatic amino acids (F, W, Y) showed effective cellular uptake and transfection while no cellular uptake or silencing was observed with leucine functionalized denpol (G2 75H-25L). Presumably, the relatively large aromatic hydrophobic groups enhance cellular membrane interaction for the denpol complexes.

Efficient endosomal escape is also important for successful siRNA delivery as most vectors are internalized by endocytosis. The buffering capacity of histidine aids endosomal membrane rupture through either "proton sponge" mechanism or increased amphiphilicity. Therefore, denpols comprising histidine can utilize a low ratio of aromatic groups for effective delivery, while denpols without histidine need a high ratio of incorporated aromatic amino acids. The pH responsiveness ensures the biocompatibility of denpols at neutral pH and also increases membrane lysis at an acidic pH (i.e., endosome) to facilitate endosomal escape.

A number of embodiments have been described herein. Nevertheless, it will be understood that various modifications may be made without departing from the spirit and scope of this disclosure. Accordingly, other embodiments are within the scope of the following claims.

What is claimed is:

1. A dendronized polymer that is biocompatible and capable of forming a polyplex with nucleic acids and releasing the nucleic acids within a cell,
wherein the dendronized polymer comprises branched peptide dendrons that are chemically attached to a linear polymer by disulfide bonds, wherein each dendron is attached to a different point along the length of the linear polymer and wherein no single dendron is attached to more than one point on the polymer, and
wherein the outermost layer of the branched peptide dendrons is functionalized with a plurality of hydrophilic-based amino acids and hydrophobic-based amino acids, and wherein the plurality of hydrophilic-based amino acids and hydrophobic-based amino acids are not directly connected to each other by a peptide bond.

2. The dendronized polymer of claim 1, wherein the outmost layer of the branched peptide dendrons are functionalized with hydrophilic-based amino acids selected from lysine, serine, histidine, proline, arginine, asparagine, glutamic acid, and aspartic acid.

3. The dendronized polymer of claim 1, wherein the outmost layer of the branched peptide dendrons are functionalized with hydrophobic-based amino acids selected from tryptophan, phenylalanine, tyrosine, leucine, alanine, valine, isoleucine, methionine, and cysteine.

4. The dendronized polymer of claim 1, wherein the outermost layer of the branched peptide dendrons are functionalized with hydrophilic amino acids selected from lysine, histidine, and serine, and hydrophobic amino acids selected from phenylalanine, tryptophan, and tyrosine, in a molar ratio of 10:1 to 1:10.

5. The dendronized polymer of claim 4, wherein the molar ratio of hydrophilic amino acids to the hydrophobic amino acids is 4:1 to 1:4.

6. The dendronized polymer of claim 1, wherein the dendronized polymer further comprises a targeting ligand.

7. The dendronized polymer of claim 6, wherein the targeting ligand is selected from antibodies, aptamers, cholesterol and its derivatives, folate compounds or folate conjugates, transferrin, saccharides and cell-penetrating peptides.

8. The dendronized polymer of claim 1, wherein the dendronized polymer further comprises complexed oligonucleotides or polynucleotides.

9. The dendronized polymer of claim 8, wherein oligonucleotides are siRNA.

10. A pharmaceutical composition comprising the dendronized polymer of claim 9.

11. A method of delivering siRNA to a cell in vitro or in vivo comprising contacting the cell with the pharmaceutical composition of claim 10.

12. The method of claim 11, wherein the oligonucleotide induces an RNAi response in the cell.

* * * * *